US008067214B2

(12) United States Patent
Burk et al.

(10) Patent No.: US 8,067,214 B2
(45) Date of Patent: *Nov. 29, 2011

(54) COMPOSITIONS AND METHODS FOR THE BIOSYNTHESIS OF 1,4-BUTANEDIOL AND ITS PRECURSORS

(75) Inventors: Mark J. Burk, San Diego, CA (US); Stephen J. Van Dien, Encinitas, CA (US); Anthony P. Burgard, Bellefonte, PA (US); Wei Niu, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 871 days.

This patent is subject to a terminal disclaimer.

(21) Appl. No.: 12/049,256

(22) Filed: Mar. 14, 2008

(65) Prior Publication Data

US 2009/0075351 A1 Mar. 19, 2009

Related U.S. Application Data

(60) Provisional application No. 60/918,463, filed on Mar. 16, 2007.

(51) Int. Cl.
C12P 7/18 (2006.01)
C12N 1/21 (2006.01)
(52) U.S. Cl. .................................. 435/158; 435/252.33
(58) Field of Classification Search .................. None
See application file for complete search history.

(56) References Cited

U.S. PATENT DOCUMENTS

| 4,048,196 | A | 9/1977 | Broecker et al. |
| 4,228,949 | A | 10/1980 | Jackson |
| 4,240,578 | A | 12/1980 | Jackson |
| 4,301,077 | A | 11/1981 | Pesa et al. |
| 4,430,430 | A | 2/1984 | Momose et al. |
| 4,652,685 | A | 3/1987 | Cawse et al. |
| 4,876,331 | A | 10/1989 | Doi |
| 5,164,309 | A | 11/1992 | Gottschalk et al. |
| 5,245,023 | A | 9/1993 | Peoples et al. |
| 5,250,430 | A | 10/1993 | Peoples et al. |
| 5,286,842 | A | 2/1994 | Kimura |
| 5,292,860 | A | 3/1994 | Shiotani et al. |
| 5,378,616 | A | 1/1995 | Tujimoto et al. |
| 5,413,922 | A | 5/1995 | Matsuyama et al. |
| 5,461,139 | A | 10/1995 | Gonda et al. |
| 5,475,086 | A | 12/1995 | Tobin et al. |
| 5,478,952 | A | 12/1995 | Schwartz |
| 5,502,273 | A | 3/1996 | Bright et al. |
| 5,516,883 | A | 5/1996 | Hori et al. |
| 5,534,432 | A | 7/1996 | Peoples et al. |
| 5,563,239 | A | 10/1996 | Hubbs et al. |
| 5,602,321 | A | 2/1997 | John |
| 5,610,041 | A | 3/1997 | Somerville et al. |
| 5,650,555 | A | 7/1997 | Somerville et al. |
| 5,663,063 | A | 9/1997 | Peoples et al. |
| 5,674,978 | A | 10/1997 | Tobin et al. |
| 5,705,626 | A | 1/1998 | Tobin et al. |
| 5,747,311 | A | 5/1998 | Jewell |
| 5,750,848 | A | 5/1998 | Krüger et al. |
| 5,770,435 | A | 6/1998 | Donnelly et al. |
| 5,830,716 | A | 11/1998 | Kojima et al. |
| 5,846,740 | A | 12/1998 | Tobin et al. |
| 5,849,894 | A | 12/1998 | Clemente et al. |
| 5,869,301 | A | 2/1999 | Nghiem et al. |
| 5,908,924 | A | 6/1999 | Burdette et al. |
| 5,942,660 | A | 8/1999 | Gruys et al. |
| 5,958,745 | A | 9/1999 | Gruys et al. |
| 5,994,478 | A | 11/1999 | Asrar et al. |
| 5,998,366 | A | 12/1999 | Tobin et al. |
| 6,010,870 | A | 1/2000 | Pelzer et al. |
| 6,011,139 | A | 1/2000 | Tobin et al. |
| 6,011,144 | A | 1/2000 | Steinbuchel et al. |
| 6,022,729 | A | 2/2000 | Steinbuchel et al. |
| 6,080,562 | A | 6/2000 | Byrom et al. |
| 6,091,002 | A | 7/2000 | Asrar et al. |
| 6,111,658 | A | 8/2000 | Tabata |
| 6,117,658 | A | 9/2000 | Dennis et al. |

(Continued)

FOREIGN PATENT DOCUMENTS

| CA | 2006506 | 4/1991 |
| GB | 1230276 | 4/1971 |
| GB | 1314126 | 4/1973 |
| GB | 1344557 | 1/1974 |
| GB | 1512751 | 6/1978 |
| JP | 62 285779 | 12/1987 |
| JP | 62285779 | 12/1987 |
| KR | 10-2004-0060149 | 7/2004 |
| KR | 10-2005-0076301 | 8/2005 |
| KR | 10-2005-0076317 | 8/2005 |
| KR | 10-2005-0076348 | 8/2005 |
| KR | 10-2006-0026599 | 3/2006 |
| KR | 10-2009-0025902 | 3/2009 |
| WO | WO 82/08354 | 4/1982 |
| WO | WO 91/00917 | 1/1991 |

(Continued)

OTHER PUBLICATIONS

Abe et al., "Biosynthesis from gluconate of a random copolyester consisting of 3-hydroxybutyrate and medium-chain-length 3-hydroxyalkanoates by *Pseudomonas* sp. 61-3.," *Int. J. Biol. Macromol.* 16:115-119 (1994).

(Continued)

*Primary Examiner* — James Ketter
*Assistant Examiner* — Channing S Mahatan
(74) *Attorney, Agent, or Firm* — Jones Day

(57) ABSTRACT

The invention provides a non-naturally occurring microbial organism having 4-hydroxybutanoic acid (4-HB) and 1,4-butanediol (1,4-BDO) biosynthetic pathways. The pathways include exogenous nucleic acids encoding a) an α-ketoglutarate decarboxylase; b) a 4-hydroxybutanoate dehydrogenase; c) a 4-hydroxybutyryl-CoA:acetyl-CoA transferase or a butyrate kinase and a phosphotransbutyrylase; d) an aldehyde dehydrogenase, and e) an alcohol dehydrogenase, wherein the exogenous nucleic acids are expressed in sufficient amounts to produce 1,4-butanediol (1,4-BDO). Also provide is a method for the production of 1,4-BDO. The method includes culturing the non-naturally occurring microbial organism having 4-HB and 1,4-BDO biosynthetic pathways substantially anaerobic conditions for a sufficient period of time to produce 1,4-BDO.

12 Claims, 14 Drawing Sheets

U.S. PATENT DOCUMENTS

| | | | |
|---|---|---|---|
| 6,156,852 A | 12/2000 | Asrar et al. |
| 6,159,738 A | 12/2000 | Donnelly et al. |
| 6,204,341 B1 | 3/2001 | Asrar et al. |
| 6,228,623 B1 | 5/2001 | Asrar et al. |
| 6,248,862 B1 | 6/2001 | Asrar et al. |
| 6,277,586 B1 | 8/2001 | Tobin et al. |
| 6,280,986 B1 | 8/2001 | Hespell et al. |
| 6,316,262 B1 | 11/2001 | Huisman et al. |
| 6,329,183 B1 | 12/2001 | Skraly et al. |
| RE37,543 E | 2/2002 | Krüger et al. |
| 6,448,061 B1 | 9/2002 | Pan et al. |
| 6,448,473 B1 | 9/2002 | Mitsky et al. |
| 6,455,267 B1 | 9/2002 | Tobin et al. |
| 6,495,152 B2 | 12/2002 | Steinbuchel et al. |
| 6,515,205 B1 | 2/2003 | Liebergesell et al. |
| 6,576,450 B2 | 6/2003 | Skraly et al. |
| 6,593,116 B1 | 7/2003 | Huisman et al. |
| 6,596,521 B1 | 7/2003 | Chang et al. |
| 6,623,946 B1 | 9/2003 | Möckel et al. |
| 6,682,906 B1 | 1/2004 | Tobin et al. |
| 6,686,310 B1 | 2/2004 | Kourtakis et al. |
| 6,689,589 B2 | 2/2004 | Huisman et al. |
| 6,730,503 B1 | 5/2004 | Asakura et al. |
| 6,759,219 B2 | 7/2004 | Hein et al. |
| 6,770,464 B2 | 8/2004 | Steinbuchel et al. |
| 6,835,820 B2 | 12/2004 | Cannon et al. |
| 6,897,055 B2 | 5/2005 | Möckel et al. |
| 6,913,911 B2 | 7/2005 | Huisman et al. |
| 6,916,637 B2 | 7/2005 | Rieping et al. |
| 7,052,883 B2 | 5/2006 | Rieping et al. |
| 7,081,357 B2 | 7/2006 | Huisman et al. |
| 7,125,693 B2 | 10/2006 | Davis et al. |
| 7,127,379 B2 | 10/2006 | Palsson et al. |
| 7,132,267 B2 | 11/2006 | Davis et al. |
| 7,135,315 B2 | 11/2006 | Hoshino et al. |
| 7,186,541 B2 | 3/2007 | Gokarn et al. |
| 7,223,567 B2 | 5/2007 | Ka-Yiu et al. |
| 7,229,804 B2 | 6/2007 | Huisman et al. |
| 7,256,021 B2 | 8/2007 | Hermann |
| 7,309,597 B2 | 12/2007 | Liao et al. |
| 7,393,676 B2 | 7/2008 | Gokman et al. |
| 7,858,350 B2 * | 12/2010 | Burk et al. ............... 435/158 |
| 2002/0012939 A1 | 1/2002 | Palsson |
| 2002/0164729 A1 | 11/2002 | Skraly et al. |
| 2002/0168654 A1 | 11/2002 | Maranas et al. |
| 2003/0059792 A1 | 3/2003 | Palsson et al. |
| 2003/0224363 A1 | 12/2003 | Park et al. |
| 2003/0233218 A1 | 12/2003 | Schilling |
| 2004/0009466 A1 | 1/2004 | Maranas et al. |
| 2004/0023347 A1 | 2/2004 | Skraly |
| 2004/0029149 A1 | 2/2004 | Palsson et al. |
| 2004/0072723 A1 | 4/2004 | Palsson et al. |
| 2004/0096946 A1 | 5/2004 | Kealey et al. |
| 2004/0106176 A1 | 6/2004 | Skraly |
| 2004/0152159 A1 | 8/2004 | Causey et al. |
| 2004/0152166 A1 | 8/2004 | Mockel |
| 2005/0042736 A1 | 2/2005 | San et al. |
| 2005/0090645 A1 | 4/2005 | Asakura |
| 2005/0164342 A1 | 7/2005 | Tobin |
| 2005/0170480 A1 | 8/2005 | Huisman |
| 2005/0239179 A1 | 10/2005 | Skraly et al. |
| 2005/0287655 A1 | 12/2005 | Tabata et al. |
| 2006/0046288 A1 | 3/2006 | Ka-Yiu et al. |
| 2006/0084155 A1 | 4/2006 | Huisman et al. |
| 2006/0134760 A1 | 6/2006 | Rieping |
| 2006/0141594 A1 | 6/2006 | San et al. |
| 2007/0072279 A1 | 3/2007 | Meynial-Salles et al. |
| 2007/0087425 A1 | 4/2007 | Ohto |
| 2007/0184539 A1 | 8/2007 | San et al. |
| 2007/0190605 A1 | 8/2007 | Bessler et al. |
| 2008/0120732 A1 * | 5/2008 | Elliot ............... 800/4 |
| 2008/0138870 A1 | 6/2008 | Bramucci et al. |
| 2008/0171371 A1 | 7/2008 | Yukawa et al. |
| 2008/0182308 A1 | 7/2008 | Donaldson et al. |
| 2008/0293125 A1 | 11/2008 | Subbian et al. |
| 2009/0047719 A1 | 2/2009 | Burgard et al. |
| 2009/0075351 A1 | 3/2009 | Burk et al. |
| 2010/0099925 A1 | 4/2010 | Kharas |

FOREIGN PATENT DOCUMENTS

| | | |
|---|---|---|
| WO | WO 92/19747 | 11/1992 |
| WO | WO 93/02187 | 2/1993 |
| WO | WO 93/02194 | 4/1993 |
| WO | WO 93/06225 | 4/1993 |
| WO | WO 94/11519 | 5/1994 |
| WO | WO 94/12014 | 6/1994 |
| WO | WO 94/20614 | 9/1994 |
| WO | WO 94/20615 | 9/1994 |
| WO | WO 95/11985 | 5/1995 |
| WO | WO 96/20621 | 7/1996 |
| WO | WO 99/06532 | 2/1999 |
| WO | WO 99/14313 | 3/1999 |
| WO | WO 00/61763 | 10/2000 |
| WO | WO 02/055995 | 7/2002 |
| WO | WO 02/061115 | 8/2002 |
| WO | WO 03/008603 | 1/2003 |
| WO | WO 03/106998 | 12/2003 |
| WO | WO 2004/018621 | 3/2004 |
| WO | WO 2004/029235 | 4/2004 |
| WO | WO 2005/026338 | 3/2005 |
| WO | WO 2005/052135 | 6/2005 |
| WO | WO 2007/030830 | 3/2007 |
| WO | WO 2007/141208 | 12/2007 |
| WO | WO 2008/027742 | 6/2008 |
| WO | WO 2008/115840 | 9/2008 |
| WO | WO 2008/131286 A1 | 10/2008 |
| WO | WO 2008/144626 | 11/2008 |
| WO | WO 2009/011974 | 1/2009 |
| WO | WO 2009/023493 | 2/2009 |
| WO | WO 2009/031766 | 3/2009 |
| WO | WO 2009/049274 A2 | 4/2009 |
| WO | WO 2009/094485 A1 | 7/2009 |
| WO | WO 2009/103026 A1 | 8/2009 |
| WO | WO 2009/131040 | 10/2009 |
| WO | WO 2010/006076 | 1/2010 |
| WO | WO/2010/085731 | 7/2010 |

OTHER PUBLICATIONS

Aidoo et al., "Cloning, sequencing and disruption of a gene from *Streptomyces clavuligerus* Involved in clavulanic acid biosynthesis," *Gene* 147:41-46 (1994).

Alberty "Biochemical thermodynamics," *Biochem. Biophys. Acta* 1207:1-11 (1994).

Allen et al., "DNA sequence of the putA gene from *Salmonella typhimurium*: a bifunctional membrane-associated dehydrogenase that binds DNA," *Nucleic Acids Res.* 21:1676 (1993).

Amarasingham and Davis, "Regulation of alpha-ketoglutarate dehydrogenase formation in *Escherichia coli*," *J. Biol. Chem.* 240: 3664-3668 (1965).

Amos and McInerey, "Composition of poly-.beta.-hydroxyalkanoate from *Syntrophomonas wottei* grown on unsaturated fatty acid substrates," *Arch. Microbiol.* 155:103-106 (1991).

Amuro et al., "Isolation and characterization of the two distinct genes for human glutamate dehydrogenase," *Biochem. Biophys. Acta* 1049:216-218 (1990).

Andre and Jauniaux, "Nucleotide sequence of the yeast UGA1 gene encoding GABA transaminase," *Nucl. Acid Res.* 18:3049 (1990).

Bartsch et al., "Molecular analysis of two genes of the *Escherichia coli* gab cluster: nucleotide sequence of the glutamate:succinic semialdehyde transaminase gene (gabT) and characterization of the succinic semialdehyde dehydrogenase gene (gabD)," *J. Bacteriol.* 172:7035-7042 (1990).

Baum et al., "A plant glutamate decarboxylase containing a calmodulin binding domain, Cloning, sequence, and functional analysis," *J. Biol. Chem.* 268:19610-19617 (1993).

Benachenhou-Lahfa et al., "PCR-mediated cloning and sequencing of the gene encoding glutamate dehydrogenase from the archaeon *Sulfolobus shilbatae*: Identification of putative amino-acid signatures for extremophilic adaptation," *Gene* 140:17-24 (1994).

Blattner et al., "The complete genome sequence of *Escherichia coli* K-12," *Science* 277:1453-1474 (1997).

Botsford et al., "Accumulation of glutamate by *Salmonella typhimurium* in response to osmotic stress," *Appl. Environ. Microbiol.* 60:2568-2574 (1994).

Brandl et al., "Ability of the phototrophic bacterium *Rhodospirillum rubrum* to produce various poly (beta-hydroxyalkanoates): potential sources for biodegradable polyesters," *Int. J. Biol. Macromol.* 11:49-55 (1989).

Bridger et al., "The subunits of succinyl-coenzyme A synthetase—function and assembly," *Biochem Soc Symp.* 54:103-111 (1987).

Bu et al., "The exon-intron organization of the genes (GAD1 and GAD2) encoding two human glutamate decarboxylases (GAD67 and GAD65) suggests that they derive from a common ancestral GAD," *Genomics* 21:222-228 (1994).

Buck and Guest, "Overexpression and site-directed mutagenesis of the succinyl-CoA synthetase of *Escherichia coli* and nucleotide sequence of a gene (g30) that is adjacent to the suc operon," *Biochem J.* 260(3):737-747 (1989).

Buck et al., "Cloning and expression of the succinyl-CoA synthetase genes of *Escherichia coli* K12," *J. Gen. Microbiol.* 132(6):1753-1762 (1986).

Buck et al., "Primary structure of the succinyl-CoA synthetase of *Escherichia coli*," *Biochemistry* 24:6245-6552 (1985).

Bult et al., "Complete genome sequence of the methanogenic archaeon, *Methanococcus jarnnaschil*," *Science* 273:1058-1073 (1996).

Burgard, "Probing the performance limits of the *Escherichia coli* metabolic network subject to gene additions or deletions," *Biotechnol. Bioeng*, 74:364-375 (2001).

Burgard et al., "OptKnock: A bilevel programming framework for identifying gene knockout strategies for microbial strain optimization," *Biotechnol. Bioeng.* 84:647-657 (2003).

Burgard et al., "Minimal reaction sets for *Escherichia coli* metabolism under different growth requirements and uptake environments," *Biotechnol. Prog.* 17:791-797 (2001).

Causey et al., "Engineering *Escherichia coli* for efficient conversion of glucose to pyruvate," *Proc. Natl. Acad. Scie USA* 101:2235-2240 (2004).

Chavez et al., "The NADP-glutamate dehydrogenase of the cyanobacterium Synechocystis 6803: cloning, transcriptional analysis and disruption of the gdhA gene," *Plant Mol. Biol.* 28:173-188 (1995).

Chen and Lin, "Regulation of the adhE gene, which encodes ethanol dehydrogenase in *Escherichia coli*," *J Bacteriol.* 173(24):8009-8013 (1991).

Chu et al., "Enzymatically active truncated cat brain glutamate decarboxylase: expression, purification, and absorption spectrum," *Arch. Biochem. Biophys.* 313:287-295 (1994).

Cock et al., "A nuclear gene with many introns encoding ammonium-inductible chloroplastic NADP-specific glutamate dehydrogenase(s) in *Chlorella sorokiniana*," *Plant Mol. Biol.* 17:1023-1144 (1991).

Cogoni et al., "*Saccharomyces cerevisiae* has a single glutamate synthase gene coding for a plant-like high-molecular-weight polypeptide," *J. Bacteriol.* 177:792-798 (1995).

Cole et al., "Deciphering the biology of *Mycobacterium tuberculosis* from the complete genome sequence," *Nature* 393:537-544 (1998).

Coleman et al., "Expression of a glutamate decarboxylase homologue is required for normal oxidative stress tolerance in *Saccharomyces cerevisiae*," *J. Biol. Chem.* 276:244-250 (2001).

Creaghan and Guest, "Succinate dehydrogenase-dependent nutritional requirement for succinate in mutants of *Escherichia coli* K12," *J Gen Microbiol.* 107(1):1-13 (1978).

Cunningham and Guest, "Transcription and transcript processing in the sdhCDAB-sucABCD operon of *Escherichia coli*," *Microbiology* 144:2113-2123 (1998).

Darlison et al., "Nucleotide sequence of the sucA gene encoding the 2-oxoglutarate dehydrogenase of *Escherichia coli* K12," *Eur. J. Biochem.* 141(2):351-359 (1984).

Database WPI Week 198804 Thomson Scientific, London, GB; AN 1988-025175.

Datsenko and Wanner, "One-step inactivation of chromosomal genes in *Escherichia coli* K-12 using PCR products," *Proc. Natl. Acad. Sci. USA* 97(12):6640-6645 (2000).

Deckert et al., "The complete genome of the hyperthermophilic bacterium *Aquifex aeolicus*," *Nature* 392:353-358 (1998).

Diruggiero et al., "Expression and in vitro assembly of recombinant glutamate dehydrogenase from the hyperthermophilic archaeon *Pyrococcus turiosus*," *Appl. Environ. Microbiol.* 61:159-164 1995.

Doi, "Microbial Synthesis, Physical Properties, and Biodegradability of Polyhydroxyalkanoates," *Macromol. Symp.* 98:585-599 (1995).

Doi et al., "Biosynthesis and characterization of poly(3-hydroxybutyrate-co-4-hydroxybutyrate) in *Alcaligenes eutrophus*," *Int. J. Biol. Macromol.* 12:106-111 (1990).

Doi et al., "Nuclear Magnetic Resonance Studies on Unusual Bacterial Copolyesters of 3-Hydroxybutyrate and 4-Hydroxybutyrate," *Macromolecules* 21:2722-2727 (1988).

Dombek and Ingram, "Ethanol Production during Batch Fermentation with *Saccharomyces cerevisiae*: Changes in Glycolytic Enzymes and Internal pH", *App. and Environ. Microb.* (1987).

Donnelly and Cooper, "Succinic semialdehyde dehydrogenases of *Escherichia coli*: their role in the degradation of p-hydroxyphenylacetate and gamma-aminobutyrate," *Eur. J. Biochem.* 113(3):555-561 (1981).

Donnelly and Cooper, "Two Succinic Semialdehyde Dehydrogenases are Induced when *Escherichia coli* K-12 is Grown on γ-Aminobutyrate", *J. of Bacteriol*, 1425-1427 (1981).

Dover et al., "Genetic analysis of the gamma-aminobutyrate utilization pathway in *Escherichia coli* K-12," *J. Bacteriol.* 117(2):494-501 (1974).

Duncan et al., "Purification and properties of NADP-dependent glutamate dehydrogenase from *Ruminococcus flavefaciens* FD-1," *Appl. Environ. Microbiol.* 58:4032-4037 (1992).

Edwards and Palsson, "Systems properties of the *Haemophilus influenzae* Rd metabolic genotype," *J. Biol. Chem.* 274:17410-17416 (1999).

Edwards and Palsson, "The *Escherichia coli* MG1655 in silico metabolic genotype: its definition, characteristics, and capabilities," *Proc. Natl. Acad. Sci. USA* 97:5528-5533 (2000).

Edwards et al., "In silico predictions of *Escherichia coli* metabolic capabilities are consistent with experimental data,"*Nature Biotech.* 19:125-130 (2001).

Eggen et al., "The glutamate dehydrogenase-encoding gene of the hyperthermophilic archaeon *Pyrococcus furiosus*: sequence, transcription and analysis of the deduced amino acid sequence," *Gene* 132:143-148 (1993).

Fell and Small, "Fat synthesis in adipose tissue. An examination of stoichiometric constraints," *Biochem J.* 238:781-786 (1986).

Filetici et al., "Sequence of the GLT1 gene from *Saccharomyces cerevisiae* reveals the domain structure of yeast glutamate synthase," *Yeast* 12:1359-1366 (1996).

Föllner et al., "Analysis of the PHA granule-associate proteins GA20 and GA11 in *Methylobacterium extorquens* and *Methylobacterium rhodesianum*," *J Basic Microbiol.* 37(1):11-21 (1997).

Fong and Palsson, "Metabolic gene-deletion strains of *Escherichia coli* evolve to computationally predicted growth phenotypes," *Nat. Genet.* 36(10):1056-1058 (2004).

Fong et al., "Description and interpretation of adaptive evolution of *Escherichia coli* K-12 MG1655 by using a genome-scale in silico metabolic model," *J. Bacteriol.* 185:6400-6408 (2003).

Fontaine et al., "Molecular characterization and transcriptional analysis of adhE2, the gene encoding the NADH-dependent aldehyde/alcohol dehydrogenase responsible for butanol production in alcohologenic cultures of *Clostridium acetobutylicum* ATCC 824," *J Bacteriol.* 184(3):821-830 (2002).

Forster et al., "Genome-scale reconstruction of the *Saccharomyces cerevisiae* metabolic network," *Genome Res.* 13:244-253 (2003).

Fuhrer et al., "Computational prediction and experimental verification of the gene encoding the NAD+/NADP+-dependent succinate semialdehyde dehydrogenase in *Escherichia coli*," *J. Bacteriol.*, PubMed ID 17873044 [Epub ahead of print] (2007).

Gallego, et al., "A role for glutamate decarboxylase during tomato ripening: the characterisation of a cDNA encoding a putative glutamate decarboxylase with a calmodulin-binding site," *Plant Mol. Biol.* 27:1143-1151 (1995).

Gerhardt et al., "Fermentation of 4-aminobutyrate by *Clostridium aminobutyricum*: cloning of two genes involved in the formation and dehydration of 4-hydroxybutyryl-CoA," *Arch Microbiol.* 174(3):189-199 (2000).

Gerngross et al., "Enzyme-catalyzed synthesis of poly((R)-(−)-3-hydroxybutyrate): formation of macroscopic granules in vitro," *Proc. Natl. Acad. Sci. USA* 92:6279-6783 (1995).

Gerngross et al., "Overexpression and purification of the soluble polyhydroxyalkanoate synthase from *Alcalligenes eutrophus*: evidence for a required posttranslational modification for catalytic activity," *Biochemistry* 33:9311-9320 (1994).

Girbal et al., "Regulation of metabolic shifts in *Clostridium acetobutylicum* ATCC," *FEMS Microbiology Reviews*, 17:287-297 (1995).

Gonzalez et al., "Cloning of a yeast gene coding for the glutamate synthase small subunit (GUS2) by complementation of *Saccharomyces cerevisiae* and *Escherichia coli* glutamate auxotrophs," *Mol. Microbiol.* 6:301-308 (1992).

Gonzalez-Pajuelo et al., "Metabolic engineering of *Clostridium acetobutylicum* for the industrial production of 1,3-propanediol from glycerol," *Met. Eng.* 7:329-336 (2005).

Gregerson et al., "Molecular characterization of NADH-dependent glutamate synthase from alfalfa nodules," *Plant Cell* 5:215-226 (1993).

Guzman et al., "Tight regulation, modulation and high-level expression by vectors containing the arabinose PNAD promoter," *J. Bacteriol.* 177(14):4121-4130 (1995).

Hein et al., "Biosynthesis of poly(4-hydroxybutyric acid) by recombinant strains of *Escherichia coli*," *FEMS Microbiol. Lett.* 153(2):411-418 (1997).

Henne et al., "Construction of environmental DNA libraries in *Escherichia coli* and screening for the presence of genes conferring utilization of 4-hydroxybutyrate," *Appl. Environ. Microbiol.* 65(9):3901-3907 (1999).

Hennessy et al., "The reactivity of gamma-hydroxybutyric acid (GHB) and gamma-butyrolactone (GBL) in alcoholic solutions," *J. Forensic Sci.* 49(6):1220-1229 (2004).

Hezayen et al., "Biochemical and enzymological properties of the polyhydroxybutyrate synthase from the extremely halophilic archaeon strain 56," *Arch. Biochem Biophys.* 403(2):284-291 (2002).

Hiramitsu et al., "Production of Poly(3-hydroxybutyrate-co-4-hydroxybutyrate) by *Alcallgenes latus*," *Biotechnol. Lett.* 15:461-464 (1993).

Hong et al., "The genome sequence of the capnophilic rumen bacterium *Mannheimia succiniciproducens*," *Nat. Biotechnol.* 22(10):1275-1281 (2004).

Huh et al., "Global analysis of protein localization in budding yeast," *Nature* 425:686-691 (2003).

Ibarra et al., "*Escherichia coli* K-12 undergoes adaptive evolution to achieve in silico predicted optimal growth," *Nature* 420(6912):186-189 (2002).

Imai and Ohno, "Measurement of yeast intracellular pH by image processing and the change it undergoes during growth phase," *J. Biotechnol.* 38:165-172 (1995).

Ishida et al., "Efficient production of L-Lactic acid by metabolically engineered *Saccharomyces cerevisiae* with a genome-integrated L-lactate dehydrogenase gene," *Appl. Environ. Microbiol.* 71:1964-1970 (2005).

Jesudason and Marchessault, "Synthetic Poly[(R,S)-.beta.-hydroxyalkanoates] with Butyl and Hexyl Side Chains," *Macromolecules* 27:2595-2602 (1994).

Jewell et al., "Bioconversion of propionic, valeric and 4-hydroxybutyric acids into the corresponding alcohols by *Clostridium acetobutylicum* NRRL," *Current Microbiology* 13(4):215-219 (1986).

Johnston et al., "Complete nucleotide sequence of *Saccharomyces cerevisiae* chromosome VIII," *Science* 265:2077-2082 (1994).

Jones et al., "Purification and characterization of D-beta-hydroxybutyrate dehydrogenase expressed in *Escherichia coli*," *Biochem Cell Biol.* 71(7-8):406-410 (1993).

Kaneko et al., "Sequence analysis of the genome of the unicellular cyanobacterium *Synechocystis* sp. strain PCC6803, II. Sequence determination of the entire genome and assignment of potential protein-coding regions," *DNA Res.* 3:109-136 (1996).

Kato et al., "Open reading frame 3 of the barotolerant bacterium strain DSS12 is complementary with cydD in *Escherichia coli*: cydD functions are required for cell stability at high pressure," *J. Biochem.* 120:301-305 (1996).

Kato et al., "Production of a novel copolyester of 3-hydroxybutyric acid with a medium-chain-length 3-hydroxyalkanoic acids by *Pseudomonas* sp. 61-3 from sugars," *Appl Microbiol. Biotechnol.* 45:363-370 (1996).

Kim et al., "Effect of overexpression of *Actinobacillus succinogenes* phosphoenolpyruvate carboxykinase on succinate production in *Escherichia coli*," *Appl. Environ. Microbiol.* 70:1238-1241 (2004).

Kimura et al., "Production of Poly(3-hydroxybutyrate-co-4-hydroxybutyrate) by *Pseudomonas acidovorans*," *Biotechnol. Lett.* 14:445 (1992).

Kinnaird et al., "The complete nucleotide sequence of the *Neurospora crassa* am (NADP-specific glutamate dehydrogenase) gene," *Gene* 26:253-260 (1983).

Kirby et al., "Purification and properties of rabbit brain and liver 4-aminobutyrate aminotransferases isolated by monoclonal-antibody Immunoadsorbent chromatography," *Biochem. J.* 230:481-488 (1985).

Klenk et al., "The complete genome sequence of the hyperthermophilic, sulphate-reducing archaeon *Archaeoglobus fulgidus*," *Nature* 390:364-370 (1997).

Kunioka et al., "New bacterial copolyesters produced in *Alcaligenes eutrophus* from organic acids," *Polym. Commun.* 29:174-176 (1988).

Kwon et al., "Influence of gluconeogenic phosphoenolpyruvate carboxykinase (PCK) expression on succinic acid fermentation in *Escherichia coli* under high bicarbonate condition," *J. Microbiol. Biotechnol.* 16(9):1448-1452 (2006).

Kwon et al., "Brain 4-aminobutyrate aminotransferase. Isolation and sequence of a cDNA encoding the enzyme," *J. Biol. Chem.* 267:7215-7216 (1992).

Lageveen et al., "Formation of Polyesters by *Pseudomonas oleovorans*: Effect of Substrates on Formation and Composition of Poly-(R)-3-Hydroxyalkanoates and Poly(R)-3-Hydroxyalkenoates," *Appl. Environ. Microbiol.* 54:2924-2932 (1988).

Lee et al., "Biosynthesis of copolyesters consisting of 3-hydroxybutyric acid and medium-chain-length 3-hydroxyalkanoic acids from 1,3-butanediol or from 3-hydroxybutyrate by *Pseudomonas* sp. A33," *Appl. Microbiol. Biotechnol.* 42: 901-909 (1995).

Lee et al., "Enhanced biosynthesis of P(3HB-3HV) and P(3HB-4HB) by amplification of the cloned PHB biosynthesis genes in *Alcatigenes eutrophus*," *Biotechnol. Lett.* 19:771-774 (1997).

Lemoigne and Rouklehman, "Fermentation b-Hydroxybutyrique," *Annales des Fermentations* 5:527-536 (1925).

Liebergesell and Steinbuchel, "Cloning and nucleotide sequences of genes relevant for biosynthesis of poly(3-hydroxybutyric acid) in *Chromatium vinosum* strain D," *Eur. J. Biochem.* 209(1):135-150 (1992).

Liu and Steinbuchel, "Exploitation of butyrate kinase and phosphotransbutyrylase from *Clostridium acetobutylicum* for the in vitro biosynthesis of poly (hydroxyalkanoic acid)," *Appl. Microbiol. Biotechnol.* 53(5):545-552 (2000).

Lu et al., "Enhanced production of poly(3-hydroxybutyrate-co-3-hydroxyhexanoate) via manipulating the fatty acid beta-oxidation pathway in *E. coli*," *FEMS Microbiol Lett.* 221(1):97-101 (2003).

Lu et al., "Molecular cloning of polyhydroxyalkanoate synthesis operon from *Aeromonas hydrophilia* and its expression in *Escherichia coli*," *Biotechnol Prog.* 20(5):1332-1336 (2004).

Lutke-Eversloh and Steinbuchel, "Biochemical and molecular characterization of a succinate semialdehyde dehydrogenase involved in the catabolism of 4-hydroxybutyric acid in *Ralstonia eutropha*," *FEMS Microbiol. Lett.* 181:63-71 (1999).

Mahadevan et al., "The effects of alternate optimal solutions in constraint-based genome-scale metabolic models," *Metab. Eng.* 5:264-276 (2003).

Majewski and Domach, "Simple constrained-optimization view of acetate overflow in *E. coli*," *Biotech Bioeng*, 35:732-738 (1990).

Majumdar et al., "Functional consequences of substitution in the active site (phosphor) histidine residue of *Escherichia coli* succinyl-CoA synthetase," *Biochim Biophys Acta* 1076:86-90 (1991).

Mandal and Ghosh, "Isolation of a glutamate synthase (GOGAT)-negative, pleiotropically N utilization-defective mutant of *Azospirillum brasilense*: cloning and partial characterization of GOGAT structural gene," *J. Bacteriol.* 175:8024-8029 (1993).

Marek and Henson, "Cloning and expression of the *Escherichia coli* K-12 sad gene," *J. Bacteriol.* 170(2):991-994 (1988).

Mat-Jan et al., "Anaerobic growth defects resulting from gene fusions affecting succinyl-CoA synthetase in *Escherichia coli* K12," *Mol. Gen. Genet.* 215:276-280 (1989).

Mavrovouniotis, M.L., "Estimation of standard Gibbs energy changes of biotransformations," *J. Biol. Chem.* 266:14440-14445 (1991).

McLaggan et al., "Interdependence of K+ and glutamate accumulation during osmotic adaptation of *Escherichia coli*," *J. Biol. Chem.* 269:1911-1917 (1994).

Metzer and Halpern, "In vivo cloning and characterization of the gabCTDP gene cluster of *Escherichia coli* K-12," *J. Bacteriol.* 172:3250-3256 (1990).

Metzer et al., "Isolation and properties of *Escherichia coli* K-12 mutants impaired in the utilization of gamma-aminobutyrate," *J Bacteriol.* 137(3):1111-1118 (1979).

Miles and Guest, "Molecular genetic aspects of the citric acid cycle of *Escherichia coli*," *Biochem Soc. Symp.* 54:45-65 (1987).

Miller et al., "Cloning and characterization of gdhA, the structural gene for glutamate dehydrogenase of *Salmonella typhimurium*," *J. Bacteriol.* 157:171-178 (1984).

Miyamoto et al., "Possible physiological roles of aspartase, NAD- and NADP-requiring glutamate dehydrogenases of *Pseudomonas fluorescens*," *J. Biochem.* 112:52-56 (1992).

Mountain et al., "The *Klebsiella aerogenes* glutamate dehydrogenase (gdnA) gene: cloning, high-level expression and hybrid enzyme formation in *Escherichia coli*," *Mol. Gen. Genet.* 199:141-145 (1985).

Nagasu et al., "Nucleotide Sequence of the GDH gene coding for the NADP-specific glutamate dehydrogenase of *Saccharomyces cerevisiae*," *Gene* 37:247-253 (1984).

Neidhardt et al., *Escherichia coli and Salmonella: Cellular and Molecular Biology*, 2nd ed., (xx, 2822, lxxvi) ASM Press, Washington, D.C. (1996).

Niegemann et al., "Molecular organization of the *Escherichia coli* gab cluster: nucleotide sequence of the structural genes gabD and gabP and expression of the GABA permease gene," *Arch. Microbiol.* 160:454-460 (1993).

"1,4 butanediol/THF," *Nextant ChemSystems Reports* Jan. 23, 2004.

Niu et al., "Benzene-free synthesis of adipic acid," *Biotechnology Progress* 18:201-211 (2002).

Oliver et al., "Determination of the nucleotide sequence for the glutamate synthase structural genes of *Escherichia coli* K-12," *Gene* 60:1-11 (1987).

Park et al., "Aerobic regulation of the sucABCD genes of *Escherichia coli*, which encode alpha-ketoglutarate dehydrogenase and succinyl coenzyme A synthetase: roles of ArcA, Fnr, and the upstream sdhCDAB promoter," *J. Bacteriol.* 179:4138-4142 (1997).

Park et al., "Isolation and characterization of recombinant mitochondrial 4-aminobutyrate aminotransferase," *J. Biol. Chem.* 268:7636-7639 (1993).

Pelanda et al., "glutamate synthase genes of the diazotroph *Azospirillum brasillense*. Cloning, sequencing, and analysis of functional domains," *J. Biol. Chem.* 268:3099-3106 (1993).

Pharkya et al., "Exploring the overproduction of amino acids using the bilevel optimization framework OptKnock," *Biotechnol. Bioeng.* 84(7):887-899 (2003).

Poirier et al., "Polyhydroxybutyrate, a Biodegradable Thermoplastic Produced in Transgenic Plants," *Science* 256:520-523 (1992).

Presecan et al., "the *Bacillus subtillis* genome from gerBC (311 degrees) to licR (334 degrees)," *Microbiology* 143:3313-3328 (1997).

Price et al., "Genome-scale models of microbial cells: evaluating the consequences of constraints," *Nat. Rev. Microbiol.* 2:886-897 (2004).

Qiu et al., "Metabolic engineering for the production of copolyesters consisting of 3-hydroxybutyrate and 3-hydroxyhexanoate by *Aeromonas hydrophila*," *Macromol Biosci.* 4(3):255-261 (2004).

Radhakrishnan et al., "Applications of metabolic modeling to drive bioprocess development for the production of value-added chemicals," *Biotechnol Bioprocess. Eng.* 10:408-417 (2005).

Ramos et al., "Mutations affecting the enzymes involved in the utilization of 4-aminobutyric acid as nitrogen source by the yeast *Saccharomyces cerevisiae*," *Eur. J. Biochem.* 149:401-404 (1985).

Redenbach et al., "A set of ordered cosmids and a detailed genetic and physical map for the 8 Mb *Streptomyces coelicolor* A3(2) chromosome," *Mol. Microbiol.* 21:77-96 (1996).

Reed et al., An expanded genome-scale model of *Escherichia coli* K-12 (iJR904 GSM/GPR), *Genome Biol.* 4(9):R54 (2003).

Reitzer, L.J. "Ammonia Assimillation and the Biosynthesis of Glutamine, Glutamate, Aspartate, Asparagine, I-Alanine, and d-Alanine," in *Escherichia coli and Salmonella*, (Neidhardt, ed.), pp. 391-407, ASM Press: Washington, D.C., 1996.

Ribeiro et al., "Microbial reduction of α-acetyl-γ-butyrolactone," *Tetrahedron* 17:984-988 (2006).

Riondet et al., "Measurement of the intracellular pH in *Escherichia coli* with the internally conjugated fluorescent probe 5- (and 6-)carboxyfluorescein succinimidyl ester," *Biotechnology Tech.* 11:735-738 (1997).

Saito and Doi, "Microbial synthesis and properties of poly(3-hydroxybutyrate-co-4-hydroxybutyrate) in *Comamonas acidovorans*," *Int. J. Biol. Macromol.* 16:99-104 (1994).

Saito et al., "Microbial Synthesis and properties of Poly(3-hydroxybutyrate-co-4-hydroxybutyrate)," *Polym. Int.* 39:169-174 (1996).

Sakakibara et al., "Isolation and characterization of a cDNA that encodes maize glutamate dehydrogenase," *Plant Cell Physiol.* 36:789-797 (1995).

Sanchez et al., "Properties and functions of two succinic-semialdehyde dehydrogenases from *Pseudomonas putida*," *Biochim Biophys Acta* 953(3):249-257 (1988).

Sanchez et al., "Purification and properties of two succinic semialdehyde dehydrogenases from *Klebsiella pneumoniae*," *Biochim Biophys Acta.* 990(3):225-231 (1989).

Scherf et al., "Purification and properties of 4-hydroxybutyrate coenzyme A transferase from *Clostridium aminobutyricum*," *Appl Environ Microbiol.* 57(9):2699-2702 (1991).

Scherf et al., "Suffinate-ethanol fermentation in *Clostridium kluyveri*: purification and characterisation of 4-hydroxybutyryl-CoA dehydratase/vinylacetyl-CoA delta 3-delta 2-isomerase," *Arch. Microbiol.* 161:239-245 (1994).

Schilling et al., "Combining pathway analysis with flux balance analysis for the comprehensive study of metabolic systems," *Biotech Bioeng*, 71:286-306 (2000).

Schilling et al., "Toward metabolic phenomics: analysis of genomic data using flux balances," *Biotech Prog.* 15:288-295 (1999).

Schilling et al., "Theory for the systemic definition of metabolic pathways and their use in interpreting metabolic function from a pathway-oriented perspective," *J. Theor. Biol.* 203:229-248 (2000).

Schneider et al., "The *Escherichia coli* gabDTPC operon: specific gamma-aminobutyrate catabolism and nonspecific induction," *J. Bacteriol.* 184:6976-6986 (2002).

Shigeoka and Nakano, "Characterization and molecular properties of 2-oxoglutarate decarboxylase from *Euglena gracilis*," *Arch Biochem. Biophys.* 288:22-28 (1991).

Shigeoka and Nakano, "The effect of thiamin on the activation of thiamin pyrophosphate-dependent 2-oxoglutarate decarboxylase in *Euglena gracilis*," *J. Biochem.* 292 (Pt. 2):463-467 (1993).

Shigeoka et al., "Effect of L-glutamate on 2-oxoglutarate decarboxylase in *Euglena gracilis*," *Biochem. J.* 282 (Pt. 2):319-323 (1992).

Shiraki et al., "Fermentative production of (R)-(-)-(3) hydroxybutyrate using 3-hydroxybutyrate dehydrogenase null mutant of *Ralstonia eutropha* and recombinant *Escherichia coli*," *J. Biosci. Bioeng.* 102(6):529-534 (2006).

Skinner and Cooper, "An *Escherichia coli* mutant defective in the NAD-dependent succinate semialdehyde dehydrogenase," *Arch Microbiol.* 132(3):270-275 (1982).

Smith et al., "Complete genome sequence of Methanobacterium thermoautotrophicum deltaH: functional analysis and comparative genomics," *J. Bacteriol.* 179:7135-7155 (1997).

Snedecor et al., "Selection, expression, and nucleotide sequencing of the glutamate dehydrogenase gene of *Peptostreptococcus asaccharolyticus*," *J. Bacteriol.* 173:6162-6167 (1991).

Sohling and Gottschalk, "Purification and characterization of a coenzyme-A-dependent succinate-semialdehyde dehydrogenase from *Clostridium kluyveri*." *Eur. J. Biochem.* 212:121-127 (1993).

Sohling and Gottschalk, "Molecular analysis of the anaerobic succinate degradation pathway in *Clostridium kluyveri*," *J. Bacteriol.* 178:871-880 (1996).

Song et al., "Construction of recombinant *Escherichia coli* strains producing poly (4-hydroxybutyric acid) homopolyester from glucose," *Wei Sheng Wu Xue Bao*, 45(3):382-386 (2005).

Spencer and Guest, "Transcription analysis of the sucAB, aceEF and lpd genes of *Escherichia coli*," *Mol. Gen. Genetics* 200:145-154 (1985).

Spencer et al., "Nucleotide sequence of the sucB gene encoding the dihydrolipoamide succinyltransferase of *Escherichia coli* K12 and homology with the corresponding acetyltransferase," *Eur J Biochem.* 141(2):361-374 (1984).

Steinbuchel and Schlegel, "Physiology and molecular genetics of poly(beta-hydroxy-alkanoic acid) synthesis in *Alcaligenes eutrophus*," *Mol. Microbiol.* 5(3):535-542 (1991).

Steinbuchel and Valentin, "Diversity of bacterial polyhydroxyalkanoic acids," *FEMS Microbiol. Lett.* 128:219-228 (1995).

Steinbuchel and Wiese, et al., "A Pseudomonas strain accumulating polyesters of 3-hydroxybutyric acid and medium-chain-length 3-hydroxyalkanoic acids," *Appl. Microbiol. Biotechnol.* 37:691-697 (1992).

Syntichaki et al., "The amino-acid sequence similarity of plant glutamate dehydrogenase to the extremophilic archaeal enzyme conforms to its stress-related function," *Gene* 168:87-92 (1996).

Teller et al., "The glutamate dehydrogenase gene of *Clostridium symbiosum*, Cloning by polymerase chain reaction sequence analysis and over-expression in *Escherichia coli*," *Eur. J. Biochem.* 206:151-159 (1992).

Thakur et al., "Changes in the Electroencephalographic and .gamma.-Aminobutyric Acid Transaminsase and Succinic Semialdehyde Dehydrogenase in the Allergen Induced Rat Brain," *Biochem. Int.* 16:235-243 (1998).

Tomb et al., "The complete genome sequence of the gastric pathogen *Helicobacter pylori*," *Nature* 388:539 (1997).

Toth et al., "The ald gene, encoding a coenzyme A-acylating aldehyde dehydrogenase, distinguishes *Clostridium beijerinckii* and two other solvent-producing clostridia from *Clostridium acetobutylicum*," *Appl. Environ. Microbiol.* 65(11):4973-4980 (1999).

Tzimagiorgis et al., "Molecular cloning, structure and expression analysis of a full-length mouse brain glutamate dehydrogenase cDNA," *Biochem. Biophys. Acta* 1980:250-253 (1991).

Tzimagiorgis, et al., "Structure and expression analysis of a member of the human glutamate dehydrogenase (GLUD) gene gamily mapped to chromosome 10phh.2," *Hum. Genet.* 91:433-438 (1993).

Umeda et al., "Cloning and sequence analysis of the poly(3-hydroxyalkanoic acid)-synthesis genes of *Pseudomonas acidophila*," *Appl Biochem Biotechnol.* 70-72:341-352 (1998).

Valentin et al., "Poly(3-hydroxybutyrate-co-4-hydroxybutyrate) formation from gamma-aminobutyrate and glutamate," *Biotechnol. Bioeng.* 67(3):291-299 (2000).

Valentin et al., "Metabolic pathway for biosynthesis of poly(3-hydroxybutyrate-co-4-hydroxybutyrate) from 4-hydroxybutyrate by *Alcaligenes eutrophus*," *Eur. J. Biochem.* 227:43-60 (1995).

Valentin et al., "Identification of 4-hydroxyvaleric acid as a constituent of biosynthetic polyhydroxyalkanoic acids from bacteria," *Appl. Microbiol. Biotechnol.* 36:507-514 (1992).

Valentin et al., "Identification of 5-hydroxyhexanoic acid, 4-hydroxyheptanoic acid and 4-hydroxyoctanoic acid as new constituents of bacterial polyhydroxyalkanoic acids," *Appl. Microbiol. Biotechnol.* 46:261-267 (1996).

Valentin et al., "Indentification of 4-hydroxyhexanoic acid as a new constituent of biosynthetic polyhydroxyalkanoic acids from bacteria," *Appl. Microbiol. Biotechnol.* 40:710-716 (1994).

Valentin et al., "Production of poly(3-hydroxybutyrate-co-4-hydroxybutyrate) in recombinant *Escherichia coli* grown on glucose," *J. Biotechnol.* 58:33-38 (1997).

Valle et al., "Complete nucleotide sequence of the glutamate dehydrogenase gene from *Escherichia coli* K-12," *Gene* 27:193-199 (1984).

Valle et al., "Nucleotide sequence of the promotor and amino-terminal coding region of the glutamate dehydrogenase structural gene of *Escherichia coli*," *Gene* 23:199-209 (1983).

Van der Rest et al., "Functions of the membrane-associated and cytoplasmic malate dehydrogenases in the citric acid cycle of *Escherichia coli*," *J. Bacteriol.* 182(24):6892-6899 (2000).

Vanrolleghem et al., "Validation of a metabolic network for *Saccharomyces cerevisiae* using mixed substrate studies," *Biotech Prog.* 12:434-448 (1996).

Varma and Palsson, "Stoichiometric flux balance models quantitatively predict growth and metabolic by-product secretion in wild-type *Escherichia coli* W3110," *Appl. Environ. Microbiol.* 60:3724-3731 (1994).

Walter et al., "Molecular characterization of two *Clostridium acetobutylicum* ATCC 824 butanol dehydrogenase isozyme genes," *J Bacteriol.* 174(22):7149-7158 (1992).

Wang et al., "Isolation of poly-3-hydroxybutyrate metabolism genes from complex microbial communities by phenotypic complementation of bacterial mutants," *Appl. Environ. Microbiol.* 72(1):384-391 (2006).

Willadsen and Buckel, "Assay of 4-hydroxybutyryl-CoA dehydrasate from *Clostridium aminobutyricum*," FEMS Microbiol. Lett. 58:187-192 (1990).

Williams et al., "Biodegradable plastics from plants," CHEMTECH 26:38-44 (1996).

Wolff and Kenealy, "Purification and characterization of the oxygen-sensitive 4-hydroxybutanoate dehydrogenase from *Clostridium kluyveri*," *Protein Expr. Purif.* 6:206-212 (1995).

Wolff et al., "Dehydrogenases involved in the conversion of succinate to 4-hydroxybutanoate by *Clostridium kluyven*," *Appl. Environ. Microbiol.* 59:1876-1882 (1993).

Yee et al., "Isolation and characterization of a NADP-dependent glutamate dehydrogenase gene from the primitive eucaryote *Giardia lamblia*," *J. Biol. Chem.* 267:7539-7544 (1992).

Yu et al., "sucAB and sucCD are mutually essential genes in *Escherichia coli*," *FEMS Microbiol. Lett.* 254(2):245-250 (2006).

Zhang et al., "Kinetic and mechanistic characterization of the polyhydroxybutyrate synthase from *Ralstonia eutropha*," *Biomacromolecules*, 1(2):244-251 (2000).

Zhou et al., "Functional replacement of the *Escherichia coli* D-(−)-lactate dehydrogenase gene (ldhA) with the L-(+)-lactate dehydrogenase gene (ldhL) from *Pediococcus acidilactici*," *Applied and Environ. Micro.* 69:2237-2244 (2003).

Cukalovic et al., "Feasibility of production method for succinic acid derivatives: a marriage of renewable resources and chemical technology," *Biofuels Bioprod. Bioref.* 2:505-529 (2008).

Feist et al., "The growing scope of applications of genome-scale metabolic reconstructions using *Escherichia coli*," *Nat. Biotechnol.* 26(6):659-667 (2008).

McKinlay et al., "Prospects for a bio-based succinate industry," *Appl. Microbiol. Biotechnol.* 76(4):727-740 (2007).

Okino et al., "An efficient succinic acid production process in a metabolically engineered *Corynebacterium glutamicum* strain," *Appl. Microbiol. Biotechnol.* 81(3):459-464 (2008).

Takigawa et al., "Probabilistic path ranking based on adjacent pairwise coexpression for metabolic transcripts analysis," *Bioinformatics* 24(2):250-257 (2008).

Wang et al., "Screening microorganisms for utilization of furfural and possible intermediates in its degradative pathway," *Biotechnol. Lett.* 16(9):977-982 (1994).

Aberhart and Hsu, "Stereospecific hydrogen loss in the conversion of [2H7]isobutyrate to beta-hydroxyisobutyrate in *Pseudomonas putida*. The stereochemistry of beta-hydroxyisobutyrate dehydrogenase," *J. Chem. Soc.* [Perkin1], 6:1404-1406 (1979).

Abiki et al., "Localization of NAD-isocitrate dehydrogenase and glutamate dehydrogenase in rice roots: candidates for providing carbon skeletons to NADH-glutamate synthase," *Plant Cell Physiol.* 46(10):1724-1734 (2005).

Adams and Kletzin, Oxidoreductase-type enzymes and redox proteins involved in fermentative metablisms of hyperthermophilic archaea, *Archae Adv. Protein Chem.* 48:101-180 (1996).

Aevarsson et al., "Crystal structure of2-oxoisovalerate and dehydrogenase and the architecture of 2-oxo acid dehydrogenase multienzyme complexes," *Nat. Struct. Biol.* 6:785-792 (1999).

Ahmed and Lewis, "Fermentation of biomass-generated synthesis gas: effects of nitric oxide," *Biotechnol. Bioeng.* 97:1080-1086 (2007).

Ahrens et al., "Enzymatic evidence for an involvement of pyruvate dehydrogenase in the anaerobic glycerol metabolism of *Klebsiella pneumoniae*," *J. Biotechnol.* 56:135-142 (1997).

Akhtar and Jones, "Construction of a synthetic YdbK-dependent pyruvate:H2 pathway in *Escherichia coli* BL21(DE3)," *Metabolic Eng.* 11:139-147 (2009).

Alber et al., "Malonyl-coenzyme A reductase in the modified 3-hydroxypropionate cycle for autotrophic carbon fixation in archaeal Metallosphaera and Sulfolobus spp," *J. Bacteriol.* 188:8551-8559 (2006).

Alberty et al., "Biochemical thermodynamics," *Biochim. Biophys. Acta.* 1207:1-11 (1994).

Alhapel et al., "Molecular and functional analysis of nicotinate catabolism in *Eubacterium barkeri*," *Proc. Natl. Acad. Sci. USA* 103(33)12341-12346 (2006).

Andersen and Hansen, "Cloning of the lysA gene from *Mycobacterium tuberculosis*," *Gene* 124:105-109 (1993).

Andersen et al., "A gene duplication led to specialized gamma-aminobutyrate and beta-alaine aminotransferase in yeast," *FEBS J.* 274(7):1804-1817 (2007).

Andreesen and Ljungdahl, "Formate dehydrogenase of Clostridium thermoaceticum: incorporation of selenium-75, and the effects of selenite, molybdate, and tungstate on the enzyme," *J. Bacteriol.* 116:867-873 (1973).

Aneja and Charles, "Poly-3-hydroxybutyrate degradation in *Rhizobium* (*Sinorhizobium*) *meliloti*: isolation and characterization of a gene encoding 3-hydroxybutryate dehydrogenase," *J. Bacteriol.* 181(3):849-857 (1999).

Angrand et al., "Simplified generation of targeting constructs using ET recombination," *Nucleic Acids Res.* 27:e16. (1999).

Ansorge and Kula, "Production of Recombinant L-Leucine Dehydrogenase from *Bacillus cereus* in Pilot Scale Using the Runaway Replication System *E. coli*[pIET98]," *Biotechnol. Bioeng.* 68-557-562 (2000).

Aoshima and Igarashi, "A novel biotin protein required for reductive carboxylation of 2-oxoglutarate by isocitrate dehydrogenase in *Hydrogenobacter thermophilus* TK-6," *Mol. Microbiol.* 51(3):791-798 (2004).

Aoshima and Igarshi, "Nondecarboxylating and decarboxylating isocitrate dehydrogenases: oxalosuccinate reductas as an ancestral form of isocitrate dehydrogenase," *J. Bacteriol.* 190(6):2050-2055 (2008).

Aoshima et al., "A novel enzyme, citryl-CoA lyase, catalysing the second step of the citrate cleavage reaction in *Hydrogenobacter thermophilus* TK-6," *Mol. Microbiol.* 52(3):763-770 (2004).

Aoshima et al., "A novel enzyme, citryl-CoA synthetase, catalysing the first step of the citrate cleavage reaction in *Hydrogenobacter thermophilus* TK-6," *Mol. Microbiol.* 52(3):751-756 (2004).

Aoshima et al., "A novel oxalosuccinate-forming enzyme involved in the reductive carboxylation of 2-oxoglutarate in *Hydrogenobacter thermophilus* TK-6," *Mol. Microbiol.* 62(3):748-759 (2006).

Aoshima, "Novel enzyme reactions related to the tricarboxylic acid cycle: phylogenetic/functional implications and biotechnological applications," *Appl. Microbiol. Biotechnol.* 75(2):249-255 (2007).

Aragon and Lowenstein, "A survey of enzymes which generate or use acetoacetyl thioesters in rat liver," *J. Biol. Chem.* 258(8):4725-4733 (1983).

Arikawa et al., "Soluble fumarate reductase isoenzymes from *Saccharomyces cerevisiae* are required for anaerobic growth," *FEMS Microbiol. Lett.* 165:111-116 (1998).

Arps et al., "Genetics of Serine Pathway Enzymes in *Methylobacterium extorquens* AM1: Phosphoenolpyruvate Carboxylase and Malyl Coenzyme A Lyase," *J. Bacteriol.* 174(12):3776-3783 (1993).

Asano and Kato, "Crystalline 3-methylaspartase from a facultative anaerobe, *Escherichia coli* strain YG1002," *FEMS Microbiol. Lett.* 118(3):255-258 (1994).

Asano et al., "Alteration of substrate specificity of aspartase by directed evolution," *Biomol. Eng.* 22:95-101 (2005).

Asuncion et al., "Overexpression, purification, crystallization and data collection of 3-methylaspartase from *Clostridium tetanomorphum*," *Acta Crystallogr.D. Biol. Crystallogr.* 57:731-733 (2001).

Asuncion et al., "The Structure of 3-Methylaspartase from *Clostridium tetanomorphum* Functions via the Common Enolase Chemical Step," *J. Biol. Chem.* 277(10):8306-8311 (2002).

Atsumi et al., "Non-fermentative pathways for synthesis of branched-chain higher alcohols as biofuels," *Nature* 451:86-89 (2008).

Baba et al., "Construction of *Escherichia coli* K-12 in-frame, single-gene knockout mutants: the Keio collection," *Mol. Syst. Biol.* 2006. 0008 (2006).

Baker and van der Drift, "Purification and properties of L-erythro-3,5-diaminohexanoate dehydrogenase from *Clostridium sticklandii*," *Biochemistry* 13(2):292-299 (1974).

Baker et al., "Purification and prpoerties of L-erythro-3,5-diaminohexanoate dehydrogenase from a lysine-fermenting *Clostirdium*," *J. Biol. Chem.* 247(23):7724-7734 (1972).

Barker et al., "Butyryl-CoA:acetoacetate CoA-transferase from a lysine-fermenting *Clostridium*," *J. Biol. Chem.* 253(4):1219-1225 (1978).

Barker et al., "Pathway of Lysine Degradation in *Fusobacterium nucleatum*," *J. Bacteriol.* 152(1):201-207 (1982).

Barrick et al., "Quantitative analysis of ribosome binding sites in *E.coli*," *Nucleic Acids Res.* 22:1287-1295 (1994).

Barrowman et al., "Immunological comparison of microbial TPP-dependent non-oxidative alpha-keto acid decarboxylase," *FEMS Microbiology Lett.* 34:57-60 (1986).

Barthelmebs et al., "Expression of *Escherichia coli* of Native and Chimeric Phenolic Acid Decarboxylases with Modified Enzymatic activites and Method for Scrreening recombinant *E. coli* Strains Expressing These Enzymes," *Appl. Environ. Microbiol.* 67:1063-1069 (2001).

Berg et al., "A 3-Hydroxypropionate/4-Hydroxybutyrate Autotrophic Carbon Dioxide Assimilation Pathway in Archaea," *Science* 318:1782-1786 (2007).

Bergquist and Gibbs, "Degenerate oligonucleotide gene shuffling," *Methods Mol. Biol.* 325:191-204 (2007).

Bergquist et al., "Degenerate oligonucleotide gene shuffling (DOGS) and random drift mutagenesis (RNDM): two complementary techniques for enzyme evolution," *Biomol. Eng.* 63-72 (2005).

Berkovitch et al., "A locking mechanism preventing radical damage in the absence of substrate, as revealed by the x-ray structure of lysine 5,6-aminomutase," *Proc. Natl. Acad. Sci. USA* 101:15870-15875 (2004).

Biellmann et al., "Aspartate-beta-semialdehyde dehydrogenase from *Escherichia coli*. Purification and general properties," *Eur. J. Biochem.* 104(1):53-58 (1980).

Binstock and Shulz, "Fatty acid oxidation complex from *Escherichia coli*," *Methods. Enzymo.* 71 (Pt C):403-411 (1981).

Bisswanger, "Substrate Specificity of the Pyruvate Dehydrogenase Complex from *Escherichi coli*," *J. Biol. Chem.* 256(2):815-822 (1981).

Blanco et al., "Critical catalytic functional groups in the mechanims of aspartate-β-semialdehyde dehydrogenase," *Acta Crystallogr. D. Biol. Crystallogr.* 60:1808-1815 (2004).

Blanco et al., "The role of substrate-binding roups in the mechanism of asparte-β-semialdehyde dehydrogenase," *Acta Crystallogr. D. Biol. Crystallog.* 60:1388-1395 (2004).

Blaschkowsk et al., "Routes of flavodoxin and ferredoxin reduction in *Escherichia coli*. CoA-acylating pyruvate: flavodoxin and NADPH: flavodoxin oxidoreductases participating in the activation of pyruvate formate-lyase," *Eur.J Biochem.* 123:563-569 (1982).

Boles et al., "Characterization of a glucose-repressed pyruvate kinase (Pyk2p) in *Saccharomyces cerevisiae* that is catalytically insensitive to fructose-1,6-bisphosphate," *J. Bacteriol.* 179:2987-2993 (1997).
Bonnarme et al., "Itaconate biosynthesis in *Aspergillus terreus*," *J. Bacteriol.* 177(12):3573-3578 (1995).
Bonner and Bloch, "Purification and Properties of Fatty Acyl Thiesterase I from *Escherichia coli*," *J. Biol. Chem.* 247(10)3123-3133 (1972).
Bose et al., "Genetic analysis of the methanol- and methylamine-specific methyltransferase 2 genes of *Methanosarcina acetivorans* C2A," *J. Bacteriol.* 190:4017-4026 (2008).
Botting et al., "Substrate Specificity of the 3-Methylaspartate Ammonia-Lyase Reaction: Observation of Differential Relative Reaction rates for Substrate-Product Pairs," *Biochemistry* 27:2953-2955 (1988).
Bower et al., "Cloning, Sequencing, and Characterization of the *Bacillus subtilis* Biotin Biosynthetic Operon," *J. Bacteriol.* 178(14):4122-4130 (1996).
Boynton et al., "Cloning, sequencing, and expression of clustered genes encoding beta-hydroxybutyryl-coenzyme A (CoA) dehydrogenase, crotonase, and butyryl-CoA dehydrogenase from *Clostridium acetobutylicum* ATCC 824," *J. Bateriol.* 178(11):3015-3024 (1996).
Branlant and Branlant, "Nucleotide sequence of the *Escherichia coli* gap gene. Differente evolutionay behaviour of the Nad+-binding domain and of the catalytic domain of D-glyceraldehyde-3-phosphate dehydrogenase," *Eur. J. Biochem.* 150(1):61-66 (1985).
Brasen and Schonheit, "Unusual ADP-forming acetyl-coenzyme A synthetases from the mesophilic halophilic eurarchaeon Haloarcula marismortui and from the hyperthermophilic crenarchaeon *Pyrobaculum aerophilum*," *Arch. Microbiol.* 182:277-287 (2004).
Bravo et al., "Reliable, sensitive, rapid and quantitative enzyme-based assay for gamma-hydroxybutyric acid (GHB)," *J. Forensic Sci.* 49:379-387 (2004).
Bredwell et al., "Reactor Design Issues for Synthesis-Gas Fermentations," *Biotechnol Prog.* 15:834-844 (1999).
Breitkreuz et al., "A novel gamma-hydroxybutyrate dehydrogenase: identification and expression of an *Arabidopsis* cDNA and potential role under oxygen deficiency," *J. Biol. Chem.* 278:41552-41556 (2003).
Bremer, "Pyruvate Dehydrogenase, Substrate Specificity and Product Inhibition," *Eur. J. Biochem.* 8:535-540 (1969).
Brosch et al., "Genome plasticity of BCG and impact on vaccine efficacy," *Proc. Natl. Acad. Sci. USA* 104(13):5596-5601 (2007).
Bu et al., "Two human glutamate decarboxylases, 65-kDa GAD and 67-kDa GAD, are each encoded by a single gene," *Proc. Natl. Acad. Sci. USA* 89(6):2115-2119 (1992).
Buckel et al., "Glutaconate CoA-Transferase from *Acidaminococcus fermentans*," *Eur. J. Biochem.* 118:315-321 (1981).
Burke et al, "The Isolation, Characterization, and Sequence of the Pyruvate Kinase Gene of *Saccharomyces cerevisiae*," *J. Biol. Chem.* 258(4):2193-2201 (1983).
Buu et al., "Functional Characterization and Localization of Acetyl-CoA Hydrolase, Ach1p, in *Saccharomyces cerevisiae*," *J. Biol. Chem.* 278(19):17203-17209 (2003).
Campbell et al., "A new *Escherichia coli* metabolic competency: growth on fatty acis by a novel anaerobic β-oxidation pathway," *Mol. Microbiol.* 47(3):793-805 (2003).
Cary et al., "Cloning and expression of *Clostridium acetobutylicum* ATCC 824 acetoacetyl-coenzyme A:acetate/butyrate:coenzyme A-transferase in *Escherichia coli*," *Appl. Environ. Micrpbiol.* 56(6):1576-1583 (1990).
Cary et al., "Cloning and expression of *Clostridium acetobutylicum* phosphotransbutyrylase and butyrate kinase genes in *Escherichia coli*," *J. Bacteriol.* 170(10):4613-4618 (1988).
Caspi et al., "MetaCyc: a multiorganism database of metabolic pathways and enzymes," *Nucleic Acids Res.* 34(Database issue):D511-D516 (2006).
Cha and Parks, "Succinic Thiokinase. I. Purification of the Enzyme from Pig Heart," *J. Biol. Chem.* 239:1961-1967 (1964).
Chandra et al., "Pyruvate decarboxylase: a key enzyme for the oxidative metabolism of lactic acid by *Acetobacter pasteruianus*," *Arch. Microbiol.* 176:443-451 (2001).

Chen et al., "A novel lysine 2,3-aminomutase encoded by the yodO gene of *Bacillus subtilis*: characterization and the observation of organic radical intermediates," *Biochem. J.* 348:539-549 (2000).
Chen et al., "Cloning, Sequencing, Heterologous Expression, Purification, and Characterization of Adenosylcobalamin-dependent D-Ornithine Aminomutase from *Clostridium sticklandii*," *J. Biol. Chem.* 275:44744-44750 (2001).
Chicco et al., "Regulation of Gene Expression of Branched-chain Keto Acid Dehydrogenase Complex in Primary Cultured Hepatocytes by Dexamethasone and cAMP Analog," *J. Biol. Chem.* 269(30):19427-19434 (1994).
Chirpich et al., "Lysine 2,3-Aminomutase," *J. Biol. Chem.* 245(7):1778-1789 (1970).
Cho et al., "Critical residues for the coenzyme specificity of NAD+-deptendent 15-hydroxyprostaglandin dehydrogenase," *Arch. Biochem. Biophys.* 419(2): 139-146 (2003).
Chowdhury et al., "Cloning and Overexpression of the 3-Hydroxyisobutyrate Dehydrogenase Gene from *Pseudomonas putida* E23," *Biosci. Biotechnol. Biochem.* 67(2):438-441 (2003).
Chowdhury et al., "3-Hydroxyisobutyrate dehydrogenase from *Pseudomonas putida* E23: purification and characterization," *Biosci. Biotechno.l Biochem.* 60(12):2043-2047 (1996).
Christenson et al., "Kinetic analysis of the 4-methylideneimidazole-5-one-containing tyrosine aminomutase in enediyne antitumor antibiotic C-1027 biosynthesis," *Biochemistry* 42(43):12708-12718 (2003).
Clark and Ljungdahl, "Purification and properties of 5,10-methylenetetrahydrofolate reductase from *Clostridium formicoaceticum*," *Methods Enzymol.* 122:392-399 (1986).
Clark and Ljungdahl, "Purification and properties of 5,10-methylenetetrahydrofolate reductase, an iron-sulfur flavoprotein from *Clostridium formicoaceticum*," *J. Biol. Chem.* 259:10845-10849 (1984).
Clarke et al., "Rational construction of a 2-hydroxyacid dehydrogenase with new substrate specificity," *Biochem. Biophys. Res. Commun.* 148:15-23 (1987).
Clausen et al., "PAD1 encodes phenylacrylic acid decarboxylase which confers resistance to cinnamic acid in *Saccharomyces cerevisiae*," *Gene* 142:107-112 (1994).
Coco et al., "DNA shuffling method for generating highly recombined genes and evolved enzymes," *Nat. Biotechnol.* 19(4):354-359 (2001).
Colby and Chen, "Purification and properties of 3-Hydroxybutyryl-Coenzyme A Dehydrogenase from *Clostridium beijerinckii* (*Clostridium butylicum*:) NRRL B593," *Appl. Environ. Microbiol.* 58:3297-3302 (1992).
Cooper, "Glutamate-gamma-aminobutyrate transaminase," *Methods Enzymol.* 113:80-82 (1985).
Corthesy-Theulaz et al., "Cloning and characterization of *Helicobacter pylori* succinyl CoA:acetoacetate CoA-transferase, a novel prokaryotic member of the CoA-transferase family," *J. Biol. Chem.* 272(41):25659-25667 (1997).
Cunningham et al., "Transcriptional regulation of the aconitase genes (acnA and acnB) of *Escherichia coli*," *Microbiology* 143(Pt 12):3795-3805 (1997).
D'Ari and Rabinowitz, "Purification, characterization, cloning, and amino acid sequence of the bifunctional enzyme 5,10-methylenetetrahydrofolate dehydrogenase/5,10-methenyltetrahydrofolate cyclohydrolase from *Escherichia coli*," *J. Biol. Chem.* 266:23953-23958 (1991).
Das et al, "Characterization of a corrinoid protein involved in the C1 metabolism of strict anaerobic bacterium *Moorella thermoacetica*," *Proteins* 67:167-176 (2007).
Datar et al., "Fermentation of biomass-generated producer gas to ethanol," *Biotechnol. Bioeng.* 86:587-594 (2004).
Davie et al., "Expression and Assembly of a Functional E1 Component (α2β2) of Mammalian Branched-Chain α-Ketoacid Dehydrogenase Complex in *Escherichia coli*," *J. Biol. Chem.* 267:16601-16606 (1992).
De Biase et al., "Isolation, overexpression, and biochemical characterization of the two isoforms of glutamic acid decarboxylase from *Escherichia coli*," *Protein Expr. Purif.* 8:430-438 (1996).

de Bok et al., "Two W-containing formate dehydrogenases (CO2-reductases) involved in syntrophic propionate oxidation by *Syntrophobacter fumaroxidans*," *Eur. J. Biochem.* 270:2476-2485 (2003).

de la Torre et al., "Identification and functional analysis of prokaryotic-type aspartate aminotransferase: implications for plant amino acid metabolism," *Plant J.* 46(3):414-425 (2006).

de Mata and Rabinowitz, "Formyl-methenyl-methylenetetrahydrofolate synthetase(combined) from yeast. Biochemical characterization of the protein from an ade3 mutant lacking the formyltetrahydrofolate synthetase function," *J. Biol. Chem.* 255:2569-2577 (1980).

Deana, "Substrate specificity of a dicarboxyl-CoA: dicarboxylic acid coenzyme A transferase from rat liver mitochondria," *Biochem. Int.* 26(4):767-773 (1992).

Diao et al., "Crystal Structure of Butyrate Kinase 2 from *Thermotoga maritima*, a Member of the ASKHA Superfamily of Phosphotransferases," *J. Bacteriol* 191(8):2521-2529 (2009).

Diao et al., "Crystallization of butyrate kinase 2 from *Thermotoga maritima* medicated by varpor diffusion of acetic acid," *Acta Crystallogr. D. Crystallogr.* 59:1100-1102 (2003).

Diaz et al., "Gene cloning, heterologous overexpression and optimized refolding of the NAD-glutamate dehydrogenase from haloferax mediterranei," *Extremophiles* 10(2):105-115 (2006).

Diderichsen et al., "Cloning of aldB, which encodes alpha-acetolactate decarboxylase, an exoenzyme from *Bacillus brevis*," *J. Bacteriol.* 172(8):4315-4321 (1990).

Do et al., "Engineering *Escherichia coli* for fermentative dihydrogen production: potential role of NADH-ferredoxin oxidoreductase from the hydrogenosome of anaerobic protozoa," *Appl. Biochem. Biotechnol.* 153:21-33 (2009).

Dobbek et al., "Crystal structure of a carbon monoxide dehydrogenase reveals a [Ni-4Fe-5S] cluster," *Science* 293:1281-1285 (2001).

DOE Report, "Top Value-Added Chemicals from Biomass," 2004.

Doyle et al., "Structural basis for a change in substrate specificity: crystal structure of S113E isocitrate dehydrogenase in a complex with isopropylmalate, Mg2+, and NADP," *Biochemistry* 40(14):4234-4241 (2001).

Drake and Daniel, "Physiology of the thermophilic acetogen *Moorella thermoacetica*," *Res. Microbiol.* 155:869-883 (2004).

Drake, "Demonstration of hydrogenase in extracts of the homoacetate-fermenting bacterium *Clostridium thermoaceticum*," *J. Bacteriol.* 150:702-709 (1982).

Drewke et al., "r-O-Phosphoryl-L-threonine, a substrate of the pdxC(serC) gene product involved in vitamin $B_6$ biosynthesis," *FEBS Lett.* 390:179-182 (1996).

Duncan et al., "Acetate utilization and butyryl coenzyme A (CoA):acetate-CoA transferase in butyrate-producing bacteria from the human large intestine," *Appl. Environ. Microbiol.* 68(10):5186-5190 (2002).

Dürre et al., "Solventogenic enzymes of *Clostridium acetobutylicum*: catalytic properties, genetic organization, and transcriptional regulation," *FEMS Microbiol. Rev.*17(3):251-262 (1995).

Edwards and Palsson, "The *Escherichia coli* MG1655 in silico Metabolic Genotype: Its Definition, Characteristics, and Capabilities," *Proc. Natl. Acad. Sci. USA*, 97(10):5528-5533 (2000).

Edwards et al., "In Silico Predictions of *Escherichia coli* metabolic capabilities are Consistent with Experimental Data," *Nat. Biotechnol.* 19(2):125-130 (2001).

Efe et al., "Options for biochemical production of 4-hydroxybutyrate and its lactone as a substitute for petrochemical production," *Biotechnol. Bioeng.* 99:1392-1406 (2008).

Eikmanns et al., "The phosphoenolpyruvate carboxylase gene of *Corynebacterium glutamicum*: molecular cloning, nucleotide sequence, and expression," *Mol. Gen. Genet.* 218:330-339 (1989).

Ekiel et al., "Acetate and CO2 assimilation by Methanothrix concilii," *J. Bacteriol.* 162(3):905-908 (1985).

Enomoto et al., "Cloning and sequencing of the gene encoding the soluble fumarate reductase from *Saccharomyces cerevisiae*," *DNA Res.* 3:263-267 (1996).

Estevez et al., "X-ray crystallographic and kinetic correlation of a clinically observed human fumarase mutation," *Protein Sci.* 11:1552-1557 (2002).

Evans et al., "A new ferredoxin-dependent carbon reduction cycle in a photosynthetic bacterium," *Proc. Natl. Acad. Sci. USA* 55(4):928-934 (1966).

Faehnle et al., "A New Branch in the Family: Structure of Aspartate-β-semialdehyde dehydrogenase from *Methanococcus jannashii*," *J. Mol. Biol.* 353:1055-1068 (2005).

Fernandez-Valverde et al., "Purification of *Pseudomonas putida* Acyl coenzyme a Ligase Active with a Range of Aliphatic and Aromatic Substrates," *Appl. Environ. Microbiol.* 59:1149-1154 (1993).

Fischer and Sauer, "Metabolic flux profiling of *Escherichi coli* mutants in central carbon metabolism using GC-MS," *Eur. J. Biochem.* 270(5)880-891 (2003).

Fishbein and Bessman, "Purification and properties of an enzyme in human blood and rat liver microsomes catalyzing the formation and hydrolysis of gamma-lactones. I. Tissue localization, stoichiometry, specificity, distinction from esterase," *J. Biol. Chem.* 241(21):4835-4841 (1966).

Fontaine et al., "A New Type of Glucose Fermentation by *Clostridium thermoaceticum*," *J. Bacteriol.* 43:701-715 (1942).

Fontaine et al., "Molecular characterization and transcriptional analysis of adhE2, the gene encoding the NADH-dependent aldehyde/alcohol dehydrogenase responsible for butanol production in alcohologenic cultures of *Clostridium acetobutylicum* ATCC 824," *J. Bacteriol.* 184:821-830 (2002).

Ford, et al., "Molecular properties of the lys1+ gene and the regulation of alpha-aminoadipate reductase in *Schizosaccharomyces pombe*," *Curr. Genet.* 28(2):131-137 (1995).

Fox et al, "Characterization of the region encoding the CO-induced hydrogenase of *Rhodospirillum rubrum*," *J. Bacteriol.* 178:6200-6208 (1996).

Friedrich et al., "The complete stereochemistry of the enzymatic dehydration of 4-hydroxybutyryl coenzyme A to crotonyl coenzyme A," *Angew. Chem. Int. Ed. Engl.* 47:3254-3257 (2008).

Fries et al., "Reaction Mechanism of the Heteroameric ($\alpha_2\beta_2$) E1 Component of 2-Oxo Acid Dehydrogenase Multienzyme Complexes," *Biochemistry* 42:6996-7002 (2003).

Fujii et al., "Characterization of L-lysine 6-aminotransferase and its structural gene from *Favobacterium lutescens* IFO3084," *J. Biochem.* 128(3):391-397 (2000).

Fujii et al., "Error-prone rolling circle amplification: the simplest random mutagenesis protocol," *Nat. Protoc.* 1(5):2493-2497 (2006).

Fujii et al., "One-step random mutagenesis by error-prone rolling circle amplification," *Nucleic Acids Res.* 23(19):e145 (2004).

Fujita et al., "Novel Substrate Specificity of designer3-Isopropylmalate Dehydrogenase Derived from *Thermus thermophilus* HB1," *Biosci. Biotechnol. Biochem.* 65(12):2695-2700 (2001).

Fukao et al., "Succinyl-coA:3-Ketoacid CoA Transferase (SCOT): Cloning of the Human SCOT Gene, Tertiary Structural Modeling of the Human SCOT Monomer, and Characterization of Three Pathogenic Mutations," *Genomics* 68:144-151 (2000).

Fukuda and Wakagi, "Substrate recognition by 2-oxoacid:ferredoxin oxidoreductase from *Sulfolobus* sp. Strain 7," *Biochim. Biophys.* Acta 1597:74-80 (2002).

Fukuda et al., "Role of a highly conserved YPITP motif in 2-oxoacid:ferredoxin oxidoreductase," *Eur. J. Biochem.* 268:5639-5646 (2001).

Furdui and Ragsdale, "The role of pyruvate ferredoxin oxidoreductase in pyruvate synthesis during autotrophic growth by the Wood-Ljungdahl pathway," *J. Biol. Chem.* 275:28494-28499 (2000).

Galagan et al., "The genome of *M. acetivorans* reveals extensive metabolic and physiological diversity," *Genome Res.* 12:532-542 (2002).

Gangloff et al., "Molecular cloning of the Yeast Mitochondrial Aconitase Gene (ACO1) and Evidence of a Synergistic Regulation of Expression by Glucose plus Glutamate," *Mol. Cell. Biol.* 10(7):3551-3561 (1990).

Gay et al., "Cloning Structural Gene sacB, Which codes for Exoenzyme Levansucrase of *Bacillus subtilis*: Epxresion of the Gene in *Escherichia coli*," *J. Bacteriol*. 153:1424-1431 (1983).

Gerhardt et al., "Fermentation of 4-aminobutyrate by *Clostridium aminobutyricum*: cloning of two genes involved in the formation and dehydration of 4-hydroxybutyryl-CoA," *Arch.Microbiol*. 174:189-199 (2000).

Gibbs et al., "Degenerate oligonucleotide gene shuffling (DOGS): a method for enhancing the frequency of recombination with family shuffling," *Gene*. 271:13-20 (2001).

Gibson and McAlister-Henn, "Physical and Genetic Interactions of Cytosolic Malate Dehydrogenase with Other Gluconeogenic Enzymes," *J. Biol. Chem*. 278(28):25628-25636 (2003).

Giesel and Simon, "On the occurrence of enoate reductase and 2-oxo-carboxylate reductase in clostridia and some observations on the amino acid fermentation by *Peptostreptococcus anaerobius*," *Arch. Microbiol*. 135(1):51-57 (1983).

Goda et al., "Cloning, Sequencing, and Expression in *Escherichia coli* of the *Clostridium tetanomorphum* Gene Encoding δ-Methylaspartase and Characterization of the Recombinant Protein," *Biochemistry* 31:10747-10756 (1992).

Gong et al., "Effects of transport properites of ion-exchange membranes on desalination of 1,3-propanediol fermentation broth by electrodialysis," *Desalination* 191:1-3, 193-199 (2006).

Gong et al., "Specificity Determinants for the Pyruvate Dehydrogenase Component Reaction Mapped with Mutated and Prosthetic Group Modified Lipoyl Domains," *J. Biol. Chem*. 275(18):13645-13653 (2000).

Gonzalez and Robb, "Genetic analysis of *Carboxydothermus hydrogenoformans* carbon monoxide dehydrogenase genes cooF and cooS," *FEMS Microbiol. Lett*. 191:243-247 (2000).

Goupil et al., "Imbalance of leucine flux in *Lactoccus lactis* and its use for the isolation of diacetyl-overproducing strains," *Appl. Environ, Microbiol*. 62(7):2636-2640 (1996).

Goupil-Feuillerat et al., "Transcriptional and translational regulation of alpha-acetolactate decarboxylase of *Lactococcus lactis* subsp. *lactis*," *J. Bacteriol*. 182(19):5399-5408 (2000).

Green et al., "Catabolism of α-Ketoglutarate by a sucA Mutant of *Bradyrhizobium japonicum*: Evidence for an Alternative Tricarboxylic Acid Cycle," *J. Bacteriol*. 182(10):2838-2844 (2000).

Grubbs, "Olefin Metathesis," *Tetrahedron*, 60:7117-7140 (2004).

Guirard and Snell, "Purification and properties of ornithine decarboxylase from *Lactobacillus* sp. 30a," *J. Biol. Chem*. 255(12):5960-5964 (1980).

Guo et al., "Posttranslational activation, site-directed mutation and phylogenetic analyses of lysine biosynthesis enzymes alpha-aminoadipate reductase Lys1P (AARO and the phosphopantetheinyl transferase Lys7p (PPTase) from *Schizosaccharomyces pombe*," *Yeast* 21(15):1279-1288 (2004).

Guo et al., "Site-directed mutational analysis of the novel catalytic domains of alpha-aminoadipate reductase (Lys2p) from *Candida albicans*," *Mol. Genet. Genomics* 269:271-279 (2003).

Gutierrez et al., "The fumarase genes of *Escherichia coli*: location of the fumB gene and discovery of a new gene (fumC)," *J. Gen. Microbiol*. 131:2971-2984 (1985).

Hadfield et al., "Active site analysis of the potential antimicrobial target aspartate semialdehyde dehydrogenase," *Biochemistry* 40(48):14475-14483 (2001).

Hadfield et al., "Structure of aspartate-beta-semialdehyde dehydrogenase from *Escherichia coli*, a key enzyme in the aspartate family of amino acid biosynthesis," *J. Mol. Biol*. 289(4):991-1002 (1999).

Hagemeier et al., "Insight into the mechanism of biological methanol activation based on the crystal structure of the methanol-cobalamin methyltransferase complex," *Proc. Natl. Acad. Sc.i USA* 103:18917-18922 (2006).

Hammer and Bode, "Purification and characterization of an inducible L-lysine:2-oxoglutarate 6-aminostransferase from *Dandida utilis*," *J. Basic Microbiol*. 32:21-27 (1992).

Hanai et al., "Engineered synthetic pathway for isopropanol production in *Escherichia coli*," *Appl. Environ. Microbiol*. 73:7814-7818 (2007).

Hansford, "Control of mitochondrial substrate oxidation," *Curr. Top. Bioenerg*. 10:271-278 (1980).

Harms and Thauer, "Methylcobalamin: coenzyme M methyltransferase isoenzymes MtaA and MtbA from *Methanosarcina barkeri*. Cloning, sequencing and differential transcription of the encoding genes, and functional overexpression of the mtaA gene in *Escherichia coli*," *Eur. J. Biochem*. 235:653-659 (1996).

Hasegawa et al., "Transcriptional regulation of ketone body-utilizing enzyme, acetoacetyl-CoA synthetase, by C/EBPα during adipocyte differentiation," *Biochim. Biophys. Acta* 1779:414-419 (2008).

Haselbeck and McAlister-Henn, "Isolation, nucleotide sequence, and disruption of the *Saccharomyces cerevisiae* gene encoding mitochondrial NADP(H)-specific isocitrate dehydrogenase," *J. Biol. Chem*. 266(4):2339-2345 (1991).

Hashidoko et al., "Cloning of a DNA Fragment Carrying the 4-Hydroxycinnamate Decarboxylase (*pofK*) Gene from *Klebsiella oxtoca*, and Its Constitutive Expression in *Escherichia coli* JM109 Cells," *Biosci. Biotech. Biochem*. 217-218 (1994).

Hashimoto et al., "Activation of L-Lysine ε-Dehydrogenase from *Agrobacterium tumefaciens* by Several Amino Acids and Monocarboxylates," *J. Biochem*. 106:76-80 (1989).

Hasson et al., "The Crystal Structure of Benzoylformate Decarboxylase at 1.6 Å Resolution: Diversity of Catalytic Residues in thiamin Diphosphate-Dependent Enzymes," *Biochemistry* 37:9918-9930 (1998).

Hawes et al., "Mammalian 3-hydroxyisobutyrate dehydrogenase," *Methods Enzymol*. 324:218-228 (2000).

Hayden et al., "Glutamate dehydrogenase of *Halobacterium salinarum*: evidence that the gene sequence currently assigned to the NADP+-dependent enzyme is in fact that of the NAD+-dependent glutamate dehydrogenase," *FEMS Microbiol. Lett*. 211:37-41 (2002).

Hayes et al., "Combining computational and experimental screening for rapid optimization of protein properties," *Proc. Natl. Acad. Sci. USA* 99(25):15926-15931 (2002).

Henning et al., "Identification of Novel enzoylformate Decarboxlyases by Growth Selection," *App. Environ. Microbiol*. 72(12)7510-7517 (2006).

Hermann et al., "Energy conservation via electron-transferring flavoprotein in anaerobic bacteria," *J. Bacteriol*. 190(3):784-791 (2007).

Hermes et al., "Searching sequence space by definably random mutagenesis: Improving the catalytic potency of an enzyme," *Proc. Natl. Acad. Sci. USA* 87:696-700 (1990).

Herrmann et al., "Two beta-alanyl-CoA:ammonia lyases in *Clostridium propionicum*," *FEBS J*. 272:813-821 (2005).

Hesslinger et al., "Novel keto acid formate-lyase and propionate kinase enzymes are components of an anaerobic pathway in *Escherichia coli* that degrades L-threonine to propionate," *Mol. Microbiol* 27:477-492 (1998).

Hester et al., "Purification of active E1 alpha 2 beta 2 of *Pseudomonas putida* branched-chain-oxoacid dehydrogenase," *Eur. J. Biochem*. 233(3):828-836 (1995).

Heydari et al., "Highly Stable L-Lysine 6-Dehydrogenase from the Thermophile *Geobacillus stearothemophilus* Isolated from a Japanese Hot Spring: Characterization, gene Cloning and Sequencing, and Expression," *Appl. Environ. Microbiol*. 70:937-942 (2004).

Hibbert et al. "Directed evolution of biocatalytic processes," *Biomol. Eng*. 22:11-19 (2005).

Hijarrubia et al., "Domain Structure characterization of the Multifunctional α-Aminoadipate Reductase from *Penicillium chrysogenum* by Limited Proteolysis," *J. Biol. Chem*. 278:8250-8256 (2003).

Hillmer and Gottschalk, Solubilization and partial characterization of particulate dehydrogenases from *Clostridium kluyver, Biochim. Biophys. Acta* 3334:12-23 (1974).

Hirano et al., "Purification and Characterization of the alcohol dehydrogenase with a broad substrate specificity originated from 2-phenylethanol-assimilating *Brevibacterium* sp. KU 1390," *J. Biosci. Bioeng*. 100(3):318-322 (2005).

Hiser et al., "ERG10 from *Saccharomyces cerevisiae* encodes acetoacetyl-CoA thiolase," *J. Biol. Chem*. 269:31383-31389 (1994).

Hoffmeister et al., "Mitochondrial trans-2-enoyl-CoA reductase of wax ester fermentation from *Euglena gracilis* defines a new family of enzymes involved in lipid synthesis," *J. Biol. Chem.* 280:4329-4338 (2005).

Hogan et al., "Improved specificity toward substrates with ositively charged side chains by site-directed mutagenesis of the L-lactate dehydrogenase of *Bacillus stearothermophilus*," *Biochemistry* 34(13):4225-4230 (1995).

Hong and Lee, "Enhanced Production of Succinic Acid by Metabolically Engineered *Escherichia coli* with Amplified Activities of Malic Enzyme and Fumarase," *Biotechnol. Bioprocess Eng.* 9:252-255 (2004).

Horswill and Escalante_Semerena, "In vitro conversion of propionate to pyruvate by *Salmonella enterica* enzymes: 2-methylcitrate dehydratase (PrpD) and aconitas Enzymes catalyze the conversion of 2-methylcitrate to 2-methylisocitrate," Biochemistry 40(15):4703-4713 (2001).

Huang et al., "Identification and Characterization of a Second Butyrate Kinase from *Clostridium acetobutylicum* ATCC 824," *J. Mol. Microbiol. Biotechnol.* 2(1):33-38 (2000).

Huang et al., "Purification and Characterization of a Ferulic Acid Decarboxylase from *Pseudomonas fluorescens*," *J. Bacteriol.* 176(19):5912-5918 (1994).

Hugler et al., "Autotrophic CO2 fixation via the reductive tricarboxylic acid cycle in different lineages within the phylum Aquificae: evidence for two ways of citrate cleavage," *Environ. Microbiol.* 9:81-92 (2007).

Hugler et al., "Evidence for autotrophic Co2 fixation via the reductive tricarboxylic acid cycle by members of the epsilon subedivision of proteobacteria," *J. Bacteriol.* 187(9):3020-3027 (2005).

Huo and Viola, "Substrate specificity and identification of functional groups of homoserine kinase from *Escherichia col*," *Biochemistry* 35(50):16180-16185 (1996).

Ichikawa et al. Catalytic reaction of 1,3-butanediol over solid acids, *J. Mol. Catalysis A Chem.* 256:106-112 (2006).

Ichikawa et al., "PIO study on 1,3-butanediol dehydration over CeO2 (1 1 1) surface," *J. Mol. Catalysis A Chem.* 231:181-189 (2005).

Iffland et al., "Directed molecular evolution of cytochrome c peroxidase," *Biochemistry* 39(25):10790-10798 (2000).

Ikai and Yamamoto, "Identification and Analysis of a Gene Enclding L-2,4-Diaminobutyrate:2-Ketoglutarate 4-Aminotransferase Invloved in the 1,3-Diaminopropane Production Pathway in Acinetobacter baumanni," *J. Bacteriol.* 179(16):5118-5125 (1997).

Ingoldsby et al., "The discovery of four distinct glutamate dehydrogenase genes ina strain of *Halobacterium salinarum*," Gene 349:237-244 (2005).

Ishige et al., "Wax ester production from n-alkanes by *Acinetobacter* sp. strain M-1: ultrastructure of cellular inclusions and role of acyl coenzyme A reductase," *Appl. Environ. Microbiol.* 68(3):1192-1195 (2002).

Ismaiel et al., "Purification and characterization of a primary-secondary alcohol dehydrogenase from two strains of *Clostridium beijerinckii*," *J. Bacteriol.* 175(16):5097-5105 (1993).

Ismail et al., "Functional genomics by NMR spectroscopy Phenylacetate catabolism in *Escherichia coli*," *Eur. J. Biochem.* 270:3047-3054 (2003).

Ito et al., "D-3-hydroxybutyrate dehydrogenase from *Pseudomonas fragi*: molecular cloning of the enzyme gene and crystal structure of the enzyme," *J. Mol. Biol.* 355(4):722-733 (2006).

Iverson et al., "Structure of the *Escherichia coli* fumarate reductase respiratory complex," *Science* 284(5422):1961-1966 (1999).

Jacobi et al., "The hyp operon gene products are required for the maturation of catalytically active hydrogenase isoenzymes in *Escherichia coli*," *Arch. Microbiol.* 158:444-451 (1992).

Jeon et al., "Heterologous expression of the alcohol dehydrogenase (adhI) gene from *Geobacillus thermoglucosidasius* strain M10EXG," *J. Biotechnol.* 135:127-133 (2008).

Jiang et al., "De novo computational design of retro-aldol enzymes," *Science* 319(5868):1387-1391 (2008).

Johnson et al., "Alteration of a single amino acid changes the substrate specificity of dihydroflavonol 4-reductase," *Plant J.* 25(3):325-333 (2001).

Jojima et al., "Production of isopropanol by metabolically engineered *Escherichia coli*," *Appl. Microbiol. Biotechnol.* 77:1219-1224 (2008).

Jones and Woods,"Acetone-butanol fermentation revisited," *Microbiol. Rev.* 50(4):484-524 (1986).

Kai et al., "*Phosphoenolpyruvate carboxylase*: three-dimensional structure and molecular mechanisms," *Arch. Biochem. Biophys.* 414:170-179 (2003).

Kanao et al., "Characterization of isocitrate dehydrogenase from the green sulfur bacterium *Chlorbium limicola*. A carbon dioxide-fixing enzyme in the reductive tricarboxylic acid cycle," *Eur. J. Biochem.* 269(7):1926-1931 (2002).

Kanao et al., "Kinetic and biochemical analyses on the reaction mechanism of a bacterial ATP-citrate lyase," *Eur. J. Biochem.* 269(14):3049-3416 (2002).

Kapatral et al., "Genome Sequence and Analysis of the Oral Bacterium *Fusobacterium nucleatum* Strain ATCC 25586," *J. Bacteriol.* 184(7):2005-2018 (2002).

Kazahaya et al, "Aerobic Dissimilation of Glucose by Heterolactic Bacteria," *J. Gen. Appl. Microbiol.* 18(1):43-55 (1972).

Kellum and Drake, "Effects of cultivation gas phase on hydrogenase of the acetogen *Clostridium thermoaceticum*," *J. Bacteriol.* 160:466-469 (1984).

Keng and Viola, "Specificity of Aspartokinase III from *Escherichia coli* and an Examination of Important Catalytic Residues," *Arch. Biochem. Biophys.* 335:73-81 (1996).

Kessler et al., "Pyruvate-formate-lyase-deactivase and acetyl-CoA reductase activities of *Escherichia coli* reside on a polymeric protein particle encoded by adhE," *FEBS.Lett.* 281:59-63 (1991).

Khan et al., "Molecular properties and enhancement of thermostability by random mutagenesis of glutamate ehydrogenase from *Bacillus subtilis*," *Biosci. Biotechnol. Biochem.* 69(10):1861-1870 (2005).

Killenberg-Jabs et al., "Active oligomeric states of pyruvate decarboxylase and their functional characterization," *Eur. J. Biochem.* 268:1698-1704 (2001).

Kim and Tabita, "Both subunits of ATP-citrate lyase from *Chlorobium tepidum* contribute to catalytic activity," *J. Bacteriol.* 188(18):6544-6552 (2006).

Kim et al., "Construction of an *Escherichia coli* K-12 mutant for homoethanologenic fermentation of glucose or xylose without foreign genes," *Appl. Environ. Microbiol.* 73:1766-1771 (2007).

Kim et al., "Dihydrolipoamide Dehydrogenase Mutation Alters the NADH Sensitivity of Pyruvate Dehydrogenase Complex of *Escherichia coli* K-12," *J. Bacteriol.* 3851-3858 (2008).

Kim, "Purification and Propertis of a mine α-Ketoglutarate Transaminase from *Escherichia coli*," *J. Biol. Chem.* 239:783-786 (1964).

Kino et al., "Synthesis of DL-tryptophan by modified broad specificity amino acid racemase from *Pseudomonas putida* IFO 12996," *Appl. Microbiol. Biotechnol.* 73(6):1299-1305 (2007).

Kinoshita, "Purification of two alcohol dehydrogenases from *Zymomonas mobilis* and their properties," *Appl. Microbiol. Biotechnol.* 22:249-254 (1985).

Klasson et al., Biological conversion of coal and coal-derived synthesis gas. *Fuel.* 72:1673-1678 (1993).

Klatt et al., "Comparative genomics provides evidence for the 3-hydroxypropionate autotrophic pathway in filamentous anoxygenic phototrophic bacteria and in hot spring microbial mats," *Environ. Microbiol.* 9(8):2067-2078 (2007).

Knapp et al., "Crystal Structure of the Truncated Cubic Core Component of the *Escherichia coli* 2-Oxoglutarate Dehydrogenase Multienzyme Complex," *J. Mol. Biol.* 289:655-668 (1998).

Knappe and Sawers, A radical-chemical route to acetyl-CoA: the anaerobically induced pyruvate formate-lyase system of *Escherichia coli*, FEMS Microbiol. Rev. 4:383-398 (1990).

Kobayashi et al., "Physiochemical, Catalytic, and Immunochemical Properties of Fumarases Crystallized Separately from Mitochondrial and Cytosolic Fractions of Rat Liver," *J. Biochem.* 89:1923-1931 (1981).

Koland and Gennis, "Proximity of rreactive cysteine residue and flavin in *Escherichia coli* pyruvate oxidase as estimated by fluorescence energy transfer," *Biochemistry* 21(18):4438-4442 (1982).

Koo et al., "Cloning and characterization of the bifunctional alcohol/acetaldehyde dehydrogenase gene (adhE) in *Leuconostoc mesenteroides* isolated from kimchi," *Biotechnol. Lett.* 27(7):505-510 (2005).

Korbert et al., "Crystallization of the NADP+-dependent Glutamate Dehydrogenase from *Escherichia coli*," *J. Mol. Biol.* 234:1270-1273 (1993).

Korolev et al., "Autotracing of *Escherichia coli* acetate CoA-transferase α-subunit structure using 3.4 Å MAD and 1.9 Å native data," *Acta. Crystallog. D. Biol. Crystallogr.* 58:2116-2121 (2002).

Kort et al., "Glutamate dehydrogenase from the hyperthermophilic bacterium *Thermotoga maritima*: molecular characterization and phylogenetic implications," *Extremophiles* 1:52-60 (1997).

Kosaka et al., "Characterization of the sol operon in butanol-hyperproducing *Clostridium saccharoperbutylacetonicum* strain N1-4 and its degeneration mechanism," *Biosci. Biotechnol. Biochem.* 71:58-68 (2007).

Kosjek et al., "Purification and characterization of a chemotolerant alcohol dehydrogenase applicable to coupled redox reactions," *Biotechnol. Bioeng.* 86(1):55-62 (2004).

Kreimeyer et al., "Indentification of the Last Unknown Genes in the fermentation Pathway of Lysine," *J. Biol. Chem.* 282:7191-7197 (2007).

Kretz et al., "Gene site saturation mutagenesis: a comprehensive mutagenesis approach," *Methods Enzymol.* 388:3-11 (2004).

Krieger et al., "Pyruvate decarboxylase from *Kluyveromyces lactis* An enzyme with an extraordinary substrate activation behaviour," *Eur. J. Biochem.* 269:3256-3263 (2002).

Kumamaru et al., "Enhanced degradation of polychlorinated biphenyls by directed evolution of biphenyl dioxgenase," *Nat. Biotechnol.* 16(7)663-666 (1998).

Kumari et al., "Cloning, Characterization, and Functional Expression of acs, the Gene Which Encodes Acetyl Coenzyme A Synthetase in *Escherichia coli*," *J. Bacteriol.* 177(10): 2878-2886 (1995).

Kurihara et al., "A Novel Putrescine Utilization Pathway Involves γ-Glutamylated Intermediates of *Escherichia coli* K-12," *J. Biol. Chem.* 280(6) 4602-4608 (2005).

Kuznetsova et al., "Enzyme genomics: Application of general enzymatic screens to discover new enzymes," *FEMS Microbiol. Rev.* 29:263-279 (2005).

Kwok and Hanson, "GFP-labelled Rubisco and aspartate aminotransferase are present in plastid stromules and traffice between plastids," *J. Experi. Bot.* 55:(397)595-604 (2004).

Laivenieks et al., "Cloning sequencing, and overexpression of the *Anaerobiospirillum succinicproducens* phosphoenolpyruvate carboxykinase (pckA) gene," *Appl. Environ. Microbiol.* 63:2273-2280 (1997).

Lam and Winkler, "Metabolic Relationships between Pyridoxine (vitamin $B_6$) and Serine Biosynthesis in *Escherichia coli* K-12," *J. Bacteriol.* 172(11):6518-6528 (1990).

Lamas-Maceiras et al., "Amplification and disruption of the phenylacetyl-CoA ligase gene of *Penicillium chrysogenum* encoding an aryl-capping enzyme that supplies phenylacetic acid to the isopenicillin N-acyltransferase," *Biochem. J.* 395:147-155 (2006).

Lamed and Zeikus, "Novel NAP-linked alcohol-aldehyde/ketone oxidoreductase in thermophilic ethanologenic bacteria," *Biochem. J.* 195:183-190 (1981).

Lebbink et al., "Engineering activity and stability of *Thermotogo maritima* Glutamate Dydrogenase. I. Introduction of a Six-residue Ion-pair Network in the Hinge Region," *J. Mol. Biol.* 280:287-296 (1998).

Lebbink et al., "Engineering activity of *Thermotogomaritima* glutamate dehydrogenase. II: construction of a 16-residue ion-pair network at the subunit interface," *J. Mol. Biol.* 289(2):357-369 (1999).

Leduc et al., "The Hotdog Thiesterase EntH (YbdB) Plays a Role in Vivo in Optimal Enterobactin biosynthesis by Interacting with the ArCP Domain of EntB," *J. Bacteriol.* 189(19):7112-7126 (2007).

Lee and Cho, "Identification of essential active-site residues in ornithine decarboxylase of *Nicotiana glutinosa* decarboxylating both L-ornithine and L-lysine," *Biochem. J.* 360(Pt 3):657-665 (2001).

Lee et al., "Biosynthesis of enantiopure (s)-3-hydroxybutyric acid in metabolically engineered *Escherichia coli*," *Appl. Microbiol. Biotechnol.* 79(4):633-641 (2008).

Lee et al., "Cloning and Characterization of *Mannheimia succiniciproducens* MBEL55E Phosphoenolpyruvate Carboxykinase (pckA) Gene," *Biotechnol. Bioprocess Eng.* 7:95-99 (2002).

Lee et al., "Phylogenetic diversity and the structural basis of substrate specificity in the beta/alpha-barrel fold basic amino acid decarboxylases," *J. Biol. Chem.* 282(37):27115-27125 (2007).

Lee et al., "A new approach to directed gene evolution by recombined extension on truncated templates (RETT)," *J. Molec. Catalysis* 26:119-129 (2003).

Lemonnier and Lane, "Expression of the second lysine decarboxylase gene of *Escherichia coli*," *Microbiology* 144(Pt 3):751-760 (1998).

Lepore et al., "The x-ray crystal structure of lysine-2,3-aminomutase from *Clostridium subterminale*," *Proc. Natl. Acad. Sci. USA* 102:13819-13824 (2005).

Lessner et al., "An unconventional pathway for reduction of $CO_2$ to methane in CO-grown *Methanosarcina acetivorans* revealed by proteomics," *Proc. Natl. Acad. Sci. USA* 103:17921-17926 (2006).

Li et al., "Properties of Nicotinamide Adenine Dinucleotide Phosphate-Dependent Formate Dehydrogenase from *Clostridium thermoaceticum*," *J.Bacteriol.* 92:405-412 (1966).

Liam and Whitman, "Sterochemical and Isotopic Labeling Studies of 4-Oxalocrotonate Decarboxylase and Vinylpyruvate Hydratase: Analysis and Mechanistic Implications," *J. Am. Chem. Soc.* 116:10403-10411 (1994).

Lin et al., "Fed-batch culture of a metabolically engineered *Escherichia coli* strain designed for high-level succinate production and yield under aerobic conditions," *Biotechnol. Bioeng.* 90(6):775-779 (2005).

Lin et al., "Functional expression of horseradish peroxidase in *E. coli* by directed evolution," *Biotechnol. Prog.* 15(3):467-471 (1999).

Lingen et al., "Alteration of the Substrate Specificity of Benzoylformate Decarboxylase from *Pseudomonas putida* by Directed Evolution," *Chembiochem* 4:721-726 (2003).

Lingen et al., "Improving the carboligase activity of benzoylformate decarboxylase from *Pseudomonas putida* by a combination of directed evolution and site-directed mutagenesis," *Protein Eng.* 15:585-593 (2002).

Link et al., "Methods for generating precise deletions and insertions in the genome of wild-type *Escherichia coli*: application to open reading frame characterization," *J. Bacteriol.* 179:6228-6237 (1997).

Liu et al., "Crystal Structures of Unbound and Aminoxyacetate-Bound *Escheriha coli* Y-Aminobutyrate Aminotransferase," *Biochem.* 43:10896-10905 (2004).

Liu et al., "Kinetic and crystallographic analysis of active site mutants of *Escherichia coli* gamma-aminobutyrate aminotransferase," *Biochemistry* 44:(8):2982-2992 (2005).

Ljungdahl and Andreesen, "Formate dehydrogenase, a selenium—tungsten enzyme from *Clostridium thermoaceticum*," *Methods Enzymol.* 53:360-372 (1978).

Ljungdahl et al., "Tungsten, a component of active formate dehydrogenase from *Clostridium thermoacetium*," *FEBS Lett.* 54:279-282 (1975).

Lokanath et al., "Crystal Structure of novel NADP-dependent 3-Hydroxyisobutyrate Dehydrogenase from *Thermus thermophilus* HB8," *J. Mol Biol.* 352:905-917 (2005).

Louie and Chan, "cloning and characterization of the gamma-glutamyl phosphate reductase gene of *Campylobacter jejuni*," *Mol. Gen. Genet.* 240:29-35 (1993).

Louis et al., "Restricted Distribution of the Butyrate Kinase Pathway among Butyrate-Producing Bacteria from the Human Colon," *J. Bacteriol.* 186(7):2099-2106 (2004).

Lovell et al., "Cloning and expression in *Escherichia coli* of the *Clostridium thermoaceticum* gene encoding thermostable formyltetrahydrofolate synthetase," *Arch. Microbiol.* 149:280-285 (1988).

Lovell et al., "Primary structure of the thermostable formyltetrahydrofolate synthetase from *Clostridium thermoaceticum*." *Biochemistry* 29:5687-5694 (1990).

Low et al., "Mimicking somatic hypermutation: affinity maturation of antibodies displayed on baceriophage using a bacterial mutator strain," *J. Mol. Biol.* 260(3):359-368 (1996).

Lu et al, "Functional analysis and regulation of the divergent spuABCDEFG-spuI operons for polyamine uptake and utilization in *Pseudomonas aeruginosa* PA01," *J. Bacteriol.* 184:3765-3773 (2002).

Lu et al., "Sequence and expression of the gene encoding the corrinoid/iron-sulfur protein from *Clostridium thermoaceticum* and reconstitution of the recombinant protein to full activity," *J. Biol. Chem.* 268:5605-5614 (1993).

Lutz and Bujard, "Independent and tight regulation of transcriptional units in *Escherichia coli* via the LacR/O, the TetR/O and AraC/I1-I2 regulatory elements," *Nucleic Acids Res.* 25:1203-1210 (1997).

Lutz et al., "Creating multiple-crossover DNA libraries independent of sequence identity," *Proc. Natl. Acad. Sci USA* 98:11248-11253 (2001).

Lutz et al., "Rapid generation of incremental truncation Iibraries for protein engineering using alpha-phosphothioate nucleotides," *Nucleic Acids Res.* 15:29(4):E16 (2001).

Ma et al., "Induced Rebuilding of Aspartase Confromation," *Ann. N.Y. Acad. Sci.* 672:60-65 (1992).

Mack and Buckel, "Conversion of glutaconate CoA-transferase from *Acidaminococcus fermentas* into an acyl-CoA hydrolase by site-directed mutagenesis," *FEBS Lett.* 405:209-212 (1997).

Mack et al., "Location of the two genes encoding glutaconate coenzyme A-transferase at the beginning of the hydroxyglutarate operon in *Acidaminococcus fermentans*," *Eur. J. Biochem.* 226:41-51 (1994).

Maeder et al., "The *Methanosarcina barkeri* genome: comparative analysis with *Methanosarcina acetivorans* and *Methanosarcina mazei* reveals extensive rearrangement within methanosarcinal genomes," *J. Bacteriol.* 188:7922-7931 (2006).

Mahadevan et al., "Application of metabolic modeling to drive bioprocess development for the production of value-added chemicals," *Biotechnol. Bioprocess Eng.* 10(5):408-417 (2005).

Mahan and Csonka, "Genetic analysis of the proBA genes of *Salmonella typhimurium*: physical and genetic analyses of the cloned proB+ A+ genes of *Escherichia coli* and of a mutant allele that confers proline overproduction and enhanced osmotolerance," *J. Bacteriol.* 156(3):1249-1262 (1983).

Manning and Pollitt, "Tracer studies of the interconversion of R- and S-methylmalonic semialdehydes in man," *Biochem. J.* 231:481-484 (1985).

Marco-Marin et al., "Site-directed Mutagenesis of *Escherichia coli* Acetylglutamate Kinase and Aspartokinase III Probes the Catalytic and Substrate-binding Mechanisms of these Amino Acid Kinase Family Enzymes and Allows Three-dimensional Modelling of Aspartokinase," *J. Mol. Biol.* 334:459-476 (2003).

Marks et al., "Molecular Cloning and Characterization of (R)-3-Hydroxybutyrate Dehydrogenase from Human Heart," *J. Biol. Chem.* 267:15459-15463 (1992).

Martin et al., "Engineering a mevalonate pathway in *Escherichia coli* for production of terpenoids," *Nat. Biotechnol.* 21:796-802 (2003).

Martinez-Blanco et al., "Purification and Biochemical Characterization of Phenylacetyl-CoA Ligase from *Pseudomonas putida*," *J. Biol. Chem.* 265(12):7084-7090 (1990).

Mattevi et al., "Atomic structure of the cubic core of the pyruvate dehydrogenase multienzyme complex," *Science* 255:5051):1544-1550 (1992).

Matthies and Schink, "Reciprocal Isomerization of Butyrate and Isobutyrate by the Strictly Anaerobic Bacterium Strain WoG13 and Methanogenic Isobutyrate Degradation by a Devined Triculture," *Appl. Environ. Microbiol.* 58(5):1435-1439 (1992).

McPherson and Wootton, "Complete nucleotide sequence of the *Escherichia coli* gdhA gene," *Nucleic Acids Res.* 11(15):5257-5266 (1983).

Melchiorsen et al., "The level of pyruvate-formate lyase controls the shift from homolactic to mixed-acid product formation in *Lactoccus lactis*," *Appl. Microbiol. Biotechnol.* 58(3):338-344 (2002).

Meng and Chuang, "Site-Directed Mutagenesis and functional Analysis of the Active-Site Residues of the E2 Component of Bovine Branched-Chain $\alpha$-Keto Acid Dehydrogenase Complex," *Biochem.* 33:12879-12885 (1994).

Menon and Ragsdale, "Mechanism of the *Clostridium thermoaceticum* pyruvate:ferredoxin oxidoreductase: evidence for the common catalytic intermediacy of the hydroxyethylthiamine pyropyrosphate radical," *Biochemistry* 36:8484-8494 (1997).

Menzel et al., "Kinetic, dynamic, and pathway studies of glycerol metabolism by *Klebsiella pneumoniae* in anaerobic continuous culsutre: IV. Enzymes and fluxes of pyruvate metabolism," *Botechnol. Bioeng.* 60(5):617-626 (1998).

Metz et al., "Purification of a jojoba expression of its cDNA in high erucic embryo fatty acyl-coenzyme a reductase and acid rapeseed," *Plant Physiol.* 122(3):635-644 (2000).

Minard and McAlister-Henn, "Isolation, Nucleotide Sequence Analysis, and Disruption of theMDH2 Gene from *Saccharomyces cerevisiae*: Evidence for Three Isozymes of Yeast Malate Dehydrogenase," *Mol. Cell. Biol.* 11(1):370-380 (1991).

Misono and Nagasaki, "Occurrence of L-Lysine $\epsilon$-Dehydrogenase in *Agrobacterium tumefaciens*," *J. Bacteriol.* 150(1):398-401 (1982).

Miyazaki et al., "alpha-aminoadipate aminotransferase from an extremely thermophilic bacterium, *Thermus thermophilus*," *Microbiology* 150(Pt 7):2327-2334 (2004).

Mizobata et al., "Purification and Characterization of a thermostable Class II Fumarase from *Thermus thermophilus*," *Arch. Biochem. Biophys.* 355:49-55 (1998).

Momany et al., "Crystallographic Structures of a PLP-Dependent Ornithine Decarboxylase from Lactobacillus 30a to 3.0 Å Resolution," *J. Mol. Biol.* 242:643-655 (1995).

Monnet et al., "Regulation of branched-chain amino acid biosynthesis by alpha-acetolactate decarboxylase in *Streptococcus thermophilus*," *Lett. Appl. Microbiol.* 36(6):399-405 (2003).

Moore et al., "Expression and Purification of Aspartate $\beta$-Semialdehyde Dehydrogenase from Infectious Microorganisms," *Protein Expr. Purif.* 25:189-194 (2002).

Morris et al., "Nucleotide sequence of the LYS2 gene of *Saccharomyces cerevisiae*: homology to *Bacillus brevis* tyrocidine synthetase1," *Gene* 98:141-145 (1991).

Morton et al., Cloning, sequencing, and expression of genes encoding enzymes of the autotrophic acetyl-CoA pathway in the acetogen *Clostridium thermoaceticum*., p. 389-406 In M. Sebald (ed.), Genetics and molecular biology of anaerobic bacteria. Springer Verlag, New York (1992).

Morton et al., "The primary structure of the subunits of carbon monoxide dehydrogenase/acetyl-CoA synthase from *Clostridium thermoaceticum*," *J. Biol. Chem.* 266:23824-23828 (1991).

Muh et al., "4-Hydroxybutyryl-CoA dehydratase from *Clostridium aminobutyricum*: characterization of FAD and iron-sulfur clusters involved in an overall non-redox reaction," *Biochemistry* 35:11710-11718 (1996).

Muh et al., "Mossbauer study of 4-hydroxybutyryl-CoA dehydratase—probing the role of an iron-sulfur cluster in an overall non-redox reaction," *Eur. J. Biochem.* 248:380-384 (1997).

Mukhopadhyay and Purwantini, "Pyruvate carboxylase from *Mycobacterium smegmatis*: stabilization, rapid purification, moleculare and biochemical characterization and regulation of the cellular level," *Biochim. Biophys. Acta.* 1475(3):191-206 (2000).

Muller et al., "Nucleotide exchange and excision technology (NExT) DNA shuffling: a robust method for DNA fragmentation and directed evolution," *Nucleic Acids Res.* 33(13):e117 (2005).

Muller, "Energy conservation in acetogenic bacteria," *Appl. Environ. Microbiol.* 69:6345-6353 (2003).

Muratsubaki and Enomoto, "One of the fumarate reductase isoenzymes from *Saccharomyces cerevisiae* is encoded by the OSM1 gene," *Arch. Biochem. Biophys.* 352:175-181 (1998).

Musfeldt and Schonheit, "Novel Type of ADP_Forming Acetyl Coenzyme a Synthetase in Hyperthermophilic Archaea: Heterologous Expression and Characterization of Isoenzymes from the Sulfate Reducer *Archaeoglobus fulgidus* and the Methanogen *Methanococcus jannaschii*," *J. Bacteriol.* 184(3):636-644 (2002).

Muyrers et al., "Rapid modification of bacterial artificial chromosomes by ET-recombination," *Nucleic Acids Res.* 27:1555-1557 (1999).

Naggert et al., "Cloning, Sequencing, and Characterization of *Escherichia coli* thioesteraseII," *J. Biol. Chem.* 266(17):11044-11050 (1991).

Nahvi et al., "Genetic control by a metabolite binding mRNA," *Chem. Biol.* 9:1043 (2002).

Naidu and Ragsdale, "Characterization of a three-component vanillate O-demethylase from *Moorella thermoacetica*," *J. Bacteriol.* 183:3276-3281 (2001).

Najafpour and Younesi, "Ethanol and acetate synthesis from waste gas using batch culture of *Clostridium ljungdahlii*," *Enzyme Microb. Techn.* 38[1-2], 223-228 (2006).

Najmudin et al., "Purification, crystallization and preliminary X-ray crystallographic studies on acetolactate decarboxylase," *Acta. Crystallogr. D. Biol. Crystallog.* 59:1073-1075 (2003).

Nakahigashi and Inokuchi, "Nucleotide sequence of the fadA and fadB genes from *Escherichia coli*," *Nucleic Acids Res.* 18(16):4937 (1990).

Nakano et al., "Characterization of Anaerobic Fermentative Growth of *Bacillus subtilis*: Identification of Fermentation End Products and Genes Required for Growth," *J. Bacteriol.* 6749-6755 (1997).

Namba et al., "Coenzyme A and Nicotinamide Adenine dinucleotide-deptendent Branched Chain α-Keto Acid Dehydrogenase," *J. Biol. Chem.* 244:4437-4447 (1969).

Ness et al., "Synthetic shuffling expands functional protein diversity by allowing amino acids to recombine independently," *Nat. Biotechnol.* 20(12):1251-1255 (2002).

Nexant ChemSystems Reports (2004).

Nimmo, "Kinetic mechanism of *Escherichia coli* isocitrate dehydrogenase and its inhibition by glyoxylate and oxaloacetate," *Biochem. J.* 579:2319-2322 (2005).

Nishizawa et al., "Gene expression and characterization of two 2-oxoacid:ferredoxin oxidoreductases from *Aeropyrum pernix* K1," *FEBS. Lett.* 579:2319-2322 (2005).

Niu, et al., "Benzene-free synthesis of adipic acid," *Biotechnol. Prog.* 18:201-211 (2002).

Nolling et al., "Genome sequence and comparative analysis of the solvent-producing bacterium *Clostridium acetobutylicum*," *J. Bacteriol.* 183(16):4823-4838 (2001).

Nowicki et al., "Recombinant tyrosine aminotransferase from *Trypanosoma cruzi*: structural characterization and site directed mutagenesis of a broad substrate specificity enzyme," *Biochim. Biophys. Acta* 1546(2):268-281 (2001).

O'Brien and Gennis, "Studies of the thiamin pyrophosphate binding site of *Escherichia coli* pyruvate oxidase. Evidence for an essential tryptophan residue," *J. Biol. Chem.* 255(8):3302-3307 (1980).

O'Brien et al., "Chemical, physical and enzymatic comparisons of formyltetrahydrofolate synthetases from thermo- and mesophilic Clostridia," *Experientia. Suppl.* 26:249-262 (1976).

O'Brien et al., "Regulation by lipids of cofactor binding to a peripheral membrane enzyme: binding of thiamin pyrophosphate to pyruvate oxidase," *Biochemistry* 16(14)3105-3109 (1977).

Ohgami et al., "Expression of acetoacetyl-CoA synthetase, a novel cytosolic ketone body-utilizing enzyme, in human brain," *Biochem. Pharmacol.* 65:989-994 (2003).

Ohsugi et al., "Metabolism of L-β-Lysine by a *Pseudomonas*, Purification and Properties of a Deacetylase-Thiolesterase utilizing 4-Acetamidobutyrl CoA and Related Compounds," *J. Biol. Chem.* 256:7642-7651 (1981).

Oku and Kaneda, "Biosynthesis of Branched-chain Fatty Acids in *Bacillis subtilis*," *J. Biol. Chem.* 263:18386-18396 (1988).

Okuno et al., "2-Aminoadipate-s-oxoglutarate aminotransferase isoenzymes in human liver: a plausible physiological role in lysine and tryptophan metabolism," *Enzyme Protein* 47(3):136-148 (1993).

Olivera et al., "Molecular characterization of the phenylacetic acid catabolic pathway in *Pseudomonas putida* U: The phenylacetyl-CoA catabolon," *Proc. Natl. Acad. Sci. USA* 95:6419-6424 (1998).

Onuffer and Krisch, "Redesign of the substrate specificity of *Escherichia coli* aspartate aminotransferase to that of *Escherichia coli* tyrosine aminotransferase by homology modeling and site-directed mutagenesis," *Protein Sci.* 4:1750-1757 (1995).

O'Reilly and Devine, "Sequence and analysis of the citrulline biosynthetic operon argC-F from *Bacillus subtilis*," *Microbiology* 140:1023-1025 (1994).

Ostermeier et al., "A combinatorial approach to hybrid enzymes independent of DNA homology," *Nat. Biotechnol.* 17(12):1205-1209 (1999).

Ostermeier et al., "Combinatorial protein engineering by incremental truncation," *Proc. Natl. Acad. Sci USA* 96(7):3562-3567 (1999).

O'Sullivan, et al., "Purification and characterisation of acetolactate decarboxylase from *Leuconostoc lactis* NCW1," *FEMS Microbiol. Lett.* 194(2):245-249 (2001).

Otten and Quax, "Directed evolution: selecting today's biocatalysts," *Biomol. Eng.* 1-9 (2005).

Palosaari and Rogers, "Purification and properties of the inducible coenzyme A-linked butyraldehyde dehydrogenase from *Clostridium acetobutylicum*," *J. Bacteriol.* 170(7):2971-2976 (1988).

Park and Lee, "Biosynthesis of poly(3-hydroxybutyrate-co-3-hydroxyalkanoates) by metabolically engineered *Escherichia coli* strains," *Appl. Biochem. Biotechnol.* 113-116:335-346 (2004).

Park and Lee, "Identification and Characterization of a New Enoyl coenzyme A Hydratase involved in biosynthesis of Medium-Chain-Length Polyhdroxyalkanoates in recombinant *Escherichia coli*," *J. Bacteriol.* 185(18):5391-5397 (2003).

Park and Lee, "New FadB homologous enzymes and their use in enhanced biosynthesis of medium-chain-length polyhydroxyalkanoates in FadB mutant *Escherichia coli*," *Biotechnol. Bioeng.* 86:681-686 (2004).

Park et al., "Regulation of succinate dehydrogenase (sdhCDAB) operon expression ion *Escherichia coli* in response to carbon supply and anaerobiosis: role of ArcA and Fnr," *Mol. Micriobiol.* 15:473-482 (1995).

Parkin et al., "Rapid and efficient electrocatalytic CO2/CO interconversions by *Carboxydothermus hydrogenoformans* CO dehydrogenase I on an electrode," *J. Am. Chem. Soc.* 129:10328-10329 (2007).

Parsot et al., "Nucleotide sequence of *Escherichia coli* argB and argC genes: comparison of N-acetylglutamate kinase and N-acetylglutamate-gamma-semialdehyde dehydrogenase with homologous and analogous enzymes," *Gene.* 68(2): 275-283 (1988).

Pauwels et al., "The N-acetylglutamate synthase?N-acetylglutamate kinase metabolon of *Saccharomyces cerevisiae* allows cor-ordinated feedback regulation of the first two steps in arginine biosynthesis," *Eur. J. Biochem.* 270:1014-1024 (2003).

Paxton et al., "Role of branched-chain 2-oxo acid dehydrogenase and pyruvate dehydrogenase in 2-oxobutyrate metabolism," *Biochem. J.* 234:295-303 (1986).

Peoples and Sinskey, "Fine structural analysis of the *Zoogloea ramigera* phhA-phhB locus encoding beta-ketothiolase and acetoacetyl-CoA reductase: nucleotide sequence of phbB," *Mol. Microbiol.* 3:349-357 (1989).

Pereira et al., "Active site mutants of *Escherichia coli* citrate synthase. Effects of mutations on catalytic and allosteric properties," *J. Biol. Chem.* 269:412-417 (1994).

Peretz and Burstein, "Amino Acid Sequence of Alcohol Dehydrogenase from the Thermophilic Bacterium *Thermoanaerobium brockii*," *Biochem.* 28:6549-6555 (1989).

Peretz et al., "Molecular cloning, nucleotide sequencing, and expression of genes encoding alcohol dehydrogenases from the thermophile *Thermoanaerobacter brockii* and the mesophile *Clostridium beijerinckii*," *Anaerobe* 3:259-270 (1997).

Perez et al., "*Escherichia coli* YqhD exhibits aldehyde reductase activity and protects from the harmful effect of lipid peroxidation-derived aldehydes," *J. Biol. Chem.* 283(12):7346-7353 (2008).

Petersen and Bennett, "Purification of acetoacetate decarboxylase from *Clostridium acetobutylicum* ATCC 824 and cloning of the acetoacetate decarboxylase gene in *Escherichia coli*," *Appl. Environ. Microbiol.* 56:3491-3498 (1990).

Petitdemange et al., "Regulation of the NADH and NADPH-ferredoxin oxidoreductases in clostridia of the butyric group," *Biochim. Biophys. Acta.* 421(2):334-337 (1976).

Phalip et al., "Purification and properties of the alpha-acetolactate decarboxylase from *Lactococcus lactis* subsp. *lactis* NCDO 2118," *FEBS Lett.* 351:95-99 (1994).

Pierce et al., "The complete genome sequence of *Moorella thermoacetia* (f. *Clostridium thermoaceticum*)," *Environ. Microbiol.* 10(10):2550-2573 (2008).

Pieulle, "Isolation and analysis of the gene encoding the pyruvate-ferredoxin oxidoreductase of *Desulfovibrio africanus*, production of the recombinant enzyme in *Escherichia coli*, and effect of carboxy-terminal deletions on its stability," *J. Bacteriol.* 179:5684-5692 (1997).

Pohl et al., "Remarkably broad substrate tolerance of malonyl-CoA synthetase, an enzyme capable of intracellular synthesis of polyketide precursors," *J. Am. Chem Soc.* 123(24): 5822-5823 (2001).

Pohlmann et al., "Genome sequence of the bioplastic-producing "Knallgas" bacterium *Ralstonia eutropha* H16," *Nat. Biotechnol.* 24(10):1257-1262 (2006).

Polovnikova et al., "Structural and Kinetic Analysis of Catalysis by a thiamin diphosphate-Dependent Enzyme, Benzoylformate Decarboxylase," *Biochemistry* 42:1820-1830 (2003).

Poston, "Assay of leucine 2,3-aminomutase," *Methods Enzymol.* 166:130-135 (1988).

Powlowski et al., "Purification and properties of the physically associated meta-cleavage pathway enzymes 4-hydroxy-2-ketovalerate aldolase and aldehyde dehydrogenase (acylating) from *Pseudomonas* sp. strain CF600," *J. Bacteriol.* 175:377-385 (1993).

Pritchard et al., "A general model of error-prone PCR," *J. Theor. Biol.* 234:497-509 (2005).

Pritchett and Metcalf, "Genetic, physiological and biochemical characterization of multiple methanol methyltransferase isozymes in *Methanosarcina acetivorans* C2A," *Mol. Microbiol.* 56:1183-1194 (2005).

Purnell et al., "Modulation of higher-plant NAD(H)-dependent glutamate dehydrogenase activity in transgenic tobacco via alteration of beta subunit levels," *Planta* 222:167-180 (2005).

Qi et al., "Functional expression of prokaryotic and eukaryotic genes in *Escherichia coli* for conversion of glucose to *p*-hydroxystyrene," *Metab. Eng.* 9:268-276 (2007).

Qian et al., "Metabolic engineering of *Escherichia coli* for the production of putrescine: a four carbon diamine," *Biotechnol. Bioeng.* 104(4)651-662 (2009).

Ragsdale, "Enzymology of the wood-Ljungdahl pathway of acetogenesis," Ann. NY Acad Sci. 1125:129-136 (2008).

Ragsdale, Life with carbon monoxide. *Crit Rev. Biochem. Mol. Biol.* 39:165-195 (2004).

Ragsdale, "Pyruvate ferredoxin oxidoreductase and its radical intermediate," *Chem. Rev.* 103:2333-2346 (2003).

Rajpal et al., "A general method for greatly improving the affinity of antibodies by using combinatorial libraries," *Proc. Natl. Acad. Sci. USA* 102(24)8466-8471 (2005).

Ramon-Maiques et al., "Structure of Acetylglutamate Kinase, a Key Enzyme for Arginine Biosynthesis and a Prototype for the Amino Acid Kinase Enzyme Family, during Catalysis," *Structure* 10:329-342 (2002).

Rangarajan et al., "Structure of [NiFe] hydrogenase maturation protein HypE from *Escherichia coli* and its interaction with HypF," *J. Bacteriol.* 190:1447-1458 (2008).

Rathinasabapathi, "Propionate, a source of β-alanine, is an inhibitor of β-alanine methylation in *Limonium latifolium*, Plumbaginaceae," *J. Plant Path.* 159:671-674 (2002).

Raybuck et. al., "Kinetic characterization of the carbon monoxide-acetyl-CoA (carbonyl group) exchange activity of the acetyl-CoA synthesizing Co dehydrogenase from *Clostridium thermoaceticum*," *Biochemistry* 27:7698-7702 (1988).

Recasens et al., "Cysteine Sulfinate Aminotransferase and Aspartate Aminotransferase Isoenzymes of Rat Brain. Purification, Characterization, and Further Evidence for Identity," *Biochemistry* 19:4583-4589 (1980).

Reda et al., "Reversible interconversion of carbon dioxide and formate by an electroactive enzyme," *Proc. Natl. Acad. Sci. USA* 105:10654-10658 (2008).

Reetz and Carballeria, "Iterative aturation mutagenesis (ISM) for rapid directed evolution of functional enzymes," *Nat. Protoc.* 2(4):891-903 (2007).

Reetz et al., "Creation of Enantioselective biocatalysts for Organic Chemistry by In Vitro Evolution," *Agnew. Chem. Int. Ed. Engl.* 36:2830-2832 (1997).

Reetz et al., "Directed Evolution of an Enantioselective Enzyme through Combinatorial Multiple-Cassette Mutagenesis," *Agnew. Chem. Int. Ed. Engl.* 40:3589-3591 (2001).

Reetz et al., "Expanding the Range of Substrate Acceptance of Enzymes: Combinatorial Active-site saturation test," *Agnew. Chem. Int. Ed. Engl.* 44:4192-4196 (2005).

Reetz et al., "Iterative Saturation Mutagenesis on the Basis of B Factors as a Strategy for Increasing Protein Thermostability," *Agnew. Chem. Int. Ed. Engl.* 45:7745-7751 (2006).

Regev-Rudzki et al., "Yeast Aconitase in Two Locations and Two Metabolic Pathways: Seeing Small Amounts is Believing," *Mol. Biol. Cell* 16:4163-4171 (2005).

Reidhaar-Olson and Sauer, "Combinatorial cassette mutagenesis as a probe of the informational content of protein sequences," *Science* 241(4861):53-57 (1988).

Reidhaar-Olson et al., "Random mutagenesis of protein sequences using oligonucleotide cassettes," *Methods Enzymol.* 208:564-586 (1991).

Reiser and Somerville, "Isolation of mutants of *Acinetobacter calcoaceticus* deficient in wax ester synthesis and complementation of one mutation with a gene encoding a fatty acyl coenzyme a reductase," *J. Bacteriol.* 179(9):2969-2975 (1997).

Repetto and Tzagoloff, "Structure and Regulation of KGD1, the Structural Gene for Yeast α-Ketoglutarate Dehydrogenase," *Mol. Cell.* 9:2695-2705 (1989).

Resnekov et al., "Organization and regulation of the *Bacillus subtilis* odhAB operon, which encodes two of the subenzymes of the 2-oxoglutarate dehydrogenase complex," *Mol. Gen. Genet.* 234(2):285-296 (1992).

Rigden et al., "A cofactor-dependent phosphoglycerate mutase homolog from *Bacillus stearothermophilus* is actually a broad specificity phosphatase," *Protein Sci.* 10:1835-1846 (2001).

Ringquist et al., "Translation initiation in *Escherichia coli*: sequences within the ribosome-binding site," *Mol. Microbial.* 6:1219-1229 (1992).

Riviere et al., "Acetyl:Succinate CoA-transferase in Procyclic *Trypanosoma brucei*," *J. Biol Chem.* 279(44):45337-45346 (2004).

Roberts et al., "Cloning and expression of the gene cluster encoding key proteins involved in acetyl-CoA synthesis in *Clostridium thermoaceticum*: CO dehydrogenase, the corrinoid/Fe-S protein, and methyltransferase," *Proc. Natl. Acad. Sci. USA* 86:32-36 (1989).

Robinson et al., "Studies on Rat Brain Acyl-Coenzyme a Hydrolase (Short Chain)," *Biochem. Biophys. Res. Commun.* 71:959-965 (1976).

Roca et al., "Metabolic engineering of ammonium assimilation in xylose-fermenting *Saccharmyces cerevisiae* improves ethanol production," *Appl. Environ. Microbiol.* 69(8):4732-7736 (2003).

Rodriguez et al., "Characterization of the p-coumaric acid decarboxylase from *Lactobacillus plantarum* CECT 748(T)," *J. Agric. Food Chem.* 56(9):3068-3072 (2008).

Rohdich et al., "Enoate reductases of Clostridia. Cloning, sequencing, and expression," *J. Biol. Chem.* 276(8):5779-5787 (2001).

Romero et al., "Partial purification, characterization and nitrogen regulation of the lysine epsilon-aminotransferase of *Streptomyces clavuligerus*," *J. Ind. Microbiol. Biotechnol.* 18(4):241-246 (1997).

Rose and Weaver, "The role of the allosteric B site in the fumarase reaction," *Proc. Natl. Acad. Sci. USA* 101:3393-3397 (2004).

Rose et al., "Enzymatic phosphorylation of acetate," *J. Biol. Chem.* 211(2):737-756 (1954).

Rother and Metcalf, "Anaerobic growth of *Methanosarcina acetivorans* C2A on carbon monoxide: an unusual way of life for a methanogenic archaeon," *Proc. Natl. Acad. Sci. USA* 101:16929-16934 (2004).

Rother et al., "Genetic and proteomic analyses of CO utilization by *Methanosarcina acetivorans*," *Arch. Microbiol.* 188:463-472 (2007).

Roy and Dawes, "Cloning and Characterization of the Gene Encoding Lipamide Dehydrogenase in *Saccharomyces cerevisiae*," *J. Gen. Microbiol.* 133:925-933 (1987).

Ruldeekulthamrong et al., Molecular characterization of lysine 6-dehydrogenase from *Achromobacter denitrificans, BMB Rep.* 41:790-795 (2008).

Sabo et al., "Purification and Physical Properties of Inducible *Escherichia coli* Lysine Decarboxylase," *Biochemistry* 13(4):662-670 (1974).

Sakai et al., "Acetate and ethanol production from H2 and CO2 by *Moorella* sp. using a repeated batch culture," *J. Biosci. Bioeng.* 99:252-258 (2005).

Salmon et al., "Global gene expression profiling in *Escherichia coli* K12: effects of oxygen availability and ArcA," *J. Biol. Chem.* 280(15):15084-15096 (2005).

Samsonova et al., "Molecular cloning and characterization of *Escherichia coli* K12 ygjG gene," *BMC Microbiol.* 3:2 (2003).

Sariaslani, "Development of a Combined Biological and Chemical Process for Production of Industrial Aromatics from Renewable Resources," *Annu. Rev. Microbiol.* 61:51-69 (2007).

Sass et al., "Folding of fumarase during mitochondrial import determines its dual targeting in yeast," *J. Biol. Chem.* 278(46):45109-45116 (2003).

Sato et al., "Poly[(R)-3-Hydroxybutyrate] Formation in *Escherichia coli* from Glucose through an Enoyl-CoA Hydratase-Mediated Pathway," *J. Biosci. Bioeng.* 103(1):38-44 (2007).

Sauer et al., "Methanol:coenzyme M methyltransferase from *Methanosarcina barkeri*. Purification, properties and encoding genes of the corrinoid protein MT1," *Eur. J. Biochem.* 243:670-677 (1997).

Sawers and Boxer, "Purification and properties of membrane-bound hydrogenase isoenzyme 1 from anaerobically grown *Escherichia coli* K12," *Eur. J. Biochem.* 156:265-275 (1986).

Sawers et al., "Characterization and physiological roles of membrane-bound hydrogenase isoenzymes from *Salmonella typhimurium*," *J. Bacteriol.* 168:398-404 (1986).

Sawers et al., "Differential expression of hydrogenase isoenzymes in *Escherichia coli* K-12: evidence for a third isoenzyme," *J. Bacteriol.* 164:1324-1331 (1985).

Sawers, "The hydrogenases and formate dehydrogenases of *Escherichia coli*," *Antonie Van Leeuwenhoek* 66:57-88 (1994).

Scherf and Buckel, "Purification and properties of an iron-sulfur and FAD-containing 4-hydroxybutyryl-CoA dehydratase/vinylacetyl-CoA Δ3-Δ2-isomerase from *Clostridium aminobutyricum*," *Eur. J. Biochem.* 215:421-429 (1993).

Schulz et al., "Stereopsecific Production of the Herbicide Phosphinothricin (Glufosinate) by Transamination: Isolation and Characterization of a Phosphinothricin-Specific Transaminase from *Escherichia coli*," *Appl. Environ. Microbiol.* 56:1-6 (1990).

Scott and Jakoby, "Soluble γ-Aminobutyric-Glutamic Transaminase from *Pseudomonas fluorescens*," *J. Biol. Chem.* 234:932-936 (1959).

Seedorf et al., "The genome of *Clostridium kluyveri*, a strict anaerobe with unique metabolic features," *Proc. Natl. Acad. Sci. USA* 105(6):2128-2133 (2008).

Selifonova et al., "Rapid evolution of novel traits in microorganisms," *Appl. Environ. Microbiol.* 67(8):3645-3649 (2001).

Sen et al., "Developments in directed evolution for improving enzyme functions," *Appl. Biochem. Biotechnol.* 143(3):212-223 (2007).

Seravalli et al., "Evidence that NiNi acetyl-CoA synthase is active and that the CuNi enzyme is not," *Biochemistry* 43:3944-3955 (2004).

Seravalli et al., "Mechanism of transfer of the methyl group from (6S)-methyltetrahydrofolate to the corrinoid/iron-sulfur protein catalyzed by the methyltransferase from *Clostridium thermoaceticum*: a key step in the Wood-Ljungdahl pathway of acetyl-CoA synthesis," *Biochemistry* 38:5728-5735 (1999).

Shafiani et al., "Cloning and characterization of aspartate-β-semialdehyde dehydrogenase from *Mycobacterium tuberculosis* H37 Rv," *J. Appl. Microbiol.* 98:832-838 (2005).

Shalel-Levanson et al., "Effect of ArcA and FNR on the expression of genes related to the oxygen rregulation and the glycolysis pathway in *Eschericiha coli* under microaerobic growth conditions," *Biotechnol. Bioeng.* 92(2):147-159 (2005).

Shames et al., "Interaction of aspartate and aspartate-derived antimetabolites with the enzymes of the threonine biosynthetic pathway of *Escherichia ecoli*," *J. Biol. Chem.* 259(24):15331-15339 (1984).

Shao et al., "Random-priming in vitro recombination: an effective tool for directed evolution," *Nucleic Acids Res.* 26(2):681-683 (1998).

Sheppard et al., "Purification and properties of NADH-dependent 5, 10-Methylenetetrahydrofolate reductase (MetF) from *Escherichia coli*," *J. Bacteriol.* 181:718-725 (1999).

Shi et al., "The structure of L-aspartate ammonia-lyase from *Escherichia coli*," *Biochem.* 36(30):9136-9144 (1997).

Shimomura et al., "3-Hydroxyisobutyryl-CoA Hydrolase," *Meth. Enzymol.* 324:229-240 (2000).

Shimomura et al., "Purification and Partial Characterization of 3-Hydroxyisobutyryl-coenzyme A Hydrolase of Rat Liver," *J. Biol. Chem.* 269:14248-14253 (1994).

Shimoyama et al., "MmcBC in *Pelotomaculum thermopropionicum* represents a novel group of prokaryotic fumarases," *FEMS Microbiol Lett.* 270(2):207-213 (2007).

Shingler et al., "Nucleotide Sequence and Functional Analysis of the Complete Phenol/3,4-Dimethylphenol Catabolic Pathway of *Pseudomonas* sp. Strain CF600," *J. Bacteriol.* 174(3):711-724 (1992).

Shukla et al., "production of D(−)-lactate from sucrose and molasses," *Biotechnol. Lett.* 26(9):689-693 (2004).

Sieber et al., "Libraries of hybrid proteins from distantly related sequences," *Nat. Biotechnol.* 19(5):456-460 (2001).

Siebers et al., "Reconstruction of the central carbohydrate metabolism of *Thermoproteus tenax* by use of genomic and biochemical data," *J. Bacteriol.* 186(7):2179-2194 (2004).

Siegert et al., "Exchanging the substrate specificities of pyruvate decarboxylase from *Zymomonas mobilis* and benzoylase from *Pseudomonas putida*," *Protein Eng. Des. Sel.* 18:345-357 (2005).

Siminov et al.,"Application of Gas Chromatography and Gas Chromatography-Mass Spectrometry to the Detection of γ-Hydroxybutyric Acid and Its Precursors in Various Materials," *J. Anal. Chem.* 59:965-971 (2004).

Simpma et al., "Microbial CO Conversions with Applications in Synthesis Gas Purification and Bio-Desulfurization," *Crit. Rev. Biotech.* 26:41-65 (2006).

Sinclair et al, "Purification and characterization of the branched chain alpha-ketoacid dehydrogenase complex from *Saccharomyces cerevisiae*," *Biochem. Mol. Biol. Int.* 31(5):911-922 (1993).

Sivaraman et al., "Codon choice in genes depends on flanking sequence information—implications for theoretical reverse translation," *Nucleic Acids Res.* 36:e16 (2008).

Sjostrom et al., "Purfication and characterisation of a plasminogen-binding protein from *Haemophilus influenzae*. Sequence determination reveals identity with aspartase," *Biochim. Biophys. Acta.* 1324:182-190 (1997).

Skarstedt and Silverstein, "*Escherichia coli* Acetate Kinase Mechanism Studied by Net Initial Rate, Equilibriu, and Independent Isotopic Exchange Kinetics," *J. Biol. Chem.* 251:6775-6783 (1976).

Smit et al., "Identification, Cloning, and Characterization of a *Lactococcus lactis* Branched-Chain α-Keto Acid Decarboxylase Involved in Flavor Formation," *Appl. Environ. Microbiol.* 71:303-311 (2005).

Smith et al., "Fumarate metabolism and the microaerophily of *Campylobacter* species," *Int. J. Biochem. Cell Biol.* 31:961-975 (1999).

Smith et al., "Purification and characteristics of a gamma-glutamyl kinase involved in *Escherichia coli* proline biosynthesis," *J.Bacteriol.* 157:545-551 (1984).

Soda and Misono, "L-Lysine:alpha-ketoglutarate aminotransferase. II. Purification, crystallization, and properties," *Biochemistry* 7(11):4110-4119 (1968).

Sokatch et al., "Purification of a Branched-Chain Keto Acid Dehydrogenase from *Pseudomonas putida*," *J. Bacteriol.* 647-652 (1981).

Song et al., "Structure, Function, and Mechanism of the Phenylacetate Pathway Hot Dog-fold Thioesterase PaaI," *J. Biol. Chem.* 281(16):11028-11038 (2006).

St Maurice et al., "Flavodoxin:quinone reductase (FqrB): a redox partner of oxidation to pyruvate:ferredoxin oxidoreductase that reversibly couples pyruvate NADPH production in *Helicobacter pylori* and *Campylobacter jejuni*," *J. Bacteriol.* 189(13):4764-4773 (2007).

Stadtman, "The enzymatic synthesis of β-alanyl coenzyme A," *J. Am. Chem. Soc.* 77:5765-5766 (1955).

Stanley et al., "Expression and Sterochemical and Isotope Effect Studies of Active 4-Oxalocrotonate Decarboxylase," *Biochem.* 39:(12):3514 (2000).

Starai et al., "Acetate excretion during rowth of *Salmonella enterica* on ethanolamine requires phosphotransacetylase (EutD) activity, and acetate recapture requires acetyl-CoA synthetase (Acs) and phosphotransacetylase (Pta) activities," *Microbiology* 151(Pt 11):3793-3801 (2005).

Starai et al., "Residue Leu-641 of Acetyl-CoA synthetase is critical for the acetylation of residue Lys-609 by the Protein acetyltransferase enzyme of *Salmonella enterica*," *J. Biol. Chem.* 280(28):26200-26205 (2005).

Steffan and McAlister-Henn, "Isolation and Characterization of the Yeast Gene Encoding the MDH3 Isozyme of Malate Dehydrogenase," *J. Biol. Chem.* 267(34):24708-24715 (1992).

Steinbüchel and Schlegel, "NAD-linked L(+)-lactate dehydrogenase from the strict aerobe *Alcaligenes eutrophus*. 2. Kinetic properties and inhibition by oxaloacetate," *Eur. J. Biochem.* 130(2):329-334 (1983).

Steinbuchel and Schlegel, "A multifunctional fermentative alcohol dehydrogenase from the strict aerobe *Alcaligenes eutrophus*: purification and properties," *Eur. J. Biochem.* 141:555-564 (1984).

Stemmer, "DNA Shuffling by random fragmentation and reassembly: in vitro recombination for molecular evolution," *Proc. Natl. Acad. Sci. USA* 91(22):10747-10751 (1994).

Stemmer, "Rapid evolution of a protein in vitro by DNA shuffling," *Nature* 370(6488):389-391 (1994).

Stokell et al., "Probing the roles of key residues in the unique regulatory NADH binding site of type II citrate synthase of *Escherichia coli*," *J. Biol. Chem.* 278(37):35435-35443 (2003).

Stols et al., "New vectors for co-expression of proteins: Structure of *Bacillus subtilis* ScoAB obtained by high-throughput protocols," *Protein Expr. Purif.* 53:3960403 (2007).

Stoyan et al., "Cloning, sequencing and overexpression of the leuine dehydrogenase gene from *Bacillus cereus*," *J. Biotechnol.* 54:77-80 (1997).

Strauss and Fuchs, "Enzymes of a novel autotrophic CO2 fixation pathway in the phototrophic bacterium *Chloroflexus aurantiacus*, the 3-hydroxypropionate cycle," *Eur. J. Biochem.* 215:633-643 (1993).

Suda et al., "Purification and properties of alpha-keoadipate reductase, a newly discovered enzyme from human placenta," *Arch. Biochem. Biophys.* 176(2):610-620 (1976).

Suda et al., "Subcellular Localization and tissue Distribution of α-Ketodaipate Reduction and Oxidation in the Rat," *Biochem. Biophys. Res. Commun.* 77:586-591 (1977).

Suematsu et al., "Molecular cloning and functional expression of rat liver cytosolic acetyl-CoA hydrolase," *Eur. J. Biochem.* 268(9):2700-2709 (2001).

Sulzenbacher et al., "Crystal structure of *E.coli* alcohol dehydrogenase YqhD: evidence of a covalently modified NADP coenzyme," *J. Mol. Biol.* 342(2):489-502 (2004).

Suthers et al., "Metabolic flux elucidation for large-scale models using 13C labeled isotopes," *Metab. Eng.* 387-405 (2007).

Suzuki et al., "GriC and GriD Constitute a carboxylic acid reductase involved in grixazone biosynthesis in *Streptomyces griseus*," *J. Antibiot.* 60(6):380-387 (2007).

Suzuki, "Phosphotransacetylase of *Escherichia coli* B, activation by pyruvate and inhibition by NADH and certain nucleotides," *Biochim. Biophys. Acta* 191(3):559-569 (1969).

Svetlitchnyi et al., "A functional Ni-Ni-[4Fe-4S] cluster in the monomeric acetyl-CoA synthase from *Carboxydothermus hydrogenoformans*," *Proc. Natl. Acad. Sci. USA* 101:446-451 (2004).

Svetlitchnyi et al., "Two membrane-associated NiFeS-carbon monoxide dehydrogenases from the anaerobic carbon-monoxide-utilizing eubacterium *Carboxydothermus hydrogenoformans*," *J. Bacteriol.* 183:5134-5144 (2001).

Takagi and Kisumi, "Isolation of a Versatile *Serratia marcescens* Mutant as a Host and Molecular Cloning of the Aspartase Gene," *J. Bacteriol.* 161(1):1-6 (1985).

Takagi et al., "Purfication, Crystallization, and Molecular Properties of Aspartase from *Pseudomonas fluorescens*," *J. Biochem.* 96:545-552 (1984).

Takahashi et al., "Metabolic Pathways for Cytoxic End Product Formation from Glutamate- and Aspartate-Containing Peptides by *Porphyromonas gingivalis*," *J. Bacteriol.* 4704-4710 (2000).

Takahashi-Abbe et al., "Biochemical and functional properties of a pyruvate formate-lyase (PFL)-activating system in *Streptococcus mutans*," *Oral Microbiol. Immunol.* 18(5)293-297 (2003).

Takanashi et al., "Characterization of a novel 3-hydroxybutyrate dehydrogenase from *Ralstonia pickettii* T1," Antonie van Leeuwnhoek 95(3):249-262 (2009).

Takatsuka et al., "Gene cloning and molecular characterization of lysine decarboxylase from *Selenomonas ruminantium* delineate its evolutionary relationship to ornithine decarboxylases from eukaryotes," *J. Bacteriol.* 182(23):6732-6741 (2000).

Takatsuka et al., "Identification of the amino acid residues conferring substrate specificity upon *Selenomonas ruminantium* lysine decarboxylase," *Biosci. Biotechnol. Biochem.* 63(10):1843-1846 (1999).

Tallant and Krzycki, "Methylthiol:coenzyme M methyltransferase from *Methanosarcina barkeri*, an enzyme of methanogenesis from dimethylsulfide and methylmercaptopropionate," *J. Bacteriol.* 179:6902-6911 (1997).

Tallant and Krzycki, "The MtsA subunit of the methylthiol:coenzyme M methyltransferase of *Methanosarcina barkeri* catalyses both half-reactions of corrinoid-dependent dimethylsulfide: coenzyme M methyl transfer," *J. Biol. Chem.* 276:4485-4493 (2001).

Tallant, "Coenzyme M methylase activity of the 480-kilodalton corrinoid protein from *Methanosarcina barkeri*," *J. Bacteriol.* 178:1295-1301 (1996).

Tamaki et al., "Purification, Properties, and Sequencing of Aminisobutyrate Aminotransferases from Rat Liver," *Meth. Enzymol.* 324:376-389 (2000).

Tanaka et al., "Cloning and characterization of a human orthologue of testis-specific succinyl CoA:3-oxo acid CoA transferase (Scot-t) cDNA," *Mol. Hum. Reprod.* 8:16-23 (2001.).

Tanaka et al., "Lysine decarboxylase of *Vibrio parahaemolyticus*: kinetics of transcription and role in acid resistance," *J. Appl. Microbiol.* 104(5):1283-1293 (2007).

Tang et al., "Identification of a novel pyridoxal 5'-phosphaste binding site in adenosylcobalamin-dependent lysine 5,6-aminomutase from *Porphyromonas gingivalis*," *Biochemistry* 41(27):8767-8776 (2002).

Tani et al., "Thermostable NADP(+)-dependent medium-chain alcohol dehydrogenase from *Acinetobacter* sp strain M-1: Purification and characterization and gene expression in *Escherichia coli*," *Appl. Environ. Microbiol.* 66:5231-5235 (2000).

ter Schure et al., "Pyruvate Decarboxylase Catalyzes Decarboxylation of Branched-Chaing 2-Oxo Acids but Is Not Essential for Fusel Alcohol Production by *Saccharomyces cerevisiae*," *Appl. Environ. Microbiol.* 64(4):1303-1307 (1998).

Thauer, "Microbiology. A fifth pathway of carbon fixation," *Science* 318:1732-1733 (2007).

Tian et al., "Variant tricarboxylic acid cycle in *Mycobacterium tuberculosis*: identification of alpha-ketoglutarate decarboxylase," *Proc. Natl. Acad. Sci. USA* 102(30):10670-10675 (2005).

Tobin et al., "Localization of the lysine epsilon-aminotransferase (lat) and delta- (L-alpha-aminoadipyl)-L-cysteinyl-D-Valine synthetase (pcbAB) genes from *Streptomyces clavuligerus* and production of lysine epsilon-aminotransferase activity in *Escherichia coli*," *J. Bacteriol.* 173(19):6223-6229 (1991).

Tretter and Adam-Vizi, "Alpha-ketoglutarate dehydrogenase: a target and generator of oxidative stress," *Philos. Trans. R. Soc. Lond B. Biol. Sci.* 360:2335-2345 (2005).

Tseng et al., "Metabolic engineering of *Escherichia coli* for enhanced production of (R)- and (S)-3-hydroxybutyrate," *Appl. Environ. Microbiol.* 75(10):3137-3145 (2009).

Tseng et al., "Oxygen- and growth rate-dependent regulation of *Escherichia coli* fumarase (FumA, FumB, and BumC) activity," *J. Bacteriol.* 183(2):461-467 (2001).

Tucci and Martin, "A novel prokaryotic trans-2-enoyl-CoA reductase from the spirochete *Treponema denticola*," *FEBS Lett.* 581:1561-1566 (2007).

Twarog and Wolfe, "Role of Buyryl Phosphate in the Energy Metabolism of *Clostridium tetanomorphum*," *J. Bacteriol.* 86:112-117 (1963).

Uchiyama et al., "Identification of the4-Hydroxycinnamate Decarboxylase (PAD) Gene of *Klebsiella oxytoca*," *Biosci. Biotechnol. Biochem.* 72:116-123 (2008).

Uttaro and Opperdoes., "Purification and characterisation of a novel iso-propanol dehydrogenase from *Phytomonas* sp," *Mol. Biochem. Parasitol.* 85:213-219 (1997).

Valdes-Hevia and Gancedo, "Isolation and characterization of the gene encoding phosphoenolpyruvate carboxykinase from *Saccharomyces cerevisiae*," *FEBS Lett.* 258:313-316 (1989).

Valentine and Wolfe, "Purification and role of phosphotransbutyrylase," *J. Biol. Chem.* 235:1948-1952 (1960).

Vamecq et al., "The microsomal dicarboxylyl-CoA synthetase," *Biochem. J.* 230:683-693 (1985).

van der Voorhorst et al., "Genetic and biochemcial characterization of a short-chain alcohol dehydrogenase from the hyperthermophilic archaeon *Pyrococcus furiosus*," *Eur. J. Biochem.* 268:3062-3068 (2001).

Vanderwinkel et al., "Growth of *Escherichia coli* on Fatty Acids: Requirement for Coenzyme a Transferase Activity," *Biochem. Biophys. Res. Commun.* 33:902-908 (1968).

VanGrinsven et al., "Acetate:Succinate CoA-transferase in the Hydrogenosomes of *Trichomonas vaginalis*," *J. Biol. Chem.* 283:1411-1418 (2008).

Varma and Palsson, "Metabolic Flux balancing: Basic concepts, Scientific and Practical Use," *Biotechnol.* 12:994-998 (1994).

Vazquez et al., "Phosphotransbutyrylase Expression in *Bacillus megaterium*," *Curr. Microbiol.* 42:345-349 (2001).

Venkitasubramanian et al., "Biocatalytic Reduction of Carboxylic Acids: Mechanism and Applications," Chpater 15, Biocatalysis in the Pharmaceitucal and Biotechnology Industries, ed., Rn.N. Patel, CRC Press LLC, Boca Raton, FL (2006).

Venkitasubramanian et al., "Reduction of Carboxylic Acids by Nocardia Aldehyde Oxidoreductase Requires a Phosphopantetheinylated Enzyme," *J. Biol Chem.* 282:478-485 (2007).

Vernal et al., "Cloning and heterologous expression of a broad specificity aminotransferase of *Leishmania mexicana* promastigotesl," *FEMS Microbiol. Lett.* 229(2):217-222 (2003).

Vernal et al., "Isolation and partial characterization of a broad specificity aminotransferase from *Leishmania mexicana* promastigotes," *Mol. Biochem. Parasitol.* 96(1-2):83-92 (1998).

Vey et al., "Structural basis for glycyl radical formation by pyruvate formate-lyase activating enzyme," *Proc. Natl. Acad. Sci. USA* 105(42):16137-16141 (2008).

Viola, "L-aspartase: new tricks from an old enzyme," *Adv. Enzymol. Relat. Areas. Mol. Biol.* 74:295-341 (2000).

Voets et al., "Reduced intracellular ionic strength as the initial trigger for activation of endothelial volume-regulated anion channels," *Proc. Natl. Acad. Sci. USA* 96:5298-5303 (1999).

Volkov et al., "Random chimeragenesis by heteroduplex recombination," *Methods. Enzymol.* 328:456-463 (2000).

Volkov et al., "Recombination and chimeragenesis by in vitro heteroduplex formation and in vivo repair," *Nucleic Acids Res.* 27(18):e18 (1999).

Wakil et al., "Studies on the Fatty Acid Oxidizing System of Animal Tissues," *J. Biol. Chem.* 207:631-638 (1954).

Walker et al., "Yeast pyruvate carboxylase: identification of two genes encoding isoenzymes," *Biochem. Biophys. Res. Commun.* 176:1210-1217 (2007).

Walter et al., "Sequence and arrangement of two genes of the butyrate-synthesis pathway of *Clostridium acetobutylicum* ATCC 824," *Gene* 134:107-111 (1991).

Wang et al., "Molecular cloning and functional identification of a novel phenylacetyl-CoA ligase gene from *Penicillium chrysogenum*," *Biochem. Biophys. Res. Commun.* 360(2):453-458 (2007).

Wang et al., "The primary structure of branched-chain α-oxo acid dehydrogenase from *Bacillus subtilis* and its similarity to other α-oxo acid dehydrogenases," *Eur. J. Biochem.* 213:1091-1099 (1993).

Ward et al., "Molecular analysis of the role of two aromatic aminotransferases and a broad-specificity aspartate aminotransferase in the aromatic amino acid metabolism of *Pyrococcus furiosus*," *Archea* 133-141 (2002).

Weaver, "Structure of free fumarase C from *Eschericiha coli*," *Acta. Crystallog. D. Biol. Crystallogr.* 61:1395-1401 (2005).

Weidner and Sawers, "Molecular Characterization of the Genes Encoding Pyruvate Formate-Lyase and Its Activating Enzyme of *Clostridium pasteruianum*," *J. Bacteriol.* 178(8):2440-2444 (1996).

Welch et al., "Purification and characterization of the NADH-dependent butanol dehydrogenase from *Clostridium acetobutylicum* (ATCC 824)," *Arch. Biochem. Biophys.* 273(2):309-318 (1989).

Westin et al., "The Identification of Succinyl-CoA Thioesterase Suggests a Novel Pathway for Succinate Production in Peroxisomes," *J. Biol. Chem.* 280(46):38125-38132 (2005).

Wexler et al., "A wide host-range metagenomic library from a waste water treatment plant yields a novel alcohol/aldehyde dehdrogenase," *Environ. Microbiol.* 7:1917-1926 (2006).

Whalen and Berg, "Analysis of an *avt*A:: Mu $d$1(Ap lac) Mutant: Metabolic role of Transaminase C," *J. Bacteriol.* 150(2):739-746 (1982).

Whalen and Berg, "Gratuitous Repression of *avt*A in *Escherichia coli* and *Salmonella typhimurium*," *J. Bacteriol.* 158(2):571-574 (1984).

Whitehead and Rabinowitz, "Cloning and expression in *Escherichia coli* of the gene for 10-formyltetrahydrofolate synthetase from *Clostridium acidiurici* ("*Clostridium acidi-urici*")," *J. Bacteriol.* 167:205-209 (1986).

Whitehead and Rabinowitz, "Nucleotide sequence of the *Clostridium acidiurici* ("*Clostridium acidi-urici*") gene for 10-formyltetrahydrofolate synthetase shows extensive amino acid homology with the trifunctional enzyme C1-tetrahydrofolate synthase from *Saccharomyces cerevisiae*," *J. Bacteriol.* 170:3255-3261 (1988).

Wiesenborn et al., "Coenzyme A Transferase from *Clostridium acetobutylicum* ATC 824 and Its Role in the Uptake of Acids," *Appl. Environ. Microbiol.* 55:323-329 (1989).

Wilkie and Warren, "Recombinant Expression, Purification, and Characterization of Three Isoenzymes of Aspartate Aminotrannsferase from *Arabidopsis thaliana*," *Protein. Expr. Purif.* 12:381-389 (1998).

Wilks et al., "A specific, highly active malate dehydrogenase by redesign of a lactate dehydrogenase framework," *Science* 242(4885):1541-1544 (1988).

Wilks et al., "Design for a broad substrate specificity keto acid dehydrogenase," *Biochemistry* 29(37)8587-8591 (1990).

Wilks et al., "Design of a specific phenyllactate dehydrogenase by peptide loop exchange on the *Bacillus stearothermophilus* lactate dehydrogenase framework," *Biochemistry* 31(34):7802-7806 (1992).

Willke and Vorlop, "Biotechnological production of itaconic acid," *Appl. Microbiol. Biotechnol.* 56:289-295 (2001).

Winzer et al., "Differential regulation of two thiolase genes from *Clostridium acetobutylicum* DSM 792," *J. Mol. Microbiol. Biotechnol.* 2:531-541 (2000).

Wong et al., "Sequence satruation mutagenesis with tunable mutation frequencies," *Anal. Biochem.* 341:187-189 (2005).

Wong et al., "Sequence saturation mutagenesis (SeSaM): a novel method for directed evolution," *Nucleic Acids Res.* 32(3):e26 (2004).

Wong et al., "Transversion-enriched sequence saturation mutagenesis (SeSaM-Tv+): a random mutagenesis method with consecutive nucleotide exchanges that complements the bias of error-prone PCR," *Biotechnol. J.* 74-82 (2008).

Woods, "Two biochemically distinct classes of fumarase in *Escherichia coli*," *Biochim. Biophys. Acta* 954(1):14-26 (1988).

Wu et al., "Life in hot carbon monoxide: the complete genome sequence of *Carboxydothermus hydrogenoformans* Z-2901. PLoS," *Genet* 1:e65 (2005).

Wynn et al., "Chaperonins GroEL and GroES Promote Assembly of Heterotramers (α2β2) of Mammalian Mitochondrial Branched-chain α-Keto Acid Decarboxylase in *Escherichia coli*," *J. Biol. Chem.* 267(18):12400-12403 (1992).

Wynn et al., "Cloning and Expression in *Escherichia coli* of a Mature E1β Subunit of Bovine Mitochondrial Branched-chain α-Keto Acid Dehydrogenase Complex," *J. Biol. Chem.* 267(3):1881-1887 (1992).

Yagi et al., "Aspartate: 2-Oxoglutarate Aminotransferase from Bakers' Yeast: Crystallization and Charactierization," *J. Biochem.* 92:35-43 (1982).

Yagi et al., "Crystallization and Properties of Aspartate Aminotransferase from *Escherichi coli* B," *FEBS Lett.* 100(1)81-84 (1979).

Yagi et al., "Glutamate-Aspartate Transaminase from Microorganisms," *Meth. Enzymol.* 17:83-89 (1985).

Yamamoto et al., "Carboxylation reaction catalyzed by 2-oxoglutarate:ferredoxin oxidoreductases from *Hydrogenobacter thermophilus*," *Extremophiles* 14:9-85 (2010).

Yamamoto et al., "Purification and properties of NADP-dependent formate dehydrogenase from *Clostridium thermoaceticum*, a tungsten-selenium-iron protein," *J. Biol. Chem.* 258:1826-1832 (1983).

Yang et al, "Nucleotide Sequence of the fadA Gene," *J. Biol. Chem.* 266(24):16255 (1991).

Yang et al., "Aspartate Dehydrogenase, a Novel Enszyme Idnetified from Structural and Functional Studies of TM16343," *J. Biol. Chem.* 278:8804-8808 (2003).

Yang et al., "Continuous cultivation of *Lactobacillus rhamnosus* with cell recycling using an acoustic cell settler," *Biotechnol. Bioprocess. Eng.* 7(6):357-361 (2002).

Yang et al., "Nucleotide Sequence of the fadA Gene," *J. Biol. Chem.* 265(18):10424-10429 (1990).

Yang et al., Nucleotide sequence of the promoter and fadB gene of the fadBA operon and primary structure of the multifunctional fatty acid oxidation protein from *Escherichia coli, Biochemistry* 30(27):6788-6795 (1991).

Yano et al., "Directed evolution of an aspartate aminotransferase with new substrate specificities," *Proc. Natl. Acad. Sci. USA* 95:5511-5515 (1998).

Yarlett et al., "*Trichomonas vaginalis*: characterization of ornithine decarboxylase," *Biochem. J.* 293:487-493 (1993).

Yoshida et al., "the structures of L-rhamnose isomerase from *Pseudomonas stutzeri* in complexs with L-rhamnose and D-allose provide insights into broad substrate specificity," *J. Mol. Biol.* 365(5): 1505-1516 (2007).

Youngleson et al., "Homology between hydroxybutyryl and hydroxyacyl coenzyme A dehydrogenase enzymes from *Clostridium acetobutylicum* fermentation and vertebrate fatty acid beta-oxidation pathways," *J. Bacteriol.* 171(12):6800-6807 (1989).

Yun et al., "The genes for anabolic 2-oxoglutarate: ferredoxin oxidoreductse from *Hydrogenobacter thermophilus* TK-6," *Biochem. Biophys. Res. Commun.* 282(2):589-594 (2001).

Yun et al., "Omega-Amino acid:pyruvate transaminase from *Alcaligenes denitrificans* Y2k-2: a new catalyst for kinetic resolution of beta-amino acids and amines," *Appl. Environ. Microbiol.* 70(4):2529-2534 (2004).

Zeiher and Randall, "Identification and Characterization of Mitochondrial Acetyl-Coenzyme A Hydrolase from *Pisum sativum* L. Seedlings," *Plant Physiol.* 94:20-27 (1990).

Zhang et al., "2-Oxoacid: Ferredoxin Oxidoreductase from the *Thermoacidophilic Archaeon, Sulfolobus* sp. Strain $7^1$," *J. Biochem.* 120:587-599 (1996).

Zhang et al., "A new logic for DNA engineering using recombination in *Escherichia coli*," *Nat. Genet.* 20:123-128 (1998).

Zhang et al., "Directed evolution of a fucosidase from a galactosidase by DNA shuffling and screening," *Proc. Natl. Acad. Sci. USA* 94:4504-4509 (1997).

Zhang et al., "Isolation and Properties of a levo-lactonase from *Fusarium proliferatum* ECD2002: a robust biocatalyst for production of chiral lactones," *App. Microbiol. Biotechnol.* 75(5):1087-1094 (2007).

Zhao et al., "Molecular evolution by staggered extension process (StEP) in vitro recombination," *Nat. Biotechnol.* 16(3):258-261 (1998).

Zhou et al., "Engineering a native homoethanol pathway in *Escherichia coli* B for ethanol production," *Biotechnol. Lett.* 30:335-342 (2008).

Zhou et al., "Isolation, crystallization and preliminary X-ray analysis of a methanol-induced corrinoid protein from *Moorella thermoacetica*," *Acta Crystallogr. Sect. F Struct.Biol Cryst. Commun.* 61:537-540 (2005).

Zhou et al., "The remarkable structural and functional organization of the eukaryotic pyruvate dehydrogenase complexes," *Proc. Natl. Acad. Sci. USA* 98:14802-14807 (2001).

Zhuang et al., "TheYbgC protein encoded by the ybgC gene of the tol-pal gene cluster of *Haemophilus influenzae* catalyzes acyl-coenzyme A thioester hydrolysis," *FEBS Lett.* 516:161-163 (2002).

URL expressys.de/. (Printed Dec. 21, 2009).

URL openwetware.org/wiki/Synthetic_Biology:BioBricks, Synthetic Biology:BioBricks, portal for information relating to the Registry of Standard Biological Parts (Printed Dec. 21, 2009).

URL_shigen.nig.ac.jp/ecoli/pec/genes.List.DetailAction.do (Printed Dec. 21, 2009).

URL_www.genome.jp/dbget-bin/www_bget?ctc:CTC01366 (Printed Dec. 21, 2009).

URL_www.genome.jp/dbget-bin/www_bget?cpe:CPE2531 (Printed Dec. 21, 2009).

URL_www.genome.jp/dbget-bin/www_bget?cdf:CD2966 (Printed Dec. 21, 2009).

URL_www.genome.jp/dbget-bin/www_bget?cth:Cthe_0423 (Printed Mar. 4, 2010).

Genbank Accession No. L21902.1; GI No. 1228100 (Mar. 15, 1996).

Genbank Accession No. NP_149199.1; GI No. 15004739 (Mar. 30, 2006).

Genbank Accession No. NP_149325.1; GI No. 15004865 (Mar. 30, 2006).

Genbank Accession No. YP_726053.1; GI No. 113867564 (Oct. 26, 2006).

Genbank Accession No. NP_349891.1; GI No. 15896542 (Jan. 18, 2006).

Genbank Accession No. NP_349676.1; GI No. 15896327 (Jan. 18, 2006).

Genbank Accession No. Q45829; GI No. 20137334 (Dec. 12, 2006).

Genbank Accession No. Q97II1; GI No. 20137415 (Dec. 12, 2006).

Genbank Accession No. AAT48939.1; GI No. 49036681 (Jun. 27, 2004).

Genbank Accession No. NP_349892.1; GI No. 15896543 (Jan. 18, 2006).

Genbank Accession No. AAP42563.1; GI No. 31075383 (Jan. 24, 2007).

Genbank Accession No. BAF45463.1; GI No. 124221917 (Jan. 26, 2007).

Genbank Accession No. YP_977400.1; GI No. 121637177 (Jan. 11, 2007).

Genbank Accession No. CAB60036.1; GI No. 6249316 (Jul. 16, 2005).

Genbank Accession No. NP_906037.1; GI No. 34541558 (Jan. 18, 2006).

Genbank Accession No. NP_904963.1; GI No. 34540484 (Jan. 18, 2006).

Genbank Accession No. NP_904964.1; GI No. 34540485 (Jan. 18, 2006).

Genbank Accession No. AF148264.1; GI No. 5916168 (May 13, 2004).

Abiko et al., "Localization of NAD-isocitrate dehydrogenase and glutamate dehydrogenase in rice roots: candidates for providing carbon skeletons to NADH-glutamate synthase," *Plant Cell Physiol.* 46(10):1724-1734 (2005).

Bergquist and Gibbs, "Degenerate oligonucleotide gene shuffling," *Methods Mol. Biol.* 352:191-204 (2007).

Binstock and Schulz, "Fatty acid oxidation complex from *Escherichia coli*," *Methods Enzymo.* 71 Pt C:403-411 (1981).

Bravo et al., "Reliable, sensitive, rapid and quantitative enzyme-based assay for gamma-hydroxybutyric acid (GHB)," *J. Forensic. Sci.* 49(2):379-387 (2004).

Cooper, "Glutamate-γ-aminobutyrate transaminase," *Methods Enzymol.* 113:80-82 (1985).

Jacobi et al., "The *hyp* operon gene products are required for the maturation of catalytically active hydrogenase isoenzymes in *Escherichia coli*," *Arch. Microbiol.* 158:444-451 (1992).

Kim et al., "Dihydrolipoamide Dehydrogenase Mutation Alters the NADH Sensitivity of Pyruvate Dehydrogenase Complex of *Escherichi coli* K-12," *J. Bacteriol.* 190:3851-3858 (2008).

Knappe and Sawers, "A radical-chemical route to acetyl-CoA: the anaerobically induced pyruvate formate-lyase system of *Escherichia coli*," *FEMS Microbiol. Rev.* 75:383-398 (1990).

Lutz et al., "Rapid generation of incremental truncation libraries for protein engineering using α-phosphothioate nucleotides," *Nucleic Acids Res.* 15:29(4):e16 (2001).

Onuffer and Kirsch, "Redesign of the substrate specificity of *Escherichia coli* aspartate aminotransferase to that of *Escherichia coli* tyrosine aminotransferase by homology modeling and site-directed mutagenesis," *Protein Sci.* 4:1750-1757 (1995).

Pierce et al.,"The complete genome sequence of *Moorella thermoacetia* (f. *Clostridium thermoaceticum*)," *Environ. Microbiol.* 10(10):2550-2573 (2008).

Rathinasabapathi, Propionate, a source of β-alanine, is an inhibitor of β-alanine methylation in *Limonium latifolium*, Plumbaginaceae *J. Plant Physiol.* 159:671-674 (2002).

Reetz et al., "Expanding the Range of Substrate Acceptance of Enzymes: Combinatorial Active-site saturation test," *Agnew. Chem. Int. Ed. Engl.* 44:4192-4196 (2005).

Ringquist et al., "Translation initiation in *Escherichia coli*: sequences within the ribosome-binding site," *Mol. Microbiol.* 6:1219-1229 (1992).

Roca et al., "Metabolic engineering of ammonium assimilation in xylose-fermenting *Saccharmyces cerevisiae* improves ethanol production," *Appl. Environ. Microbiol.* 69(8):4732-4736 (2003).

Suthers et al., "Metabolic flux elucidation for large-scale models using $^{13}C$ labeled isotopes," *Metab. Eng.* 9(5-6):387-405 (2007).

Takahashi et al., "Metabolic Pathways for Cytoxic End Product Formation from Glutamate- and Aspartate-Containing Peptides by *Porphyromonas gingivalis*," *J. Bacteriol.* 182(17):4704-4710 (2000).

Venkitasubramanian et al., "Ch. 15: Biocatalytic Reduction of Carboxylic Acids: Mechanism and Applications," In R.N. Patel (ed.), *Biocatalysis in the Pharmaceutical and Biotechnology Industries*, CRC Press LLC, Boca Raton, FL (2006).

Viola, "L-aspartase: new tricks from an old enzyme," *Adv. Enzymol. Relat. Areas. Mol. Biol.* 74:295-341 (2000).

Ward et al., "Molecular analysis of the role of two aromatic aminotransferases and a broad-specificity aspartate aminotransferase in the aromatic amino acid metabolism of *Pyrococcus furiosus*," *Archaea* 1:133-141 (2002).

Wexler et al., "A Wide host-range metagenomic library from a waste water treatment plant yields a novel alcohol/aldehyde dehdrogenae," *Environ. Microbiol.* 7:1917-1926 (2005).

Wong et al., "Transversion-enriched sequence saturation mutagenesis (SeSaM-Tv$^+$): a random mutagenesis method with consecutive nucleotide exchanges that complements the bias of error-prone PCR," *Biotechnol. J.* 3(1):74-82 (2008).

Yagi et al., "Glutamate-Aspartate Transaminase from Microorganisms," *Meth. Enzymol.* 113:83-89 (1985).

Yamamoto et al., "Carboxylation reaction catalyzed by 2-oxoglutarate:ferredoxin oxidoreductases from *Hydrogenobacter thermophilus*," *Extremophiles* 14:79-85 (2010).

Bradford, "A rapid and sensitive method for the quantitation of microgram quantities of protein utilizing the principle of protein-dye binding," *Anal. Biochem.* 72:248-254 (1976).

Drake, "Acetogenesis, acetogenic bacteria, and the acetyl-CoA "Wood/Ljungdahl" pathway: past and current perspectives," In H.L. Drake (ed.), *Acetogenesis* pp. 3-60 Chapman and Hall, New York (1994).

Hughes et al., "Evidence for Isofunctional Enzymes in the Degradation of Phenol, *m*- and *p*-Toulate, and *p*-Cresol via Catechol meta-Cleavage Pathways in *Alcaligenes eutrophus*," *J. Bacteriol.* 158:79-83 (1984).

Hugler et al., "Malonyl-coenzyme A reductase from *Chioroflexus aurantiacus*, a key enzyme of the 3-hydroxypropionate cycle for autotrophic CO(2) fixation," *J.Bacteriol.* 184:2404-2410 (2002).

Huisman and Lalonde, "Ch. 30: Enzyme Evolution for Chemical Process Applications," In R N. Patel (ed.), *Biocatalysis in the pharmaceutical and biotechnology industries*, CRC Press, Boca Raton, FL, p. 717-742 (2007).

Kwon et al., "Influence of gluconeogenic phosphoenolpyruvate carboxykinase (PCK) expression on succinic acid fermentation in *Escherichia coli* under high bicarbonate condition," *J. Microbiol. Biotechno.*, 16(9):1448-1452 (2006).

Li and Jordan, "Effects of Substitution of Tryptophan 412 in the Substrate Activation Pathway of Yeast Pyruvate Decarboxylase," *Biochemistry* 38:10004-10012 (1999).

Menzel et al., "Enzymatic evidence for an involvement of pyruvate dehydrogenase in the anaerobic glycerol metabolism of *Klebsiella pneumoniae*," *J. Biotechnol.* 56:135-142 (1997).

Orencio-Trejo et al., "Metabolic regluation analysis of an ethanologenic *Escherichia coli* strain based on RT-PCR and enzymatic activities," *Biotechnol. Biofuels* 1:8 (2008).

Ploux et al., "The NADPH-linked acetoacetyl-CoA reductase from *Zoogloea ramigera*, Characterization and mechanistic studies of the cloned enzyme over-produced in *Escherichia coli*," Eur. *J. Biochem.* 174:177-182 (1988).

Bermejo et al., "Expression of *Clostridium acetobutylicum* ATCC 824 Genes in *Escherichia coli* for Acetone Production and Acetate Detoxification," *Appl. Environ. Microbiol.* 64(3):1079-1085 (1998).

Birrer et al., "Electro-transformation of *Clostridium beijerinckii* NRRL B-592 with shuttle plasmid pHR106 and recombinant derivatives," *Appl. Microbiol. Biotechnol.* 41(1):32-38 (1994).

Chen and Hiu, "Acetone-Butanol-Isopropanol Production by *Clostridium beijerinckii* (Synonym, *Clostridium butylicum*)," *Biotechnology Letters* 8(5):371-376 (1986).

Clark, Progress Report for Department of Energy Grant DE-FG02-88ER13941, "Regulation of Alcohol Fermentation in *Escherichia coli*," pp. 1-7 for the period: Jul. 1991-Jun. 1994.

Durre and Bahl, "Microbial Production of Acetone/Butanol/Isopropanol," In *Biotechnology* vol. 6: "Products of Primary Metabolism", Second edition pp. 229-268, M. Roehr, ed. Published jointly by: VCH Verlagsgesellschaft mbH, Weinheim, Federal Republic of Germany and VCH Publishers Inc., New York, NY (1996).

Dürre, "New insights and novel developments in clostridial acetone/butanol/isopropanol fermentation," *Appl. Microbiol. Biotechnol.* 49:639-648 (1998).

Gerischer and Dürre, "mRNA Analysis of the *adc* Gene Region of *Clostridium acetobutylicum* during the Shift to Solventogenesis," *J. Bacteriol.*174(2):426-433 (1992).

Li, Guang-Shan, "Development of a reporter system for the study of gene expression for solvent production in *Clostridium beijerinckii* NRRL B592 and *Clostridium acetobutylicum* ATCC 824," Dissertation, Department of Biochemestry, Virginia Polytechnic Institute and State University (Sep. 1998).

Mermelstein et al., "Metabolic Engineering of *Clostridium acetobutylicum* ATCC 824 for Increased Solvent Production by Enhancement of Acetone Formation Enzyme Activities Using a Synthetic Acetone Operon," *Biotechnol. Bioeng.* 42(9):1053-1060 (1993).

* cited by examiner

US 8,067,214 B2

COMPOSITIONS AND METHODS FOR THE BIOSYNTHESIS OF 1,4-BUTANEDIOL AND ITS PRECURSORS

This application claims the benefit of priority of U.S. Provisional application Ser. No. 60/918,463, filed Mar. 16, 2007, the entire contents of which are incorporated herein by reference.

BACKGROUND OF THE INVENTION

This invention relates generally to in silico design of organisms and, more particularly to organisms having 1,4-butanediol biosynthesis capability.

The compound 4-hydroxybutanoic acid (4-hydroxybutanoate, 4-hydroxybutyrate, 4-HB) is a 4-carbon carboxylic acid that has industrial potential as a building block for various commodity and specialty chemicals. In particular, 4-HB has the potential to serve as a new entry point into the 1,4-butanediol family of chemicals, which includes solvents, resins, polymer precursors, and specialty chemicals. 1,4-Butanediol (BDO) is a polymer intermediate and industrial solvent with a global market of about 3 billion lb/year. BDO is currently produced from petrochemical precursors, primarily acetylene, maleic anhydride, and propylene oxide.

For example, acetylene is reacted with 2 molecules of formaldehyde in the Reppe synthesis reaction (Kroschwitz and Grant, *Encyclopedia of Chem. Tech.*, John Wiley and Sons, Inc., New York (1999)), followed by catalytic hydrogenation to form 1,4-butanediol. It has been estimated that 90% of the acetylene produced in the U.S. is consumed for butanediol production. Alternatively, it can be formed by esterification and catalytic hydrogenation of maleic anhydride, which is derived from butane. Downstream, butanediol can be further transformed; for example, by oxidation to □-butyrolactone, which can be further converted to pyrrolidone and N-methyl-pyrrolidone, or hydrogenolysis to tetrahydrofuran (FIG. 1). These compounds have varied uses as polymer intermediates, solvents, and additives, and have a combined market of nearly 2 billion lb/year.

It is desirable to develop a method for production of these chemicals by alternative means that not only substitute renewable for petroleum-based feedstocks, and also use less energy- and capital-intensive processes. The Department of Energy has proposed 1,4-diacids, and particularly succinic acid, as key biologically-produced intermediates for the manufacture of the butanediol family of products (DOE Report, "Top Value-Added Chemicals from Biomass", 2004). However, succinic acid is costly to isolate and purify and requires high temperatures and pressures for catalytic reduction to butanediol.

Thus, there exists a need for alternative means for effectively producing commercial quantities of 1,4-butanediol and its chemical precursors. The present invention satisfies this need and provides related advantages as well.

SUMMARY OF THE INVENTION

The invention provides a non-naturally occurring microbial biocatalyst including a microbial organism having a 4-hydroxybutanoic acid (4-HB) biosynthetic pathway having at least one exogenous nucleic acid encoding 4-hydroxybutanoate dehydrogenase, succinyl-CoA synthetase, CoA-dependent succinic semialdehyde dehydrogenase, or α-ketoglutarate decarboxylase, wherein the exogenous nucleic acid is expressed in sufficient amounts to produce monomeric 4-hydroxybutanoic acid (4-HB). Also provided is a non-naturally occurring microbial biocatalyst including a microbial organism having 4-hydroxybutanoic acid (4-HB) and 1,4-butanediol (BDO) biosynthetic pathways, the pathways include at least one exogenous nucleic acid encoding 4-hydroxybutanoate dehydrogenase, succinyl-CoA synthetase, CoA-dependent succinic semialdehyde dehydrogenase, 4-hydroxybutyrate:CoA transferase, 4-butyrate kinase, phosphotransbutyrylase, α-ketoglutarate decarboxylase, aldehyde dehydrogenase, alcohol dehydrogenase or an aldehyde/alcohol dehydrogenase, wherein the exogenous nucleic acid is expressed in sufficient amounts to produce 1,4-butanediol (BDO). Additionally provided is a method for the production of 4-HB. The method includes culturing a non-naturally occurring microbial organism having a 4-hydroxybutanoic acid (4-HB) biosynthetic pathway including at least one exogenous nucleic acid encoding 4-hydroxybutanoate dehydrogenase, succinyl-CoA synthetase, CoA-dependent succinic semialdehyde dehydrogenase or α-ketoglutarate decarboxylase under substantially anaerobic conditions for a sufficient period of time to produce monomeric 4-hydroxybutanoic acid (4-HB). Further provided is a method for the production of BDO. The method includes culturing a non-naturally occurring microbial biocatalyst, comprising a microbial organism having 4-hydroxybutanoic acid (4-HB) and 1,4-butanediol (BDO) biosynthetic pathways, the pathways including at least one exogenous nucleic acid encoding 4-hydroxybutanoate dehydrogenase, succinyl-CoA synthetase, CoA-dependent succinic semialdehyde dehydrogenase, 4-hydroxybutyrate:CoA transferase, 4-hydroxybutyrate kinase, phosphotranshydroxybutyrylase, α-ketoglutarate decarboxylase, aldehyde dehydrogenase, alcohol dehydrogenase or an aldehyde/alcohol dehydrogenase for a sufficient period of time to produce 1,4-butanediol (BDO). The 4-HB and/or BDO products can be secreted into the culture medium.

DETAILED DESCRIPTION OF THE INVENTION

Figure 1:
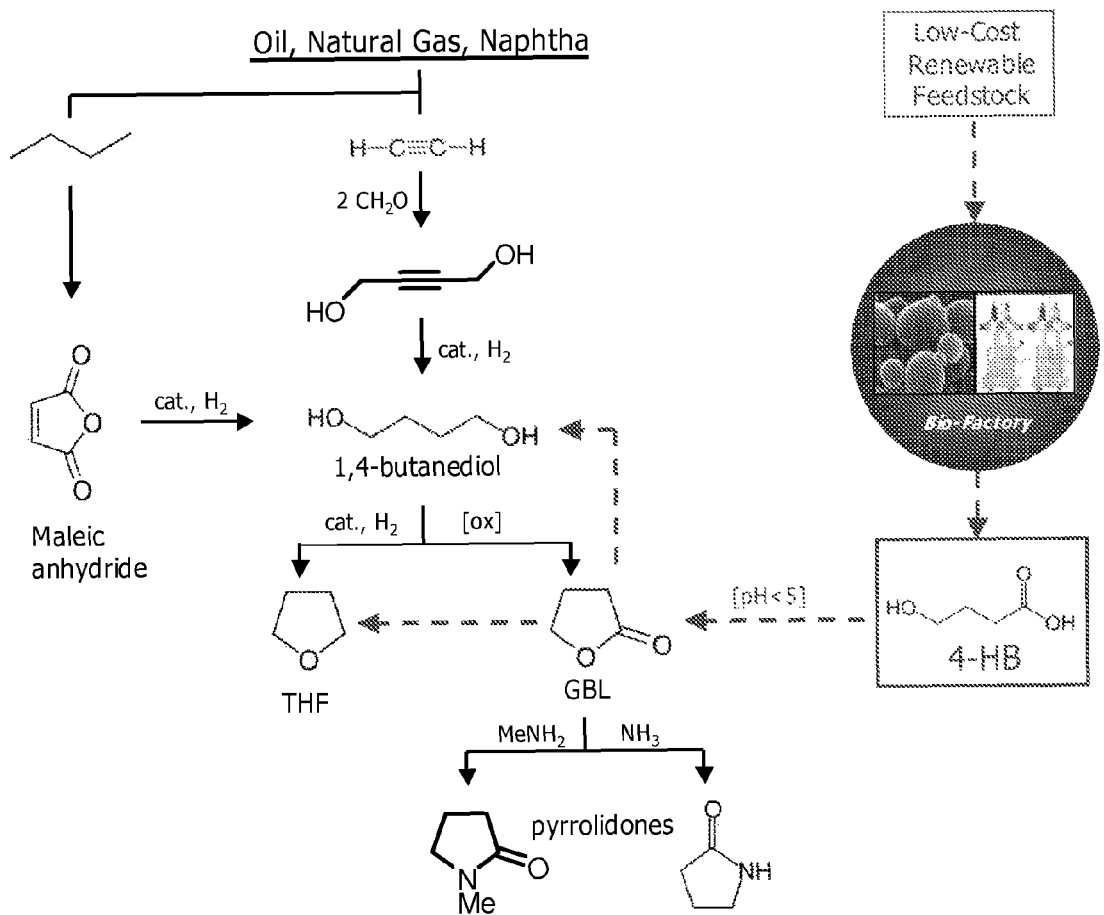
FIG. 1 is a schematic diagram showing an entry point of 4-hydroxybutanoic acid (4-HB) into the product pipeline of the 1,4-butanediol (BDO) family of chemicals, and comparison with chemical synthesis routes from petrochemical feedstocks. Solid black arrows show chemical synthesis routes; dashed blue arrows show a biosynthetic route to 4-HB and subsequent conversion steps to BDO family chemicals.

This invention is directed to the design and production of cells and organisms having biosynthetic production capabilities for 4-hydroxybutanoic acid (4-HB), γ-butyrolactone and 1,4-butanediol. In one embodiment, the invention utilizes in silico stoichiometric models of *Escherichia coli* metabolism that identify metabolic designs for biosynthetic production of 4-hydroxybutanoic acid (4-HB) and 1,4-butanediol (BDO). The results described herein indicate that metabolic pathways can be designed and recombinantly engineered to achieve the biosynthesis of 4-HB and downstream products such as 1,4-butanediol in *Escherichia coli* and other cells or organisms. Biosynthetic production of 4-HB, for example, for the in silico designs can be confirmed by construction of strains having the designed metabolic genotype. These metabolically engineered cells or organisms also can be subjected to adaptive evolution to further augment 4-HB biosynthesis, including under conditions approaching theoretical maximum growth.

In certain embodiments, the 4-HB biosynthesis characteristics of the designed strains make them genetically stable and particularly useful in continuous bioprocesses. Separate strain design strategies were identified with incorporation of different non-native or heterologous reaction capabilities into *E. coli* leading to 4-HB and 1,4-butanediol producing metabolic pathways from either CoA-independent succinic semialdehyde dehydrogenase, succinyl-CoA synthetase and CoA-dependent succinic semialdehyde dehydrogenase, or glutamate:succinic semialdehyde transaminase. In silico metabolic designs were identified that resulted in the biosynthesis of 4-HB in both *E. coli* and yeast species from each of these metabolic pathways. The 1,4-butanediol intermediate γ-butyrolactone can be generated in culture by spontaneous cyclization under conditions at pH<7.5, particularly under acidic conditions, such as below pH 5.5, for example, pH<7, pH<6.5, pH<6, and particularly at pH<5.5 or lower.

Strains identified via the computational component of the platform can be put into actual production by genetically engineering any of the predicted metabolic alterations which lead to the biosynthetic production of 4-HB, 1,4-butanediol or other intermediate and/or downstream products. In yet a further embodiment, strains exhibiting biosynthetic production of these compounds can be further subjected to adaptive evolution to further augment product biosynthesis. The levels of product biosynthesis yield following adaptive evolution also can be predicted by the computational component of the system.

In other specific embodiments, microbial organisms were constructed to express a 4-HB biosynthetic pathway encoding the enzymatic steps from succinate to 4-HB and to 4-HB-CoA. Co-expression of succinate coenzyme A transferase, CoA-dependent succinic semialdehyde dehydrogenase, NAD-dependent 4-hydroxybutyrate dehydrogenase and 4-hydroxybutyrate coenzyme A transferase in a host microbial organism resulted in significant production of 4-HB compared to host microbial organisms lacking a 4-HB biosynthetic pathway. In a further specific embodiment, 4-HB-producing microbial organisms were generated that utilized α-ketoglutarate as a substrate by introducing nucleic acids encoding α-ketoglutarate decarboxylase and NAD-dependent 4-hydroxybutyrate dehydrogenase.

In another specific embodiment, microbial organisms containing a 1,4-butanediol (BDO) biosynthetic pathway were constructed that biosynthesized BDO when cultured in the presence of 4-HB. The BDO biosynthetic pathway consisted of a nucleic acid encoding either a multifunctional aldehyde/alcohol dehydrogenase or nucleic acids encoding an aldehyde dehydrogenawse and an alcohol dehydrogenase. To support growth on 4-HB substrates, these BDO-producing microbial organisms also expressed 4-hydroxybutyrate CoA transferase or 4-butyrate kinase in conjunction with phosphotranshydroxybutyrlase. In yet a further specific embodiment, microbial organisms were generated that synthesized BDO through exogenous expression of nucleic acids encoding a functional 4-HB biosynthetic pathway and a functional BDO biosynthetic pathway. The 4-HB biosynthetic pathway consisted of succinate coenzyme A transferase, CoA-dependent succinic semialdehyde dehydrogenase, NAD-dependent 4-hydroxybutyrate dehydrogenase and 4-hydroxybutyrate coenzyme A transferase. The BDO pathway consisted of a multifunctional aldehyde/alcohol dehydrogenase.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial genetic material. Such modification include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes within a 4-HB biosynthetic pathway and enzymes within a biosynthetic pathway for a BDO family of compounds.

A metabolic modification refers to a biochemical reaction that is altered from its naturally occurring state. Therefore, non-naturally occurring microorganisms having genetic modifications to nucleic acids encoding metabolic polypeptides or, functional fragments thereof. Exemplary metabolic modifications are described further below for both E. coli and yeast microbial organisms.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" is intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "4-hydroxybutanoic acid" is intended to mean a 4-hydroxy derivative of butyric acid having the chemical formula $C_4H_8O_3$ and a molecular mass of 104.11 g/mol (126.09 g/mol for its sodium salt). The chemical compound 4-hydroxybutanoic acid also is known in the art as 4-HB, 4-hydroxybutyrate, gamma-hydroxybutyric acid or GHB. The term as it is used herein is intended to include any of the compound's various salt forms and include, for example, 4-hydroxybutanoate and 4-hydroxybutyrate. Specific examples of salt forms for 4-HB include sodium 4-HB and potassium 4-HB. Therefore, the terms 4-hydroxybutanoic acid, 4-HB, 4-hydroxybutyrate, 4-hydroxybutanoate, gamma-hydroxybutyric acid and GHB as well as other art recognized names are used synonymously herein.

As used herein, the term "monomeric" when used in reference to 4-HB is intended to mean 4-HB in a non-polymeric or underivatized form. Specific examples of polymeric 4-HB include poly-4-hydroxybutanoic acid and copolymers of, for example, 4-HB and 3-HB. A specific example of a derivatized form of 4-HB is 4-HB-CoA. Other polymeric 4-HB forms and other derivatized forms of 4-HB also are known in the art.

As used herein, the term "γ-butyrolactone" is intended to mean a lactone having the chemical formula $C_4H_6O_2$ and a molecular mass of 86.089 g/mol. The chemical compound γ-butyrolactone also is know in the art as GBL, butyrolactone, 1,4-lactone, 4-butyrolactone, 4-hydroxybutyric acid lactone, and gamma-hydroxybutyric acid lactone. The term as it is used herein is intended to include any of the compound's various salt forms.

As used herein, the term "1,4-butanediol" is intended to mean an alcohol derivative of the alkane butane, carrying two hydroxyl groups which has the chemical formula $C_4H_{10}O_2$ and a molecular mass of 90.12 g/mol. The chemical compound 1,4-butanediol also is known in the art as BDO and is a chemical intermediate or precursor for a family of compounds referred to herein as BDO family of compounds, some of which are exemplified in FIG. 1.

As used herein, the term "tetrahydrofuran" is intended to mean a heterocyclic organic compound corresponding to the fully hydrogenated analog of the aromatic compound furan which has the chemical formula $C_4H_8O$ and a molecular mass of 72.11 g/mol. The chemical compound tetrahydrofuran also is known in the art as THF, tetrahydrofuran, 1,4-epoxybutane, butylene oxide, cyclotetramethylene oxide, oxacyclopentane, diethylene oxide, oxolane, furanidine, hydrofuran, tetra-methylene oxide. The term as it is used herein is intended to include any of the compound's various salt forms.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

The non-naturally occurring microbal organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein are described with reference to *E. coli* and yeast genes and their corresponding metabolic reactions. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the growth-coupled production of a biochemical product, those skilled in the art will understand that the orthologous gene harboring the metabolic activity to be disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene compared to a gene encoding the function sought to be substituted. Therefore, a nonorthologous gene includes, for example, a paralog or an unrelated gene.

Therefore, in identifying and constructing the non-naturally occurring microbial organisms of the invention having 4-HB, GBL and/or BDO biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionally related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

The invention provides a non-naturally occurring microbial biocatalyst including a microbial organism having a 4-hydroxybutanoic acid (4-HB) biosynthetic pathway that includes at least one exogenous nucleic acid encoding 4-hydroxybutanoate dehydrogenase, CoA-independent succinic semialdehyde dehydrogenase, succinyl-CoA synthetase, CoA-dependent succinic semialdehyde dehydrogenase, glutamate:succinic semialdehyde transaminase, alpha-ketoglutarate decarboxylase, or glutamate decarboxylase, wherein the exogenous nucleic acid is expressed in sufficient amounts to produce monomeric 4-hydroxybutanoic acid (4-HB). 4-hydroxybutanoate dehydrogenase is also referred to as 4-hydroxybutyrate dehydrogenase or 4-HB dehydrogenase. Succinyl-CoA synthetase is also referred to as succinyl-CoA synthase or succinyl-CoA ligase.

Also provided is a non-naturally occurring microbial biocatalyst including a microbial organism having a 4-hydroxybutanoic acid (4-HB) biosynthetic pathway having at least one exogenous nucleic acid encoding 4-hydroxybutanoate dehydrogenase, succinyl-CoA synthetase, CoA-dependent succinic semialdehyde dehydrogenase, or α-ketoglutarate decarboxylase, wherein the exogenous nucleic acid is expressed in sufficient amounts to produce monomeric 4-hydroxybutanoic acid (4-HB).

The non-naturally occurring microbial biocatalysts of the invention include microbial organisms that employ combinations of metabolic reactions for biosynthetically producing the compounds of the invention. The biosynthesized compounds can be produced intracellularly and/or secreted into the culture medium. Exemplary compounds produced by the non-naturally occurring microorganisms include, for example, 4-hydroxybutanoic acid, 1,4-butanediol and γ-butyrolactone. The relationships of these exemplary compounds with respect to chemical synthesis or biosynthesis are exemplified in FIG. 1.

In one embodiment, a non-naturally occurring microbial organism is engineered to produce 4-HB. This compound is one useful entry point into the 1,4-butanediol family of compounds. The biochemical reactions for formation of 4-HB from succinate, from succinate through succinyl-CoA or from α-ketoglutarate are shown in steps 1-8 of FIG. 2.

The invention is described herein with general reference to the metabolic reaction, reactant or product thereof, or with specific reference to one or more nucleic acids or genes encoding an enzyme associated with or catalyzing the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction and that reference to any of these metabolic constitutes also references the gene or genes encoding the enzymes that catalyze the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes as well as the reactants and products of the reaction.

The production of 4-HB via biosynthetic modes using the microbial organisms of the invention is particularly useful because it can produce monomeric 4-HB. The non-naturally occurring microbial organisms of the invention and their biosynthesis of 4-HB and BDO family compounds also is particularly useful because the 4-HB product is (1) secreted; (2) can be devoid of any derivatizations such as Coenzyme A; (3) avoids thermodynamic changes during biosynthesis; (4) allows direct biosynthesis of BDO, and (5) allows for the spontaneous chemical conversion of 4-HB to γ-butyrolactone (GBL) in acidic pH medium. This latter characteristic also is particularly useful for efficient chemical synthesis or biosynthesis of BDO family compounds such as 1,4-butanediol and/or tetrahydrofuran (THF), for example.

Microbial organisms generally lack the capacity to synthesize 4-HB and therefore, any of the compounds shown in FIG. 1 are known to be within the 1,4-butanediol family of compounds or known by those in the art to be within the 1,4-butanediol family of compounds. Moreover, organisms having all of the requisite metabolic enzymatic capabilities are not known to produce 4-HB from the enzymes described and biochemical pathways exemplified herein. Rather, with the possible exception of a few anaerobic microorganisms described further below, the microorganisms having the enzymatic capability use 4-HB as a substrate to produce, for example, succinate. In contrast, the non-naturally occurring microbial organisms of the invention generate 4-HB as a product. As described above, the biosynthesis of 4-HB in its monomeric form is not only particularly useful in chemical synthesis of BDO family of compounds, it also allows for the further biosynthesis of BDO family compounds and avoids altogether chemical synthesis procedures.

The non-naturally occurring microbial organisms of the invention that can produce 4-HB are produced by ensuring that a host microbial organism includes functional capabilities for the complete biochemical synthesis of at least one 4-HB biosynthetic pathway of the invention. Ensuring at least one requisite 4-HB biosynthetic pathway confers 4-HB biosynthesis capability onto the host microbial organism.

Figure 2:
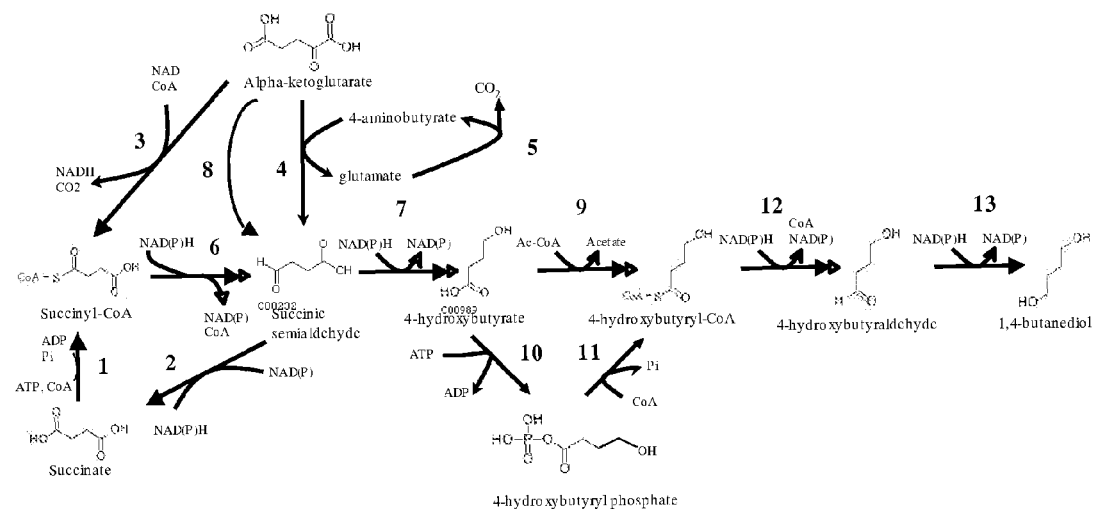
FIG. 2 is a schematic diagram showing biochemical pathways to 4-hydroxybutyurate (4-HB) and to 1,4-butanediol production. The first 5 steps are endogenous to *E. coli*, while the remainder can be expressed heterologously. Enzymes catalyzing the biosynthetic reactions are: (1) succinyl-CoA synthetase; (2) CoA-independent succinic semialdehyde dehydrogenase; (3) α-ketoglutarate dehydrogenase; (4) glutamate:succinate semialdehyde transaminase; (5) glutamate decarboxylase; (6) CoA-dependent succinic semialdehyde dehydrogenase; (7) 4-hydroxybutanoate dehydrogenase; (8) α-ketoglutarate decarboxylase; (9) 4-hydroxybutyryl CoA:acetyl-CoA transferase; (10) butyrate kinase; (11) phosphotransbutyrylase; (12) aldehyde dehydrogenase; (13) alcohol dehydrogenase.

Five requisite 4-HB biosynthetic pathways are exemplified herein and shown for purposes of illustration in FIG. 2. One requisite 4-HB biosynthetic pathway includes the biosynthesis of 4-HB from succinate (the succinate pathway). The enzymes participating in this 4-HB pathway include CoA-independent succinic semialdehyde dehydrogenase and 4-hydroxybutanoate dehydrogenase. In this pathway, CoA-independent succinic semialdehyde dehydrogenase catalyzes the reverse reaction to the arrow shown in FIG. 2. Another requisite 4-HB biosynthetic pathway includes the biosynthesis from succinate through succinyl-CoA (the succinyl-CoA pathway). The enzymes participating in this 4-HB pathway include succinyl-CoA synthetase, CoA-dependent succinic semialdehyde dehydrogenase and 4-hydroxybutanoate dehydrogenase. Three other requisite 4-HB biosynthetic pathways include the biosynthesis of 4-HB from α-ketoglutarate (the α-ketoglutarate pathways). Hence, a third requisite 4-HB biosynthetic pathway is the biosynthesis of succinic semialdehyde through glutamate:succinic semialdehyde transaminase, glutamate decarboxylase and 4-hydroxybutanoate dehydrogenase. A fourth requisite 4-HB biosynthetic pathway also includes the biosynthesis of 4-HB from α-ketoglutarate, but utilizes α-ketoglutarate decarboxylase to catalyze succinic semialdehyde synthesis. 4-hydroxybutanoate dehydrogenase catalyzes the conversion of succinic semialdehyde to 4-HB. A fifth requisite 4-HB biosynthetic pathway includes the biosynthesis from α-ketoglutarate through succinyl-CoA and utilizes α-ketoglutarate dehydrogenase to produce succinyl-CoA, which funnels into the succinyl-CoA pathway described above. Each of these 4-HB biosynthetic pathways, their substrates, reactants and products are described further below in the Examples.

The non-naturally occurring microbial organisms of the invention can be produced by introducing expressible nucleic acids encoding one or more of the enzymes participating in one or more 4-HB biosynthetic pathways. Depending on the host microbial organism chosen for biosynthesis, nucleic acids for some or all of a particular 4-HB biosynthetic pathway can be expressed. For example, if a chosen host is deficient in both enzymes in the succinate to 4-HB pathway and this pathway is selected for 4-HB biosynthesis, then expressible nucleic acids for both CoA-independent succinic semialdehyde dehydrogenase and 4-hydroxybutanoate dehydrogenase are introduced into the host for subsequent exogenous expression. Alternatively, if the chosen host exhibits endogenous CoA-independent succinic semialdehyde dehydrogenase, but is deficient in 4-hydroxybutanoate dehydrogenase then an encoding nucleic acid is needed for this enzyme to achieve 4-HB biosynthesis.

In like fashion, where 4-HB biosynthesis is selected to occur through the succinate to succinyl-CoA pathway (the succinyl-CoA pathway), encoding nucleic acids for host deficiencies in the enzymes succinyl-CoA synthetase, CoA-dependent succinic semialdehyde dehydrogenase and/or 4-hydroxybutanoate dehydrogenase are to be exogenously expressed in the recipient host. Selection of 4-HB biosynthesis through the α-ketoglutarate to succinic semialdehyde pathway (the α-ketoglutarate pathway) can utilize exogenous expression for host deficiencies in one or more of the enzymes for glutamate:succinic semialdehyde transaminase, glutamate decarboxylase and/or 4-hydroxybutanoate dehydrogenase, or α-ketoglutarate decarboxylase and 4-hydroxybutanoate dehydrogenase.

Depending on the 4-HB biosynthetic pathway constituents of a selected host microbial organism, the non-naturally occurring microbial 4-HB biocatalysts of the invention will include at least one exogenously expressed 4-HB pathway-encoding nucleic acid and up to all encoding nucleic acids for one or more 4-HB biosynthetic pathways. For example, 4-HB biosynthesis can be established from all five pathways in a host deficient in 4-hydroxybutanoate dehydrogenase through exogenous expression of a 4-hydroxybutanoate dehydrogenase encoding nucleic acid. In contrast, 4-HB biosynthesis can be established from all five pathways in a host deficient in all eight enzymes through exogenous expression of all eight of CoA-independent succinic semialdehyde dehydrogenase, succinyl-CoA synthetase, CoA-dependent succinic semialdehyde dehydrogenase, glutamate:succinic semialdehyde transaminase, glutamate decarboxylase, α-ketoglutarate decarboxylase, α-ketoglutarate dehydrogenase and 4-hydroxybutanoate dehydrogenase.

Given the teachings and guidance provided herein, those skilled in the art will understand that the number of encoding nucleic acids to introduce in an expressible form will, at least, parallel the 4-HB pathway deficiencies of the selected host microbial organism. Therefore, a non-naturally occurring microbial organism of the invention can have one, two, three, four, five, six, seven or eight nucleic acids encoding the above enzymes constituting one or more 4-HB biosynthetic pathways. In some embodiments, the non-naturally occurring microbial organisms also can include other genetic modifications that facilitate or optimize 4-HB biosynthesis or that confer other useful functions onto the host microbial organism. One such other functionality can include, for example, augmentation of the synthesis of one or more of the 4-HB pathway precursors such as succinate, succinyl-CoA and/or α-ketoglutarate.

In some embodiments, a non-naturally occurring microbial organism of the invention is generated from a host that contains the enzymatic capability to synthesize 4-HB. In this specific embodiment it can be useful to increase the synthesis or accumulation of a 4-HB pathway product to, for example, drive 4-HB pathway reactions toward 4-HB production. Increased synthesis or accumulation can be accomplished by, for example, overexpression of nucleic acids encoding one or more of the above-described 4-HB pathway enzymes. Over expression of the 4-HB pathway enzyme or enzymes can occur, for example, through exogenous expression of the endogenous gene or genes, or through exogenous expression of the heterologous gene or genes. Therefore, naturally occurring organisms can be readily generated to be non-naturally 4-HB producing microbial organisms of the invention through overexpression of one, two, three, four, five or all six nucleic acids encoding 4-HB biosynthetic pathway enzymes. In addition, a non-naturally occurring organism can be generated by mutagenesis of an endogenous gene that results in an increase in activity of an enzyme in the 4-HB biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism (see Examples II and IV, for example).

"Exogenous" as it is used herein is intended to mean that the referenced molecule or the referenced activity is introduced into the host microbial organism including, for example, introduction of an encoding nucleic acid into the host genetic material such as by integration into a host chromosome. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

Sources of encoding nucleic acids for a 4-HB pathway enzyme can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *E. coli, Saccharomyces cerevisiae, Clostridium kluyveri, Clostridium acetobutylicum, Clostridium beijerinckii, Clostridium saccharoperbutylacetonicum, Clostridium perfringens, Clostridium difficile, Ralstonia eutropha, Mycobacterium bovis, Mycobacterium tuberculosis* and *Porphyromonas gingivalis*. For example, the microbial organisms having 4-HB biosynthetic production are exemplified herein with reference to *E. coli* and yeast hosts. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite 4-HB biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations enabling biosynthesis of 4-HB and other compounds of the invention described herein with reference to a particular organism such as *E. coli* or yeast can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative 4-HB biosynthetic pathway exists in an unrelated species, 4-HB biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual genes usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize monomeric 4-HB.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *E. coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger* and *Pichia pastoris*.

Methods for constructing and testing the expression levels of a non-naturally occurring 4-HB-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, Md. (1999). 4-HB and GBL can be separated by, for example, HPLC using a Spherisorb 5 ODS1 column and a mobile phase of 70% 10 mM phosphate buffer (pH=7) and 30% methanol, and detected using a UV detector at 215 nm (Hennessy et al. 2004, J. Forensic Sci. 46(6):1-9). BDO is detected by gas chromatography or by HPLC and refractive index detector using an Aminex HPX-87H column and a mobile phase of 0.5 mM sulfuric acid (Gonzalez-Pajuelo et al., *Met. Eng.* 7:329-336 (2005)).

For example, an expression vector or vectors can be constructed to harbor one or more 4-HB biosynthetic pathway and/or one or more BDO biosynthetic encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art.

The non-naturally occurring microbial organisms of the invention are constructed using methods well known in the art as exemplified above to exogenously express at least one nucleic acid encoding a 4-HB pathway enzyme in sufficient amounts to produce monomeric 4-HB. Exemplary levels of expression for 4-HB enzymes in each pathway are described further below in the Examples. Following the teachings and guidance provided herein, the non-naturally occurring microbial organisms of the invention can achieve biosynthesis of monomeric 4-HB resulting in intracellular concentrations between about 0.1-25 mM or more. Generally, the intracellular concentration of monomeric 4-HB is between about 3-20 mM, particularly between about 5-15 mM and more particularly between about 8-12 mM, including about 10 mM or more. Intracellular concentrations between and above each of these exemplary ranges also can be achieved from the non-naturally occurring microbial organisms of the invention.

As described further below, one exemplary growth condition for achieving biosynthesis of 4-HB includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The invention also provides a non-naturally occurring microbial biocatalyst including a microbial organism having 4-hydroxybutanoic acid (4-HB) and 1,4-butanediol (BDO) biosynthetic pathways that include at least one exogenous nucleic acid encoding 4-hydroxybutanoate dehydrogenase, CoA-independent succinic semialdehyde dehydrogenase, succinyl-CoA synthetase, CoA-dependent succinic semialdehyde dehydrogenase, 4-hydroxybutyrate:CoA transferase, glutamate:succinic semialdehyde transaminase, glutamate decarboxylase, CoA-independent aldehyde dehydrogenase, CoA-dependent aldehyde dehydrogenase or alcohol dehydrogenase, wherein the exogenous nucleic acid is expressed in sufficient amounts to produce 1,4-butanediol (BDO). 4-Hydroxybutyrate:CoA transferase also is known as 4-hydroxybutyryl CoA:acetyl-CoA transferase.

The invention further provides non-naturally occurring microbial biocatalyst including a microbial organism having 4-hydroxybutanoic acid (4-HB) and 1,4-butanediol (BDO) biosynthetic pathways, the pathways include at least one exogenous nucleic acid encoding 4-hydroxybutanoate dehydrogenase, succinyl-CoA synthetase, CoA-dependent succinic semialdehyde dehydrogenase, 4-hydroxybutyrate:CoA transferase, 4-butyrate kinase, phosphotransbutyrylase, α-ketoglutarate decarboxylase, aldehyde dehydrogenase, alcohol dehydrogenase or an aldehyde/alcohol dehydrogenase, wherein the exogenous nucleic acid is expressed in sufficient amounts to produce 1,4-butanediol (BDO).

Non-naturally occurring microbial organisms also can be generated which biosynthesize BDO. As with the 4-HB producing microbial organisms of the invention, the BDO producing microbial organisms also can produce intracellularly or secret the BDO into the culture medium. Following the teachings and guidance provided previously for the construction of microbial organisms that synthesize 4-HB, additional BDO pathways can be incorporated into the 4-HB producing microbial organisms to generate organisms that also synthesize BDO and other BDO family compounds. The chemical synthesis of BDO and its downstream products are illustrated in FIG. 1. The non-naturally occurring microbial organisms of the invention capable of BDO biosynthesis circumvent these chemical synthesis using 4-HB as an entry point as illustrated in FIG. 2. As described further below, the 4-HB producers also can be used to chemically convert 4-HB to GBL and then to BDO or THF, for example. Alternatively, the 4-HB producers can be further modified to include biosynthetic capabilities for conversion of 4-HB and/or GBL to BDO.

The additional BDO pathways to introduce into 4-HB producers include, for example, the exogenous expression in a host deficient background or the overexpression of one or more of the enzymes exemplified in FIG. 2 as steps 9-13. One such pathway includes, for example, the enzyme activities necessary to carryout the reactions shown as steps 9, 12 and 13 in FIG. 2, where the aldehyde and alcohol dehydrogenases can be separate enzymes or a multifunctional enzyme having both aldehyde and alcohol dehydrogenase activity. Another such pathway includes, for example, the enzyme activities necessary to carryout the reactions shown as steps 10, 11, 12 and 13 in FIG. 2, also where the aldehyde and alcohol dehydrogenases can be separate enzymes or a multifunctional enzyme having both aldehyde and alcohol dehydrogenase activity. Accordingly, the additional BDO pathways to introduce into 4-HB producers include, for example, the exogenous expression in a host deficient background or the overexpression of one or more of a 4-hydroxybutyrate:CoA transferase, butyrate kinase, phosphotransbutyrylase, CoA-independent aldehyde dehydrogenase, CoA-dependent aldehyde dehydrogenase or an alcohol dehydrogenase. In the absence of endogenous acyl-CoA synthetase capable of modifying 4-HB, the non-naturally occurring BDO producing microbial organisms can further include an exogenous acyl-CoA synthetase selective for 4-HB, or the combination of multiple enzymes that have as a net reaction conversion of 4-HB into 4-HB-CoA. As exemplified further below in the Examples, butyrate kinase and phosphotransbutyrylase exhibit BDO pathway activity and catalyze the conversions illustrated in FIG. 2 with a 4-HB substrate. Therefore, these enzymes also can be referred to herein as 4-hydroxybutyrate kinase and phosphotranshydroxybutyrylase respectively.

Exemplary alcohol and aldehyde dehydrogenases that can be used for these in vivo conversions from 4-HB to BDO are listed below in Table 1.

TABLE 1

Alcohol and Aldehyde Dehydrogenases for Conversion of 4-HB to BDO.

| ALCOHOL DEHYDROGENASES | |
| --- | --- |
| ec: 1.1.1.1 | alcohol dehydrogenase |
| ec: 1.1.1.2 | alcohol dehydrogenase (NADP+) |
| ec: 1.1.1.4 | (R,R)-butanediol dehydrogenase |
| ec: 1.1.1.5 | acetoin dehydrogenase |
| ec: 1.1.1.6 | glycerol dehydrogenase |
| ec: 1.1.1.7 | propanediol-phosphate dehydrogenase |
| ec: 1.1.1.8 | glycerol-3-phosphate dehydrogenase (NAD+) |
| ec: 1.1.1.11 | D-arabinitol 4-dehydrogenase |
| ec: 1.1.1.12 | L-arabinitol 4-dehydrogenase |
| ec: 1.1.1.13 | L-arabinitol 2-dehydrogenase |
| ec: 1.1.1.14 | L-iditol 2-dehydrogenase |
| ec: 1.1.1.15 | D-iditol 2-dehydrogenase |
| ec: 1.1.1.16 | galactitol 2-dehydrogenase |
| ec: 1.1.1.17 | mannitol-1-phosphate 5-dehydrogenase |

TABLE 1-continued

Alcohol and Aldehyde Dehydrogenases for Conversion of 4-HB to BDO.

| EC | Name |
|---|---|
| ec: 1.1.1.18 | inositol 2-dehydrogenase |
| ec: 1.1.1.21 | aldehyde reductase |
| ec: 1.1.1.23 | histidinol dehydrogenase |
| ec: 1.1.1.26 | glyoxylate reductase |
| ec: 1.1.1.27 | L-lactate dehydrogenase |
| ec: 1.1.1.28 | D-lactate dehydrogenase |
| ec: 1.1.1.29 | glycerate dehydrogenase |
| ec: 1.1.1.30 | 3-hydroxybutyrate dehydrogenase |
| ec: 1.1.1.31 | 3-hydroxyisobutyrate dehydrogenase |
| ec: 1.1.1.35 | 3-hydroxyacyl-CoA dehydrogenase |
| ec: 1.1.1.36 | acetoacetyl-CoA reductase |
| ec: 1.1.1.37 | malate dehydrogenase |
| ec: 1.1.1.38 | malate dehydrogenase (oxaloacetate-decarboxylating) |
| ec: 1.1.1.39 | malate dehydrogenase (decarboxylating) |
| ec: 1.1.1.40 | malate dehydrogenase (oxaloacetate-decarboxylating) (NADP+) |
| ec: 1.1.1.41 | isocitrate dehydrogenase (NAD+) |
| ec: 1.1.1.42 | isocitrate dehydrogenase (NADP+) |
| ec: 1.1.1.54 | allyl-alcohol dehydrogenase |
| ec: 1.1.1.55 | lactaldehyde reductase (NADPH) |
| ec: 1.1.1.56 | ribitol 2-dehydrogenase |
| ec: 1.1.1.59 | 3-hydroxypropionate dehydrogenase |
| ec: 1.1.1.60 | 2-hydroxy-3-oxopropionate reductase |
| ec: 1.1.1.61 | 4-hydroxybutyrate dehydrogenase |
| ec: 1.1.1.66 | omega-hydroxydecanoate dehydrogenase |
| ec: 1.1.1.67 | mannitol 2-dehydrogenase |
| ec: 1.1.1.71 | alcohol dehydrogenase [NAD(P)+] |
| ec: 1.1.1.72 | glycerol dehydrogenase (NADP+) |
| ec: 1.1.1.73 | octanol dehydrogenase |
| ec: 1.1.1.75 | (R)-aminopropanol dehydrogenase |
| ec: 1.1.1.76 | (S,S)-butanediol dehydrogenase |
| ec: 1.1.1.77 | lactaldehyde reductase |
| ec: 1.1.1.78 | methylglyoxal reductase (NADH-dependent) |
| ec: 1.1.1.79 | glyoxylate reductase (NADP+) |
| ec: 1.1.1.80 | isopropanol dehydrogenase (NADP+) |
| ec: 1.1.1.81 | hydroxypyruvate reductase |
| ec: 1.1.1.82 | malate dehydrogenase (NADP+) |
| ec: 1.1.1.83 | D-malate dehydrogenase (decarboxylating) |
| ec: 1.1.1.84 | dimethylmalate dehydrogenase |
| ec: 1.1.1.85 | 3-isopropylmalate dehydrogenase |
| ec: 1.1.1.86 | ketol-acid reductoisomerase |
| ec: 1.1.1.87 | homoisocitrate dehydrogenase |
| ec: 1.1.1.88 | hydroxymethylglutaryl-CoA reductase |
| ec: 1.1.1.90 | aryl-alcohol dehydrogenase |
| ec: 1.1.1.91 | aryl-alcohol dehydrogenase (NADP+) |
| ec: 1.1.1.92 | oxaloglycolate reductase (decarboxylating) |
| ec: 1.1.1.94 | glycerol-3-phosphate dehydrogenase [NAD(P)+] |
| ec: 1.1.1.95 | phosphoglycerate dehydrogenase |
| ec: 1.1.1.97 | 3-hydroxybenzyl-alcohol dehydrogenase |
| ec: 1.1.1.101 | acylglycerone-phosphate reductase |
| ec: 1.1.1.103 | L-threonine 3-dehydrogenase |
| ec: 1.1.1.104 | 4-oxoproline reductase |
| ec: 1.1.1.105 | retinol dehydrogenase |
| ec: 1.1.1.110 | indolelactate dehydrogenase |
| ec: 1.1.1.112 | indanol dehydrogenase |
| ec: 1.1.1.113 | L-xylose 1-dehydrogenase |
| ec: 1.1.1.129 | L-threonate 3-dehydrogenase |
| ec: 1.1.1.137 | ribitol-5-phosphate 2-dehydrogenase |
| ec: 1.1.1.138 | mannitol 2-dehydrogenase (NADP+) |
| ec: 1.1.1.140 | sorbitol-6-phosphate 2-dehydrogenase |
| ec: 1.1.1.142 | D-pinitol dehydrogenase |
| ec: 1.1.1.143 | sequoyitol dehydrogenase |
| ec: 1.1.1.144 | perillyl-alcohol dehydrogenase |
| ec: 1.1.1.156 | glycerol 2-dehydrogenase (NADP+) |
| ec: 1.1.1.157 | 3-hydroxybutyryl-CoA dehydrogenase |
| ec: 1.1.1.163 | cyclopentanol dehydrogenase |
| ec: 1.1.1.164 | hexadecanol dehydrogenase |
| ec: 1.1.1.165 | 2-alkyn-1-ol dehydrogenase |
| ec: 1.1.1.166 | hydroxycyclohexanecarboxylate dehydrogenase |
| ec: 1.1.1.167 | hydroxymalonate dehydrogenase |
| ec: 1.1.1.174 | cyclohexane-1,2-diol dehydrogenase |
| ec: 1.1.1.177 | glycerol-3-phosphate 1-dehydrogenase (NADP+) |
| ec: 1.1.1.178 | 3-hydroxy-2-methylbutyryl-CoA dehydrogenase |
| ec: 1.1.1.185 | L-glycol dehydrogenase |
| ec: 1.1.1.190 | indole-3-acetaldehyde reductase (NADH) |
| ec: 1.1.1.191 | indole-3-acetaldehyde reductase (NADPH) |
| ec: 1.1.1.192 | long-chain-alcohol dehydrogenase |
| ec: 1.1.1.194 | coniferyl-alcohol dehydrogenase |
| ec: 1.1.1.195 | cinnamyl-alcohol dehydrogenase |
| ec: 1.1.1.198 | (+)-borneol dehydrogenase |
| ec: 1.1.1.202 | 1,3-propanediol dehydrogenase |
| ec: 1.1.1.207 | (−)-menthol dehydrogenase |
| ec: 1.1.1.208 | (+)-neomenthol dehydrogenase |
| ec: 1.1.1.216 | farnesol dehydrogenase |
| ec: 1.1.1.217 | benzyl-2-methyl-hydroxybutyrate dehydrogenase |
| ec: 1.1.1.222 | (R)-4-hydroxyphenyllactate dehydrogenase |
| ec: 1.1.1.223 | isopiperitenol dehydrogenase |
| ec: 1.1.1.226 | 4-hydroxycyclohexanecarboxylate dehydrogenase |
| ec: 1.1.1.229 | diethyl 2-methyl-3-oxosuccinate reductase |
| ec: 1.1.1.237 | hydroxyphenylpyruvate reductase |
| ec: 1.1.1.244 | methanol dehydrogenase |
| ec: 1.1.1.245 | cyclohexanol dehydrogenase |
| ec: 1.1.1.250 | D-arabinitol 2-dehydrogenase |
| ec: 1.1.1.251 | galactitol 1-phosphate 5-dehydrogenase |
| ec: 1.1.1.255 | mannitol dehydrogenase |
| ec: 1.1.1.256 | fluoren-9-ol dehydrogenase |
| ec: 1.1.1.257 | 4-(hydroxymethyl)benzenesulfonate dehydrogenase |
| ec: 1.1.1.258 | 6-hydroxyhexanoate dehydrogenase |
| ec: 1.1.1.259 | 3-hydroxypimeloyl-CoA dehydrogenase |
| ec: 1.1.1.261 | glycerol-1-phosphate dehydrogenase [NAD(P)+] |
| ec: 1.1.1.265 | 3-methylbutanal reductase |
| ec: 1.1.1.283 | methylglyoxal reductase (NADPH-dependent) |
| ec: 1.1.1.286 | isocitrate-homoisocitrate dehydrogenase |
| ec: 1.1.1.287 | D-arabinitol dehydrogenase (NADP+) |
| | butanol dehydrogenase |

ALDEHYDE DEHYDROGENASES

| EC | Name |
|---|---|
| ec: 1.2.1.2 | formate dehydrogenase |
| ec: 1.2.1.3 | aldehyde dehydrogenase (NAD+) |
| ec: 1.2.1.4 | aldehyde dehydrogenase (NADP+) |
| ec: 1.2.1.5 | aldehyde dehydrogenase [NAD(P)+] |
| ec: 1.2.1.7 | benzaldehyde dehydrogenase (NADP+) |
| ec: 1.2.1.8 | betaine-aldehyde dehydrogenase |
| ec: 1.2.1.9 | glyceraldehyde-3-phosphate dehydrogenase (NADP+) |

TABLE 1-continued

Alcohol and Aldehyde Dehydrogenases for Conversion of 4-HB to BDO.

| | |
|---|---|
| ec: 1.2.1.10 | acetaldehyde dehydrogenase (acetylating) |
| ec: 1.2.1.11 | aspartate-semialdehyde dehydrogenase |
| ec: 1.2.1.12 | glyceraldehyde-3-phosphate dehydrogenase (phosphorylating) |
| ec: 1.2.1.13 | glyceraldehyde-3-phosphate dehydrogenase (NADP+) (phosphorylating) |
| ec: 1.2.1.15 | malonate-semialdehyde dehydrogenase |
| ec: 1.2.1.16 | succinate-semialdehyde dehydrogenase [NAD(P)+] |
| ec: 1.2.1.17 | glyoxylate dehydrogenase (acylating) |
| ec: 1.2.1.18 | malonate-semialdehyde dehydrogenase (acetylating) |
| ec: 1.2.1.19 | aminobutyraldehyde dehydrogenase |
| ec: 1.2.1.20 | glutarate-semialdehyde dehydrogenase |
| ec: 1.2.1.21 | glycolaldehyde dehydrogenase |
| ec: 1.2.1.22 | lactaldehyde dehydrogenase |
| ec: 1.2.1.23 | 2-oxoaldehyde dehydrogenase (NAD+) |
| ec: 1.2.1.24 | succinate-semialdehyde dehydrogenase |
| ec: 1.2.1.25 | 2-oxoisovalerate dehydrogenase (acylating) |
| ec: 1.2.1.26 | 2,5-dioxovalerate dehydrogenase |
| ec: 1.2.1.27 | methylmalonate-semialdehyde dehydrogenase (acylating) |
| ec: 1.2.1.28 | benzaldehyde dehydrogenase (NAD+) |
| ec: 1.2.1.29 | aryl-aldehyde dehydrogenase |
| ec: 1.2.1.30 | aryl-aldehyde dehydrogenase (NADP+) |
| ec: 1.2.1.31 | L-aminoadipate-semialdehyde dehydrogenase |
| ec: 1.2.1.32 | aminomuconate-semialdehyde dehydrogenase |
| ec: 1.2.1.36 | retinal dehydrogenase |
| ec: 1.2.1.39 | phenylacetaldehyde dehydrogenase |
| ec: 1.2.1.41 | glutamate-5-semialdehyde dehydrogenase |
| ec: 1.2.1.42 | hexadecanal dehydrogenase (acylating) |
| ec: 1.2.1.43 | formate dehydrogenase (NADP+) |
| ec: 1.2.1.45 | 4-carboxy-2-hydroxymuconate-6-semialdehyde dehydrogenase |
| ec: 1.2.1.46 | formaldehyde dehydrogenase |
| ec: 1.2.1.47 | 4-trimethylammoniobutyraldehyde dehydrogenase |
| ec: 1.2.1.48 | long-chain-aldehyde dehydrogenase |
| ec: 1.2.1.49 | 2-oxoaldehyde dehydrogenase (NADP+) |
| ec: 1.2.1.51 | pyruvate dehydrogenase (NADP+) |
| ec: 1.2.1.52 | oxoglutarate dehydrogenase (NADP+) |
| ec: 1.2.1.53 | 4-hydroxyphenylacetaldehyde dehydrogenase |
| ec: 1.2.1.57 | butanal dehydrogenase |
| ec: 1.2.1.58 | phenylglyoxylate dehydrogenase (acylating) |
| ec: 1.2.1.59 | glyceraldehyde-3-phosphate dehydrogenase (NAD(P)+) (phosphorylating) |
| ec: 1.2.1.62 | 4-formylbenzenesulfonate dehydrogenase |
| ec: 1.2.1.63 | 6-oxohexanoate dehydrogenase |
| ec: 1.2.1.64 | 4-hydroxybenzaldehyde dehydrogenase |
| ec: 1.2.1.65 | salicylaldehyde dehydrogenase |
| ec: 1.2.1.66 | mycothiol-dependent formaldehyde dehydrogenase |
| ec: 1.2.1.67 | vanillin dehydrogenase |
| ec: 1.2.1.68 | coniferyl-aldehyde dehydrogenase |
| ec: 1.2.1.69 | fluoroacetaldehyde dehydrogenase |
| ec: 1.2.1.71 | succinylglutamate-semialdehyde dehydrogenase |

Pathways other than those exemplified above also can be employed to generate the biosynthesis of BDO in non-naturally occurring microbial organisms. In one embodiment, biosynthesis can be achieved using a L-homoserine to BDO pathway. This pathway has a molar yield of 0.90 mol/mol glucose, which appears restricted by the availability of reducing equivalents. A second pathway synthesizes BDO from acetoacetate and is capable of achieving the maximum theoretical yield of 1.091 mol/mol glucose. Implementation of either pathway can be achieved by introduction of two exogenous enzymes, and both pathways can additionally complement BDO production via succinyl-CoA. Pathway enzymes, thermodynamics, theoretical yields and overall feasibility are described further below.

Figure 3:
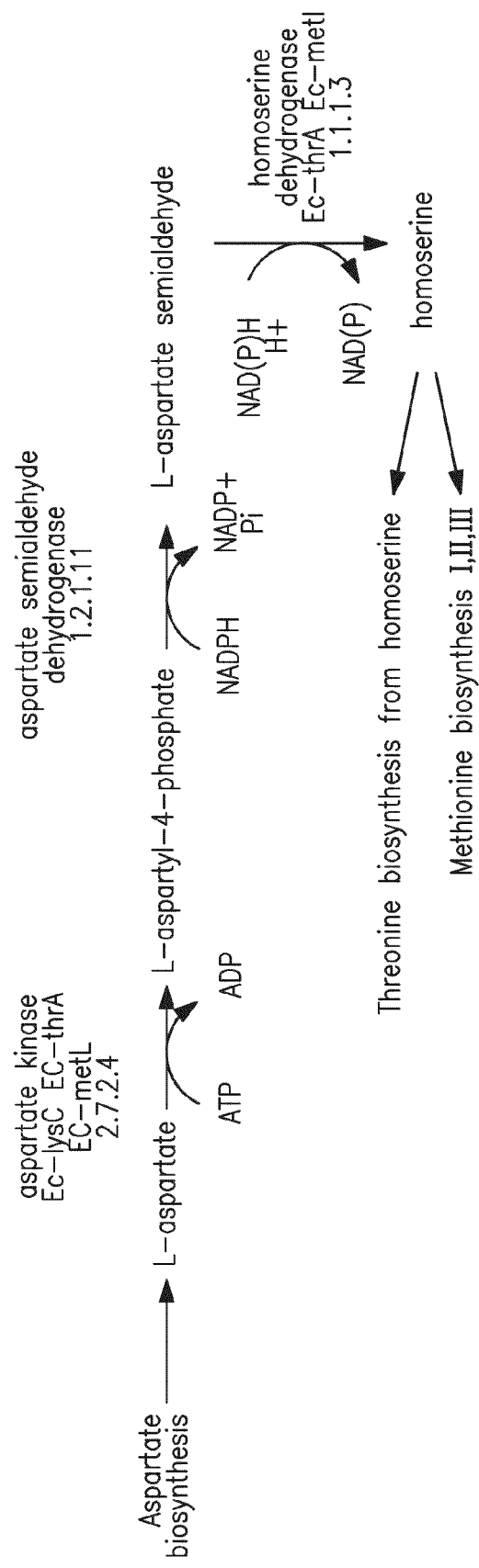
FIG. 3 is a schematic diagram showing homoserine biosynthesis in *E. coli*.

A homoserine pathway also can be engineered to generate BDO-producing microbial organisms. Homoserine is an intermediate in threonine and methionine metabolism, formed from oxaloacetate via aspartate. The conversion of oxaloacetate to homoserine requires one NADH, two NADPH, and one ATP (FIG. 3). Once formed, homoserine feeds into biosynthetic pathways for both threonine and methionine. In most organisms, high levels of threonine or methionine feedback to repress the homoserine biosynthesis pathway (Caspi et al., *Nucleic Acids Res.* 34:D511-D516 (1990)).

Figure 4:
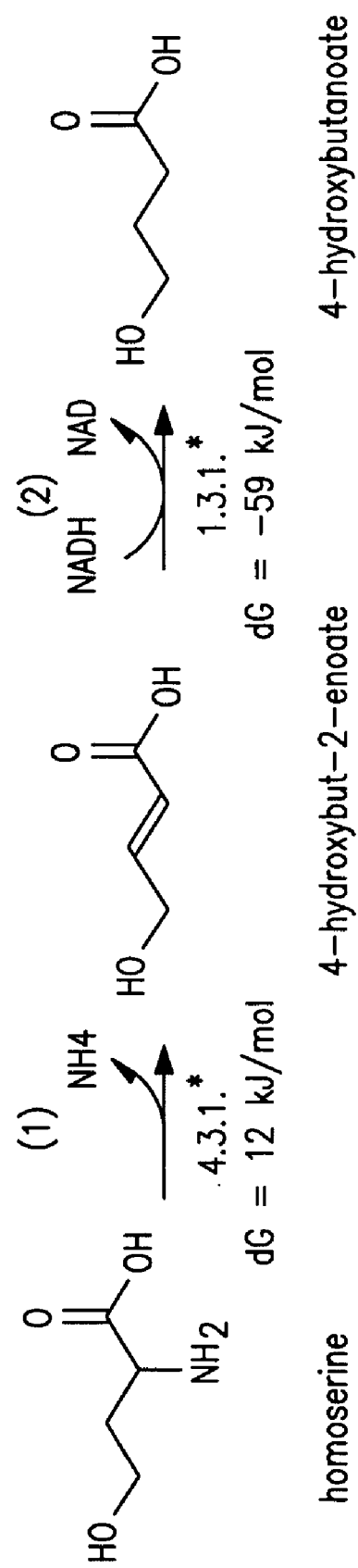
FIG. 4 shows a schematic diagram of a predicted homoserine biopathway from L-homoserine to 4-HB. Step 1 is a deduced ammonia-lyase (EC class 4.3.1) with an estimated ΔrxnG of 12 kJ/mol. Step 2 is a deduced oxidoreductase (EC class 1.3.1) with an estimated ΔrxnG of −59 kJ/mol.

The transformation of homoserine to 4-hydroxybutyrate (4-HB) can be accomplished in two enzymatic steps as shown in FIG. 4. The first step of this pathway is deamination of homoserine by a putative ammonia lyase. This reaction has an estimated thermodynamic barrier of 12 kJ/mol, but can likely be driven in the forward direction by a concentration gradient. In step 2, the product alkene, 4-hydroxybut-2-enoate is reduced to 4-HB by a putative reductase at the cost of one NADH. This reaction step is highly thermodynamically favorable in the direction of 4-HB synthesis, with an estimated $\Delta_{rxn}G$ of −59 kJ/mol. 4-HB can then be converted to BDO as in FIG. 2 above.

Figure 5:
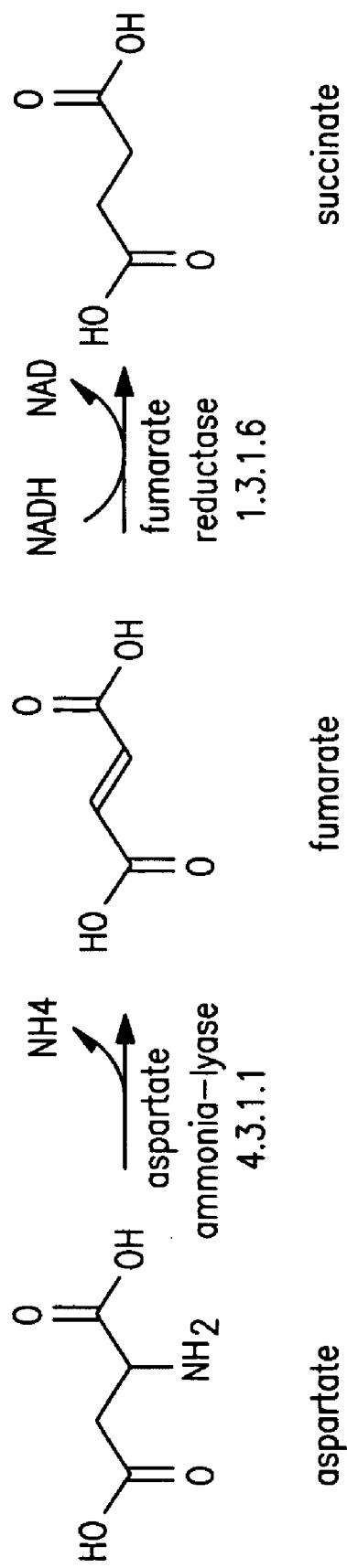
FIG. 5 shows a schematic diagram for the endogenous *E. coli* pathway for aspartate conversion to succinate via fumarate. This pathway exhibits similar chemistry to the predicted homoserine biopathway.
Figure 6:
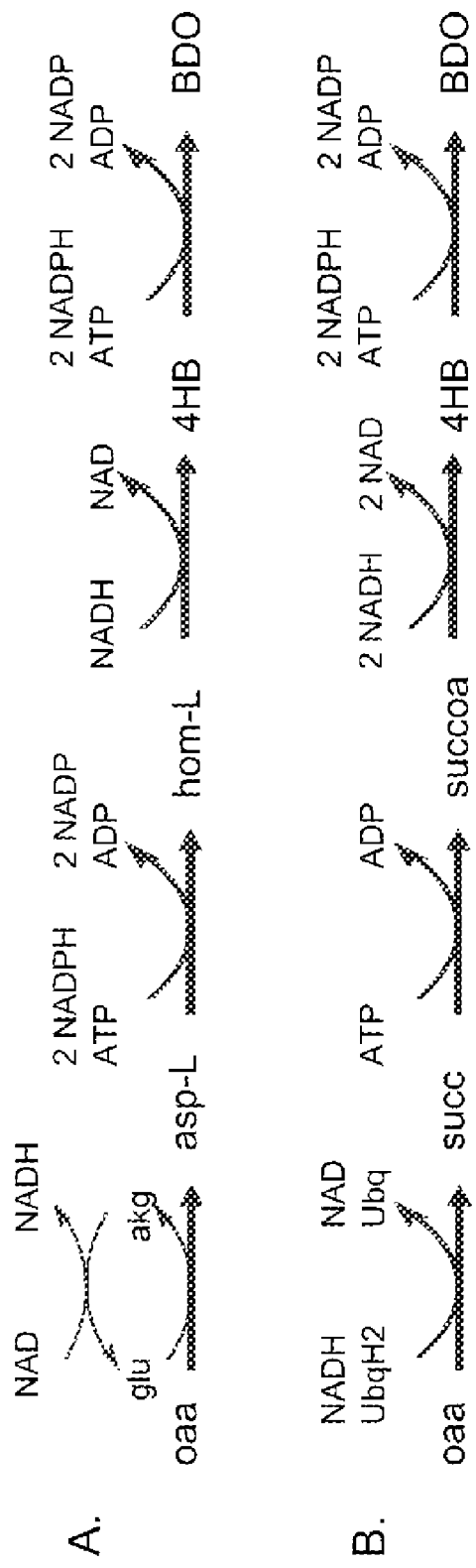
FIG. 6 shows a schematic diagram illustrating the parallels between (A) homoserine and (B) succinyl-CoA biosynthetic pathways to BDO.

Enzymes available for catalyzing the above transformations are shown in FIG. 5. For example, the ammonia lyase in step 1 of the pathway closely resembles the chemistry of aspartate ammonia-lyase (aspartase). Aspartase is a widespread enzyme in microorganisms, and has been characterized extensively (Viola, R. E., *Mol. Biol.* 74:295-341 (2008)). The crystal structure of the *E. coli* aspartase has been solved (Shi et al., *Biochemistry* 36:9136-9144 (1997)), so it is therefore possible to directly engineer mutations in the enzyme's active site that would alter its substrate specificity to include homoserine. The oxidoreductase in step 2 has chemistry similar to several well-characterized enzymes including fumarate reductase in the *E. coli* TCA cycle. Since the thermodynamics of this reaction are highly favorable, an endogenous reductase with broad substrate specificity will likely be able to reduce 4-hydroxybut-2-enoate. The yield of this pathway under anaerobic conditions is 0.9 mol BDO per mol glucose although, when compared to the pathway in FIG. 2 (1.09 mol/mol glucose), both pathways appear to have similar energetic and reductive requirements from the metabolic precursor oxaloacetate (FIG. 6).

The succinyl-CoA pathway was found to have a higher yield due to the fact that it is more energetically efficient. The conversion of one oxaloacetate molecule to BDO via the homoserine pathway will require the expenditure of 2 ATP equivalents. Because the conversion of glucose to two oxaloacetate molecules can generate a maximum of 3 ATP molecules assuming PEP carboxykinase to be reversible, the overall conversion of glucose to BDO via homoserine has a negative energetic yield. As expected, if we assume that energy can be generated via respiration, the maximum yield of the homoserine pathway increases to 1.05 mol/mol glucose which is 96% of the succinyl-CoA pathway yield. The succinyl-CoA pathway can channel some of the carbon flux through pyruvate dehydrogenase and the oxidative branch of the TCA cycle to generate both reducing equivalents and succinyl-CoA without an energetic expenditure. Thus, it does not encounter the same energetic difficulties as the homoserine pathway because not all of the flux is channeled through oxaloacetate to succinyl-CoA to BDO. Overall, the homoserine pathway demonstrates a moderately high-yielding route to BDO. One particularly useful characteristic is that it involves minimal engineering, with only two non-native steps. The pathway is likely to be thermodynamically favorable in the direction of BDO synthesis.

Figure 7:
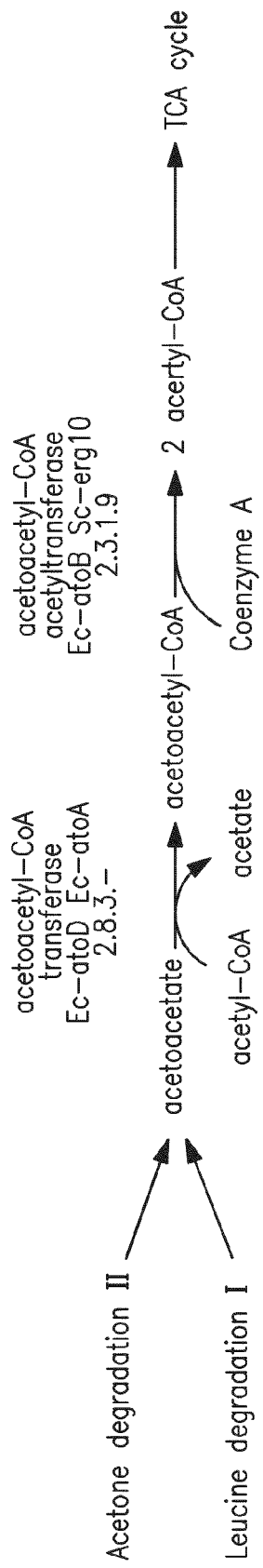
FIG. 7 is a schematic diagram showing biochemical pathways to acetoacetate in *E. coli*.

An acetoacetate pathway also can be engineered to generate BDO-producing microbial organisms. In *E. coli* acetoacetate is produced from acetone and leucine degradation. Acetoacetate also can be formed from acetyl-CoA by enzymes involved in fatty acid metabolism, including acetyl-CoA acetyltransferase and acetoacetyl-CoA transferase (FIG. 7). Biosynthetic routes through acetoacetate are also particularly useful in microbial organisms that can metabolize single carbon compounds to form acetyl-CoA.

Figure 8:
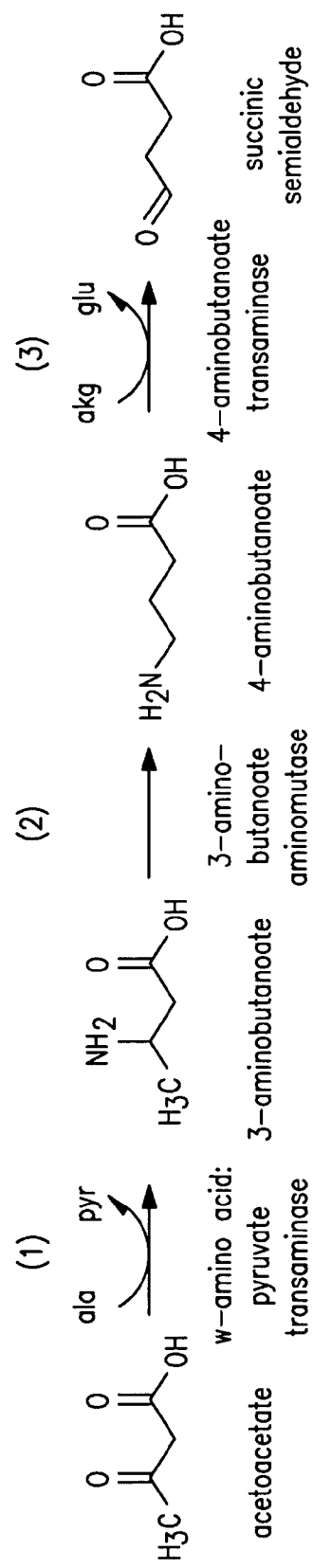
FIG. 8 is a schematic diagram showing a biochemical pathway from acetoacetate to BDO via succinic semialdehyde.

A three step route from acetoacetate to succinic semialdehyde (FIG. 8) can be used to synthesize BDO through acetoacetate. Succinic semialdehyde, which is one reduction step removed from succinyl-CoA or one decarboxylation step removed from α-ketoglutarate, can be converted to BDO following three reductions steps (FIG. 2). Briefly, step 1 of the acetoacetate biopathway entails conversion of acetoacetate to 3-aminobutanoate by an ω-aminotransferase. The ω-amino acid:pyruvate aminotransferase (ω-APT) from *Alcaligens denitrificans* was overexpressed in *E. coli* and shown to have a high activity toward 3-aminobutanoate in vitro (Yun et al., *Appl. Environ. Microbiol.* 70:2529-2534 (2004)). The activity of ω-APT in the direction required here was not measured in this study, due to spontaneous decomposition of acetoacetate to acetone in the reaction mixture. However, the thermodynamics indicate that it is feasible.

Figure 9:
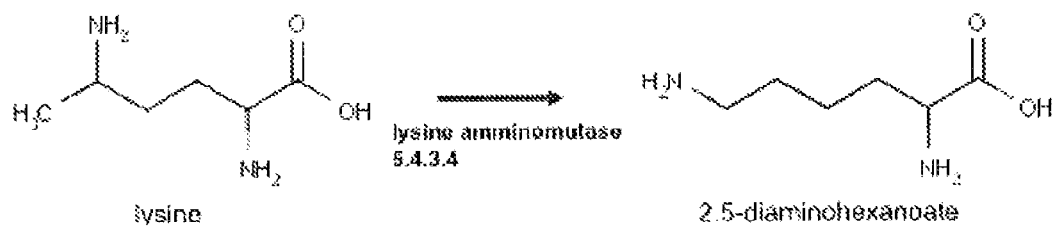
FIG. 9 is a schematic diagram showing a reaction scheme of D-lysine-5,6-amminomutase.

In step 2, a putative aminomutase shifts the amine group from the 3- to the 4-position of the carbon backbone. An aminomutase performing this function on 3-aminobutanoate has not been characterized, but an enzyme from *Clostridium sticklandii* has a very similar mechanism (FIG. 9). The enzyme, D-lysine-5,6-aminomutase, is involved in lysine biosynthesis.

The synthetic route to BDO from acetoacetate passes through 4-aminobutanoate, a metabolite in *E. coli* that's normally formed from decarboxylation of glutamate. Once formed, 4-aminobutanoate can be converted to succinic semialdehyde by 4-aminobutanoate transaminase (2.6.1.19), an enzyme which has been biochemically characterized. The thermodynamics of this enzyme and other steps of the pathway are close to equilibrium, so the operation of enzymes in the direction of interest is likely to be driven by substrate and product concentrations One consideration for selecting candidate enzymes in this pathway is the stereoselectivity of the enzymes involved in the first two steps. The ω-ABT in *Alcaligens denitrificans* is specific to the L-stereoisomer of 3-aminobutanoate, while D-lysine-5,6-aminomutase likely requires the D-stereoisomer. If enzymes with complementary stereoselectivity can't be found or engineered, it would be necessary to add a third enzyme to the pathway with racemase activity that can convert L-3-aminobutanoate to D-3-aminobutanoate. While amino acid racemases are widespread, whether these enzymes can function on ω-amino acids is not known.

Figure 10:
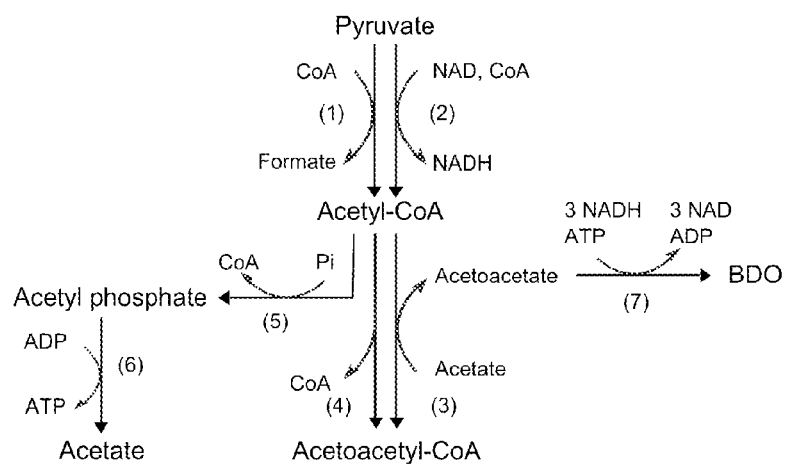
FIG. 10 is a schematic diagram showing a pathway to acetoacetate from acetyl-CoA. Enzymes are: (1) pyruvate formate-lyase, (2) pyruvate dehydrogenase, (3) acetyl-CoA: acetoacetyl-CoA transferase, (4) acetyl-CoA C-acetyltransferase, (5) phosphotransacetylase, and (6) Acetate kinase. Enzyme 7 represents the multistep acetoacetate to BDO pathway in FIG. 8.

The maximum theoretical molar yield of this pathway under anaerobic conditions is 1.091 mol/mol glucose. In order to generate flux from acetoacetate to BDO it was necessary to assume that acetyl-CoA:acetoacetyl-CoA transferase (enzyme 3 in FIG. 10) is reversible. The function of this enzyme in *E. coli* is to metabolize short-chain fatty acids by first converting them into thioesters.

While the operation of acetyl-CoA:acetoacetyl-CoA transferase in the acetate-consuming direction has not been demonstrated experimentally in *E. coli*, studies on similar enzymes in other organisms support the assumption that this reaction is reversible. The enzyme butyryl-CoA:acetate:CoA transferase in gut microbes *Roseburia* sp. and *F. prasnitzii* operates in the acetate utilizing direction to produce butyrate (Duncan et al., *Appl. Environ. Microbiol.* 68:5186-5190 (2002)). Another very similar enzyme, acetyl:succinate CoA-transferase in *Trypanosoma brucei*, also operates in the acetate utilizing direction. This reaction has a $\Delta_{rxn}G$ close to equilibrium, so high concentrations of acetate can likely drive the reaction in the direction of interest. At the maximum theoretical BDO production rate of 1.09 mol/mol glucose simulations predict that *E. coli* can generate 1.098 mol ATP per mol glucose with no fermentation byproducts. This ATP yield should be sufficient for cell growth, maintenance, and production. The acetoacetate biopathway is a high-yielding route to BDO from acetyl-CoA. Like the homoserine pathway, this pathway requires minimal strain engineering, with only two non-native steps in addition to the BDO pathway.

Therefore, in addition to any of the various modifications exemplified previously for establishing 4-HB biosynthesis in a selected host, the BDO producing microbial organisms can include any of the previous combinations and permutations of 4-HB pathway metabolic modifications as well as any combination of expression for CoA-independent aldehyde dehydrogenase, CoA-dependent aldehyde dehydrogenase or an alcohol dehydrogenase to generate biosynthetic pathways for GBL and/or BDO. Therefore, the BDO producers of the invention can have exogenous expression of, for example, one, two, three, four, five, six, seven, eight, nine or all 10 enzymes corresponding to any of the six 4-HB pathway and/or any of the 4 BDO pathway enzymes.

Design and construction of the genetically modified microbial organisms is carried out using methods well known in the art to achieve sufficient amounts of expression to produce BDO. In particular, the non-naturally occurring microbial organisms of the invention can achieve biosynthesis of BDO resulting in intracellular concentrations between about 0.1-25 mM or more. Generally, the intracellular concentration of BDO is between about 3-20 mM, particularly between about 5-15 mM and more particularly between about 8-12 mM, including about 10 mM or more. Intracellular concentrations between and above each of these exemplary ranges also can be achieved from the non-naturally occurring microbial organisms of the invention. As with the 4-HB producers, the BDO producers also can be sustained, cultured or fermented under anaerobic conditions.

The invention further provides a method for the production of 4-HB. The method includes culturing a non-naturally occurring microbial organism having a 4-hydroxybutanoic acid (4-HB) biosynthetic pathway comprising at least one exogenous nucleic acid encoding 4-hydroxybutanoate dehydrogenase, CoA-independent succinic semialdehyde dehydrogenase, succinyl-CoA synthetase, CoA-dependent succinic semialdehyde dehydrogenase, glutamate:succinic semialdehyde transaminase, α-ketoglutarate decarboxylase, or glutamate decarboxylase under substantially anaerobic conditions for a sufficient period of time to produce monomeric 4-hydroxybutanoic acid (4-HB). The method can additionally include chemical conversion of 4-HB to GBL and to BDO or THF, for example.

Additionally provided is a method for the production of 4-HB. The method includes culturing a non-naturally occurring microbial organism having a 4-hydroxybutanoic acid (4-HB) biosynthetic pathway including at least one exogenous nucleic acid encoding 4-hydroxybutanoate dehydrogenase, succinyl-CoA synthetase, CoA-dependent succinic semialdehyde dehydrogenase or α-ketoglutarate decarboxylase under substantially anaerobic conditions for a sufficient period of time to produce monomeric 4-hydroxybutanoic acid (4-HB). The 4-HB product can be secreted into the culture medium.

Further provided is a method for the production of BDO. The method includes culturing a non-naturally occurring microbial biocatalyst, comprising a microbial organism having 4-hydroxybutanoic acid (4-HB) and 1,4-butanediol (BDO) biosynthetic pathways, the pathways including at least one exogenous nucleic acid encoding 4-hydroxybutanoate dehydrogenase, succinyl-CoA synthetase, CoA-dependent succinic semialdehyde dehydrogenase, 4-hydroxybutyrate:CoA transferase, 4-hydroxybutyrate kinase, phosphotranshydroxybutyrylase, α-ketoglutarate decarboxylase, aldehyde dehydrogenase, alcohol dehydrogenase or an aldehyde/alcohol dehydrogenase for a sufficient period of time to produce 1,4-butanediol (BDO). The BDO product can be secreted into the culture medium.

It is understood that, in methods of the invention, any of the one or more exogenous nucleic acids can be introduced into a microbial organism to produce a non-naturally occurring microbial organism of the invention. The nucleic acids can be introduced so as to confer, for example, a 4-HB, BDO, THF or GBL biosynthetic pathway onto the microbial organism. Alternatively, encoding nucleic acids can be introduced to produce an intermediate microbial organism having the biosynthetic capability to catalyze some of the required reactions to confer 4-HB, BDO, THF or GBL biosynthetic capability. For example, a non-naturally occurring microbial organism having a 4-HB biosynthetic pathway can comprise at least two exogenous nucleic acids encoding desired enzymes, such as the combination of 4-hydroxybutanoate dehydrogenase and α-ketoglutarate decarboxylase; 4-hydroxybutanoate dehydrogenase and CoA-independent succinic semialdehyde dehydrogenase; 4-hydroxybutanoate dehydrogenase and CoA-dependent succinic semialdehyde dehydrogenase; CoA-dependent succinic semialdehyde dehydrogenase and succinyl-CoA synthetase; succinyl-CoA synthetase and glutamate decarboxylase, and the like. Thus, it is understood that any combination of two or more enzymes of a biosynthetic pathway can be included in a non-naturally occurring microbial organism of the invention. Similarly, it is understood that any combination of three or more enzymes of a biosynthetic pathway can be included in a non-naturally occurring microbial organism of the invention, for example, 4-hydroxybutanoate dehydrogenase, α-ketoglutarate decarboxylase and CoA-dependent succinic semialdehyde dehydrogenase; CoA-independent succinic semialdehyde dehydrogenase and succinyl-CoA synthetase; 4-hydroxybutanoate dehydrogenase, CoA-dependent succinic semialdehyde dehydrogenase and glutamate:succinic semialdehyde transaminase, and so forth, as desired, so long as the combination of enzymes of the desired biosynthetic pathway results in production of the corresponding desired product.

Similarly, for example, with respect to any one or more exogenous nucleic acids introduced to confer BDO production, a non-naturally occurring microbial organism having a BDO biosynthetic pathway can comprise at least two exogenous nucleic acids encoding desired enzymes, such as the combination of 4-hydroxybutanoate dehydrogenase and α-ketoglutarate decarboxylase; 4-hydroxybutanoate dehydrogenase and 4-hydroxybutyryl CoA:acetyl-CoA transferase; 4-hydroxybutanoate dehydrogenase and butyrate kinase; 4-hydroxybutanoate dehydrogenase and phosphotransbutyrylase; 4-hydroxybutyryl CoA:acetyl-CoA transferase and aldehyde dehydrogenase; 4-hydroxybutyryl CoA:acetyl-CoA transferase and alcohol dehydrogenase; 4-hydroxybutyryl CoA:acetyl-CoA transferase and an aldehyde/alcohol dehydrogenase, and the like. Thus, it is understood that any combination of two or more enzymes of a biosynthetic pathway can be included in a non-naturally occurring microbial organism of the invention. Similarly, it is understood that any combination of three or more enzymes of a biosynthetic pathway can be included in a non-naturally occurring microbial organism of the invention, for example, 4-hydroxybutanoate dehydrogenase, α-ketoglutarate decarboxylase and 4-hydroxybutyryl CoA:acetyl-CoA transferase; 4-hydroxybutanoate dehydrogenase, butyrate kinase and phosphotransbutyrylase; 4-hydroxybutanoate dehydrogenase, 4-hydroxybutyryl CoA:acetyl-CoA transferase and aldehyde dehydrogenase; 4-hydroxybutyryl CoA:acetyl-CoA transferase, aldehyde dehydrogenase and alcohol dehydrogenase; butyrate kinase, phosphotransbutyrylase and an aldehyde/alcohol dehydrogenase, and the like. Similarly, any combination of four, five or more enzymes of a biosynthetic pathway as disclosed herein can be included in a non-naturally occurring microbial organism of the invention, as desired, so long as the combination of enzymes of the desired biosynthetic pathway results in production of the corresponding desired product.

Any of the non-naturally occurring microbial organisms described previously can be cultured to produce and/or secrete the biosynthetic products of the invention. For example, the 4-HB producers can be cultured for the biosynthetic production of 4-HB. The 4-HB can be isolated or be treated as described below to generate GBL, THF and/or BDO. Similarly, the BDO producers can be cultured for the biosynthetic production of BDO. The BDO can be isolated or subjected to further treatments for the chemical synthesis of BDO family compounds such as those downstream compounds exemplified in FIG. 1.

The growth medium can be, for example, any carbohydrate source which can supply a source of carbon to the non-naturally occurring microorganism. Such sources include, for example, sugars such as glucose, xylose, arabinose, galactose, mannose, fructose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of 4-HB and other compounds of the invention.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, 4-HB, BDO and any of the intermediates metabolites in the 4-HB pathway, the BDO pathway and/or the combined 4-HB and BDO pathways. All that is required is to engineer in one or more of the enzyme activities shown in FIG. 2 to achieve biosynthesis of the desired compound or intermediate including, for example, inclusion of some or all of the 4-HB and/or BDO biosynthetic pathways. Accordingly, the invention provides a non-naturally occurring microbial organism that secretes 4-HB when grown on a carbohydrate, secretes BDO when grown on a carbohydrate and/or secretes any of the intermediate metabolites shown in FIG. 2 when grown on a carbohydrate. The BDO producing microbial organisms of the invention can initiate synthesis from, for example, succinate, succinyl-CoA, α-ketogluterate, succinic semialdehyde, 4-HB, 4-hydroxybutyrylphosphate, 4-hydroxybutyryl-CoA (4-HB-CoA) and/or 4-hydroxybutyraldehyde.

In some embodiments, culture conditions include anaerobic or substantially anaerobic growth or maintenance conditions. Exemplary anaerobic conditions have been described previously and are well known in the art. Exemplary anaerobic conditions for fermentation processes are described below in the Examples. Any of these conditions can be employed with the non-naturally occurring microbial organisms as well as other anaerobic conditions well known in the art. Under such anaerobic conditions, the 4-HB and BDO producers can synthesize monomeric 4-HB and BDO, respectively, at intracellular concentrations of 5-10 mM or more as well as all other concentrations exemplified previously.

A number of downstream compounds also can be generated for the 4-HB and BDO producing non-naturally occurring microbial organisms of the invention. With respect to the 4-HB producing microbial organisms of the invention, monomeric 4-HB and GBL exist in equilibrium in the culture medium. The conversion of 4-HB to GBL can be efficiently accomplished by, for example, culturing the microbial organisms in acid pH medium. A pH less than or equal to 7.5, in particular at or below pH 5.5, spontaneously converts 4-HB to GBL as illustrated in FIG. 1.

The resultant GBL can be separated from 4-HB and other components in the culture using a variety of methods well known in the art. Such separation methods include, for example, the extraction procedures exemplified in the Examples as well as methods which include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art. Separated GBL can be further purified by, for example, distillation.

Another down stream compound that can be produced from the 4-HB producing non-naturally occurring microbial organisms of the invention includes, for example, BDO. This compound can be synthesized by, for example, chemical hydrogenation of GBL. Chemical hydrogenation reactions are well known in the art. One exemplary procedure includes the chemical reduction of 4-HB and/or GBL or a mixture of these two components deriving from the culture using a heterogeneous or homogeneous hydrogenation catalyst together with hydrogen, or a hydride-based reducing agent used stoichiometrically or catalytically, to produce 1,4-butanediol.

Other procedures well known in the art are equally applicable for the above chemical reaction and include, for example, WO No. 82/03854 (Bradley, et al.), which describes the hydrogenolysis of gamma-butyrolactone in the vapor phase over a copper oxide and zinc oxide catalyst. British Pat. No. 1,230,276, which describes the hydrogenation of gamma-butyrolactone using a copper oxide-chromium oxide catalyst. The hydrogenation is carried out in the liquid phase. Batch reactions also are exemplified having high total reactor pressures. Reactant and product partial pressures in the reactors are well above the respective dew points. British Pat. No. 1,314,126, which describes the hydrogenation of gamma-butyrolactone in the liquid phase over a nickel-cobalt-thorium oxide catalyst. Batch reactions are exemplified as having high total pressures and component partial pressures well above respective component dew points. British Pat. No. 1,344,557, which describes the hydrogenation of gamma-butyrolactone in the liquid phase over a copper oxide-chromium oxide catalyst. A vapor phase or vapor-containing mixed phase is indicated as suitable in some instances. A continuous flow tubular reactor is exemplified using high total reactor pressures. British Pat. No. 1,512,751, which describes the hydrogenation of gamma-butyrolactone to 1,4-butanediol in the liquid phase over a copper oxide-chromium oxide catalyst. Batch reactions are exemplified with high total reactor pressures and, where determinable, reactant and product partial pressures well above the respective dew points. U.S. Pat. No. 4,301,077, which describes the hydrogenation to 1,4-butanediol of gamma-butyrolactone over a Ru—Ni—Co—Zn catalyst. The reaction can be conducted in the liquid or gas phase or in a mixed liquid-gas phase. Exemplified are continuous flow liquid phase reactions at high total reactor pressures and relatively low reactor productivities. U.S. Pat. No. 4,048,196, which describes the production of 1,4-butanediol by the liquid phase hydrogenation of gamma-butyrolactone over a copper oxide-zinc oxide catalyst. Further exemplified is a continuous flow tubular reactor operating at high total reactor pressures and high reactant and product partial pressures. And U.S. Pat. No. 4,652,685, which describes the hydrogenation of lactones to glycols.

A further downstream compound that can be produced form the 4-HB producing microbial organisms of the invention includes, for example, THF. This compound can be synthesized by, for example, chemical hydrogenation of GBL. One exemplary procedure well known in the art applicable for the conversion of GBL to THF includes, for example, chemical reduction of 4-HB and/or GBL or a mixture of these two components deriving from the culture using a heterogeneous or homogeneous hydrogenation catalyst together with hydrogen, or a hydride-based reducing agent used stoichiometrically or catalytically, to produce tetrahydrofuran. Other procedures well know in the art are equally applicable for the above chemical reaction and include, for example, U.S. Pat. No. 6,686,310, which describes high surface area sol-gel route prepared hydrogenation catalysts. Processes for the reduction of maleic acid to tetrahydrofuran (THF) and 1,4-butanediol (BDO) and for the reduction of gamma butyrolactone to tetrahydrofuran and 1,4-butanediol also are described.

The culture conditions can include, for example, liquid culture procedures as well as fermentation and other large scale culture procedures. As described further below in the Examples, particularly useful yields of the biosynthetic products of the invention can be obtained under anaerobic or substantially anaerobic culture conditions.

The invention further provides a method of manufacturing 4-HB. The method includes fermenting a non-naturally occurring microbial organism having a 4-hydroxybutanoic acid (4-HB) biosynthetic pathway comprising at least one exogenous nucleic acid encoding 4-hydroxybutanoate dehydrogenase, CoA-independent succinic semialdehyde dehydrogenase, succinyl-CoA synthetase, CoA-dependent succinic semialdehyde dehydrogenase, glutamate:succinic semialdehyde transaminase, a-ketoglutarate decarboxylase, or glutamate decarboxylase under substantially anaerobic conditions for a sufficient period of time to produce monomeric 4-hydroxybutanoic acid (4-HB), the process comprising fed-batch fermentation and batch separation; fed-batch fermentation and continuous separation, or continuous fermentation and continuous separation.

The culture and chemical hydrogenations described above also can be scaled up and grown continuously for manufacturing of 4-HB, GBL, BDO and/or THF. Exemplary growth procedures include, for example, fed-batch fermentation and batch separation; fed-batch fermentation and continuous separation, or continuous fermentation and continuous separation. All of these processes are well known in the art. Employing the 4-HB producers allows for simultaneous 4-HB biosynthesis and chemical conversion to GBL, BDO and/or THF by employing the above hydrogenation procedures simultaneous with continuous cultures methods such as fermentation. Other hydrogenation procedures also are well known in the art and can be equally applied to the methods of the invention.

Fermentation procedures are particularly useful for the biosynthetic production of commercial quantities of 4-HB and/or BDO. Generally, and as with non-continuous culture procedures, the continuous and/or near-continuous production of 4-HB or BDO will include culturing a non-naturally occurring 4-HB or BDO producing organism of the invention in sufficient nutrients and medium to sustain and/or nearly sustain growth in an exponential phase. Continuous culture under such conditions can be include, for example, 1 day, 2, 3, 4, 5, 6 or 7 days or more. Additionally, continuous culture can include 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods.

Fermentation procedures are well known in the art. Briefly, fermentation for the biosynthetic production of 4-HB, BDO or other 4-HB derived products of the invention can be utilized in, for example, fed-batch fermentation and batch separation; fed-batch fermentation and continuous separation, or continuous fermentation and continuous separation. Examples of batch and continuous fermentation procedures well known in the art are exemplified further below in the Examples.

In addition, to the above fermentation procedures using the 4-HB or BDO producers of the invention for continuous production of substantial quantities of monomeric 4-HB and BDO, respectively, the 4-HB producers also can be, for example, simultaneously subjected to chemical synthesis procedures as described previously for the chemical conversion of monomeric 4-HB to, for example, GBL, BDO and/or THF. The BDO producers can similarly be, for example, simultaneously subjected to chemical synthesis procedures as described previously for the chemical conversion of BDO to, for example, THF, GBL, pyrrolidones and/or other BDO family compounds. In addition, the products of the 4-HB and BDO producers can be separated from the fermentation culture and sequentially subjected to chemical conversion, as disclosed herein.

Briefly, hydrogenation of GBL in the fermentation broth can be performed as described by Frost et al., *Biotechnology Progress* 18: 201-211 (2002). Another procedure for hydrogenation during fermentation include, for example, the methods described in, for example, U.S. Pat. No. 5,478,952. This method is further exemplified in the Examples below.

Therefore, the invention additionally provides a method of manufacturing γ-butyrolactone (GBL), tetrahydrofuran (THF) or 1,4-butanediol (BDO). The method includes fermenting a non-naturally occurring microbial organism having 4-hydroxybutanoic acid (4-HB) and/or 1,4-butanediol (BDO) biosynthetic pathways, the pathways comprise at least one exogenous nucleic acid encoding 4-hydroxybutanoate dehydrogenase, CoA-independent succinic semialdehyde dehydrogenase, succinyl-CoA synthetase, CoA-dependent succinic semialdehyde dehydrogenase, 4-hydroxybutyrate:CoA transferase, glutamate:succinic semialdehyde transaminase, α-ketoglutarate decarboxylase, glutamate decarboxylase, 4-hydroxybutanoate kinase, phosphotransbutyrylase, CoA-independent 1,4-butanediol semialdehyde dehydrogenase, CoA-dependent 1,4-butanediol semialdehyde dehydrogenase, CoA-independent 1,4-butanediol alcohol dehydrogenase or CoA-dependent 1,4-butanediol alcohol dehydrogenase, under substantially anaerobic conditions for a sufficient period of time to produce 1,4-butanediol (BDO), GBL or THF, the fermenting comprising fed-batch fermentation and batch separation; fed-batch fermentation and continuous separation, or continuous fermentation and continuous separation.

In addition to the biosynthesis of 4-HB, BDO and other products of the invention as described herein, the non-naturally occurring microbial organisms and methods of the invention also can be utilized in various combinations with each other and with other microbial organisms and methods well known in the art to achieve product biosynthesis by other routes. For example, one alternative to produce BDO other than use of the 4-HB producers and chemical steps or other than use of the BDO producer directly is through addition of another microbial organism capable of converting 4-HB or a 4-HB product exemplified herein to BDO.

One such procedure includes, for example, the fermentation of a 4-HB producing microbial organism of the invention to produce 4-HB, as described above and below. The 4-HB can then be used as a substrate for a second microbial organism that converts 4-HB to, for example, BDO, GBL and/or THF. The 4-HB can be added directly to another culture of the second organism or the original culture of 4-HB producers can be depleted of these microbial organisms by, for example, cell separation, and then subsequent addition of the second organism to the fermentation broth can utilized to produce the final product without intermediate purification steps. One exemplary second organism having the capacity to biochemically utilize 4-HB as a substrate for conversion to BDO, for example, is *Clostridium acetobutylicum* (see, for example, Jewell et al., *Current Microbiology*, 13:215-19 (1986)).

In other embodiments, the non-naturally occurring microbial organisms and methods of the invention can be assembled in a wide variety of subpathways to achieve biosynthesis of, for example, 4-HB and/or BDO as described. In these embodiments, biosynthetic pathways for a desired product of the invention can be segregated into different microbial organisms and the different microbial organisms can be co-cultured to produce the final product. In such a biosynthetic scheme, the product of one microbial organism is the substrate for a second microbial organism until the final product is synthesized. For example, the biosynthesis of BDO can be accomplished as described previously by constructing a microbial organism that contains biosynthetic pathways for conversion of a substrate such as endogenous succinate through 4-HB to the final product BDO. Alternatively, BDO also can be bio synthetically produced from microbial organisms through co-culture or co-fermentation using two organisms in the same vessel. A first microbial organism being a 4-HB producer with genes to produce 4-HB from succinic acid, and a second microbial organism being a BDO producer with genes to convert 4-HB to BDO.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce 4-HB, BDO, GBL and THF products of the invention.

One computational method for identifying and designing metabolic alterations favoring biosynthesis of a product is the OptKnock computational framework, Burgard et al., *Biotechnol Bioeng*, 84: 647-57 (2003). OptKnock is a metabolic modeling and simulation program that suggests gene deletion strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of 4-HB and/or BDO or used in connection with the non-naturally occurring microbial organisms for further optimization of 4-HB and/or BDO biosynthesis.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that enable an effective query of the performance limits of metabolic networks and provides methods for solving the resulting mixed-integer linear programming problems. The metabolic modeling and simulation methods referred to herein as OptKnock are described in, for example, U.S. patent application Ser. No. 10/043,440, filed Jan. 10, 2002, and in International Patent No. PCT/US02/00660, filed Jan. 10, 2002.

Another computational method for identifying and designing metabolic alterations favoring biosynthetic production of a product is metabolic modeling and simulation system termed SimPheny®. This computational method and system is described in, for example, U.S. patent application Ser. No. 10/173,547, filed Jun. 14, 2002, and in International Patent Application No. PCT/US03/18838, filed Jun. 13, 2003.

SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components. Analysis methods such as convex analysis, linear programming and the calculation of extreme pathways as described, for example, in Schilling et al., *J. Theor. Biol.* 203:229-248 (2000); Schilling et al., *Biotech. Bioeng.* 71:286-306 (2000) and Schilling et al., *Biotech. Prog.* 15:288-295 (1999), can be used to determine such phenotypic capabilities. As described in the Examples below, this computation methodology was used to identify and analyze the feasible as well as the optimal 4-HB biosynthetic pathways in 4-HB non-producing microbial organisms.

As described above, one constraints-based method used in the computational programs applicable to the invention is flux balance analysis. Flux balance analysis is based on flux balancing in a steady state condition and can be performed as described in, for example, Varma and Palsson, *Biotech. Bioeng.* 12:994-998 (1994). Flux balance approaches have been applied to reaction networks to simulate or predict systemic properties of, for example, adipocyte metabolism as described in Fell and Small, *J. Biochem.* 138:781-786 (1986), acetate secretion from *E. coli* under ATP maximization conditions as described in Majewski and Domach, *Biotech. Bioeng.* 35:732-738 (1990) or ethanol secretion by yeast as described in Vanrolleghem et al., *Biotech. Prog.* 12:434-448 (1996). Additionally, this approach can be used to predict or simulate the growth of *E. coli* on a variety of single-carbon sources as well as the metabolism of *H. influenzae* as described in Edwards and Palsson, *Proc. Natl. Acad. Sci.* 97:5528-5533 (2000), Edwards and Palsson, *J. Bio. Chem.* 274:17410-17416 (1999) and Edwards et al., *Nature Biotech.* 19:125-130 (2001).

Once the solution space has been defined, it can be analyzed to determine possible solutions under various conditions. This computational approach is consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of 4-HB, BDO, GBL, THF and other BDO family compounds in host microbial organisms other than *E. coli* and yeast. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The ability of a cell or organism to biosynthetically produce a biochemical product can be illustrated in the context of the biochemical production limits of a typical metabolic network calculated using an in silico model. These limits are obtained by fixing the uptake rate(s) of the limiting substrate(s) to their experimentally measured value(s) and calculating the maximum and minimum rates of biochemical production at each attainable level of growth. The production of a desired biochemical generally is in direct competition with biomass formation for intracellular resources. Under these circumstances, enhanced rates of biochemical production will necessarily result in sub-maximal growth rates. The knockouts suggested by the above metabolic modeling and simulation programs such as OptKnock are designed to restrict the allowable solution boundaries forcing a change in metabolic behavior from the wild-type strain. Although the actual solution boundaries for a given strain will expand or contract as the substrate uptake rate(s) increase or decrease, each experimental point will lie within its calculated solution boundary. Plots such as these enable accurate predictions of how close the designed strains are to their performance limits which also indicates how much room is available for improvement.

The OptKnock mathematical framework is exemplified herein for pinpointing gene deletions leading to product biosynthesis and, particularly, growth-coupled product biosynthesis. The procedure builds upon constraint-based metabolic modeling which narrows the range of possible phenotypes that a cellular system can display through the successive imposition of governing physico-chemical constraints, Price et al., *Nat Rev Microbiol*, 2: 886-97 (2004). As described above, constraint-based models and simulations are well known in the art and generally invoke the optimization of a particular cellular objective, subject to network stoichiometry, to suggest a likely flux distribution.

Briefly, the maximization of a cellular objective quantified as an aggregate reaction flux for a steady state metabolic network comprising a set $N=\{1, \ldots, N\}$ of metabolites and a set $M=\{1, \ldots, M\}$ of metabolic reactions is expressed mathematically as follows: maximize $$v_{cellular\ objective}$$

subject to $$\sum_{j=1}^{M} S_{ij} v_j = 0, \quad \forall\ i \in N$$

$$v_{substrate} = v_{substrate\_uptake}\ \text{mmol/gDW·hr}\ \forall i \in \{\text{limiting substrate(s)}\}$$

$$v_{atp} \geq v_{atp\_main}\ \text{mmol/gDW·hr}$$

$$v_j \geq 0, \forall j \in \{\text{irrev. reactions}\}$$

where $S_{ij}$ is the stoichiometric coefficient of metabolite i in reaction j, $v_j$ is the flux of reaction j, $v_{substrate\_uptake}$ represents the assumed or measured uptake rate(s) of the limiting substrate(s), and $v_{atp\_main}$ is the non-growth associated ATP maintenance requirement. The vector v includes both internal and external fluxes. In this study, the cellular objective is often assumed to be a drain of biosynthetic precursors in the ratios required for biomass formation, Neidhardt, F. C. et al., *Escherichia coli and Salmonella: Cellular and Molecular Biology*, 2nd ed. 1996, Washington, D.C.: ASM Press. 2 v. (xx, 2822, lxxvi). The fluxes are generally reported per 1 gDW·hr (gram of dry weight times hour) such that biomass formation is expressed as g biomass produced/gDW·hr or 1/hr.

The modeling of gene deletions, and thus reaction elimination, first employs the incorporation of binary variables into the constraint-based approach framework, Burgard et al., *Biotechnol Bioeng*, 74: 364-375 (2001), Burgard et al., *Biotechnol Prog*, 17: 791-797 (2001). These binary variables, $$y_j = \begin{cases} 1, & \text{if reaction flux } v_j \text{ is active} \\ 0, & \text{if reaction flux } v_j \text{ is not active} \end{cases}, \forall\ j \in M$$

assume a value of 1 if reaction j is active and a value of 0 if it is inactive. The following constraint, $$v_j^{min} \cdot y_j \leq v_j \leq v_j^{max} \cdot y_j, \forall j \in M$$

ensures that reaction flux $v_j$ is set to zero only if variable $y_j$ is equal to zero. Alternatively, when $y_j$ is equal to one, $v_j$ is free to assume any value between a lower $v_j^{min}$ and an upper $v_j^{max}$ bound. Here, $v_j^{min}$ and $v_j^{max}$ are identified by minimizing and maximizing, respectively, every reaction flux subject to the network constraints described above, Mahadevan et al., *Metab Eng*, 5: 264-76 (2003).

Optimal gene/reaction knockouts are identified by solving a bilevel optimization problem that chooses the set of active reactions ($y_j=1$) such that an optimal growth solution for the resulting network overproduces the chemical of interest. Mathematically, this bilevel optimization problem is expressed as the following bilevel mixed-integer optimization problem:

$$\underset{y_j}{\text{maximize}}\ v_{chemical}\ (OptKnock)$$

$$\begin{pmatrix} \text{subject to}\ \underset{v_j}{\text{maximize}} & v_{biomass} & \\ \text{subject to} & \sum_{j=1}^{M} S_{ij} v_j = 0, & \forall\ i \in N \\ & v_{substrate} = v_{substrate\_uptake} & \forall\ i \in \{\text{limiting substrate}(s)\} \\ & v_{atp} \geq v_{atp\_main} & \end{pmatrix}$$

$$v_{biomass} \geq v_{biomass}^{target}$$

$$v_j^{min} \cdot y_j \leq v_j \leq v_j^{max} \cdot y_j, \forall\ j \in M$$

$$\sum_{j \in M^{forward}} (1 - y_j) = K$$

$$y_j \in \{0, 1\}, \forall\ j \in M$$

where $v_{chemical}$ is the production of the desired target product, for example succinate or other biochemical product, and K is the number of allowable knockouts. Note that setting K equal to zero returns the maximum biomass solution of the complete network, while setting K equal to one identifies the single gene/reaction knockout ($y_j$=0) such that the resulting network involves the maximum overproduction given its maximum biomass yield. The final constraint ensures that the resulting network meets a minimum biomass yield. Burgard et al., *Biotechnol Bioeng*, 84: 647-57 (2003), provide a more detailed description of the model formulation and solution procedure. Problems containing hundreds of binary variables can be solved in the order of minutes to hours using CPLEX 8.0, *GAMS: The Solver Manuals*. 2003: GAMS Development Corporation, accessed via the GAMS, Brooke et al., *GAMS Development Corporation* (1998), modeling environment on an IBM RS6000-270 workstation. The OptKnock framework has already been able to identify promising gene deletion strategies for biochemical overproduction, Burgard et al., *Biotechnol Bioeng*, 84: 647-57 (2003), Pharkya et al., *Biotechnol Bioeng*, 84: 887-899 (2003), and establishes a systematic framework that will naturally encompass future improvements in metabolic and regulatory modeling frameworks.

Any solution of the above described bilevel OptKnock problem will provide one set of metabolic reactions to disrupt. Elimination of each reaction within the set or metabolic modification can result in 4-HB or BDO as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve 4-HB or BDO production are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the succinate coupling are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of 4-HB or other biochemical product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatory couples product biosynthesis to growth. For example, if a previously identified growth-coupled metabolic modification specifies reactions 1, 2, and 3 for disruption, then the following constraint prevents the same reactions from being simultaneously considered in subsequent solutions: $y_1+y_2+y_3 \geq 1$. The integer cut method is well known in the art and can be found described in, for example, reference, Burgard et al., *Biotechnol Prog*, 17: 791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

Constraints of the above form preclude identification of larger reaction sets that include previously identified sets. For example, employing the integer cut optimization method above in a further iteration would preclude identifying a quadruple reaction set that specified reactions 1, 2, and 3 for disruption since these reactions had been previously identified. To ensure identification of all possible reaction sets leading to biosynthetic production of a product, a modification of the integer cut method can be employed.

Briefly, the modified integer cut procedure begins with iteration 'zero' which calculates the maximum production of the desired biochemical at optimal growth for a wild-type network. This calculation corresponds to an OptKnock solution with K equaling 0. Next, single knockouts are considered and the two parameter sets, objstore$_{iter}$ and ystore$_{iter,j}$, are introduced to store the objective function ($v_{chemical}$) and reaction on-off information ($y_j$), respectively, at each iteration, iter. The following constraints are then successively added to the OptKnock formulation at each iteration.

$$v_{chemical} \geq \text{objstore}_{iter} + \epsilon - M \cdot \Sigma_{j \epsilon ystore_{iter,j}=0} y_j$$

In the above equation, $\epsilon$ and M are a small and a large numbers, respectively. In general, $\epsilon$ can be set at about 0.01 and M can be set at about 1000. However, numbers smaller and/or larger then these numbers also can be used. M ensures that the constraint can be binding only for previously identified knockout strategies, while $\epsilon$ ensures that adding knockouts to a previously identified strategy must lead to an increase of at least $\epsilon$ in biochemical production at optimal growth. The approach moves onto double deletions whenever a single deletion strategy fails to improve upon the wild-type strain. Triple deletions are then considered when no double deletion strategy improves upon the wild-type strain, and so on. The end result is a ranked list, represented as desired biochemical production at optimal growth, of distinct deletion strategies that differ from each other by at least one knockout. This optimization procedure as well as the identification of a wide variety of reaction sets that, when disrupted, lead to the biosynthesis, including growth-coupled production, of a biochemical product. Given the teachings and guidance provided herein, those skilled in the art will understand that the methods and metabolic engineering designs exemplified herein are equally applicable to identify new biosynthetic pathways and/or to the obligatory coupling of cell or microorganism growth to any biochemical product.

The methods exemplified above and further illustrated in the Examples below enable the construction of cells and organisms that biosynthetically produce, including obligatory couple production of a target biochemical product to growth of the cell or organism engineered to harbor the identified genetic alterations. In this regard, metabolic alterations have been identified that result in the biosynthesis of 4-HB and 1,4-butanediol. Microorganism strains constructed with the identified metabolic alterations produce elevated levels of 4-HB or BDO compared to unmodified microbial organisms.

These strains can be beneficially used for the commercial production of 4-HB, BDO, THF and GBL, for example, in continuous fermentation process without being subjected to the negative selective pressures.

Therefore, the computational methods described herein enable the identification and implementation of metabolic modifications that are identified by an in silico method selected from OptKnock or SimPheny. The set of metabolic modifications can include, for example, addition of one or more biosynthetic pathway enzymes and/or functional disruption of one or more metabolic reactions including, for example, disruption by gene deletion.

It is understood that modifications which do not substantially affect the activity of the various embodiments of this invention are also included within the definition of the invention provided herein. Accordingly, the following examples are intended to illustrate but not limit the present invention.

EXAMPLE I

Biosynthesis of 4-Hydroxybutanoic Acid

This Example describes the biochemical pathways for 4-HB production.

Previous reports of 4-HB synthesis in microbes have focused on this compound as an intermediate in production of the biodegradable plastic poly-hydroxyalkanoate (PHA) (U.S. Pat. No. 6,117,658). The use of 4-HB/3-HB copolymers over poly-3-hydroxybutyrate polymer (PHB) can result in plastic that is less brittle (Saito and Doi, *Intl. J. Biol. Macromol.* 16:99-104 (1994)). The production of monomeric 4-HB described herein is a fundamentally distinct process for several reasons: (1) the product is secreted, as opposed to PHA which is produced intracellularly and remains in the cell; (2) for organisms that produce hydroxybutanoate polymers, free 4-HB is not produced, but rather the Coenzyme A derivative is used by the polyhydroxyalkanoate synthase; (3) in the case of the polymer, formation of the granular product changes thermodynamics; and (4) extracellular pH is not an issue for production of the polymer, whereas it will affect whether 4-HB is present in the free acid or conjugate base state, and also the equilibrium between 4-HB and GBL.

4-HB can be produced in two enzymatic reduction steps from succinate, a central metabolite of the TCA cycle, with succinic semialdehyde as the intermediate (FIG. 2). The first of these enzymes, succinic semialdehyde dehydrogenase, is native to many organisms including *E. coli*, in which both NADH- and NADPH-dependent enzymes have been found (Donnelly and Cooper, *Eur. J. Biochem.* 113:555-561 (1981); Donnelly and Cooper, *J. Bacteriol.* 145:1425-1427 (1981); Marek and Henson, *J. Bacteriol.* 170:991-994 (1988)). There is also evidence supporting succinic semialdehyde dehydrogenase activity in *S. cerevisiae* (Ramos et al., *Eur. J. Biochem.* 149:401-404 (1985)), and a putative gene has been identified by sequence homology. However, most reports indicate that this enzyme proceeds in the direction of succinate synthesis, as shown in FIG. 2 (Donnelly and Cooper, supra; Lutke-Eversloh and Steinbuchel, *FEMS Microbiol. Lett.* 181:63-71 (1999)), participating in the degradation pathway of 4-HB and gamma-aminobutyrate. Succinic semialdehyde also is natively produced by certain microbial organisms such as *E. coli* through the TCA cycle intermediate α-ketogluterate via the action of two enzymes: glutamate:succinic semialdehyde transaminase and glutamate decarboxylase. An alternative pathway, used by the obligate anaerobe *Clostridium kluyveri* to degrade succinate, activates succinate to succinyl-CoA, then converts succinyl-CoA to succinic semialdehyde using an alternative succinic semialdehyde dehydrogenase which is known to function in this direction (Sohling and Gottschalk, *Eur. J. Biochem.* 212:121-127 (1993)). However, this route has the energetic cost of ATP required to convert succinate to succinyl-CoA.

The second enzyme of the pathway, 4-hydroxybutanoate dehydrogenase, is not native to *E. coli* or yeast but is found in various bacteria such as *C. kluyveri* and *Ralstonia eutropha* (Lutke-Eversloh and Steinbuchel, supra; Sohling and Gottschalk, *J. Bacteriol.* 178:871-880 (1996); Valentin et al., *Eur. J. Biochem.* 227:43-60 (1995); Wolff and Kenealy, *Protein Expr. Purif.* 6:206-212 (1995)). These enzymes are known to be NADH-dependent, though NADPH-dependent forms also exist. An additional pathway to 4-HB from alpha-ketoglutarate was demonstrated in *E. coli* resulting in the accumulation of poly(4-hydroxybutyric acid) (Song et al., *Wei Sheng Wu Xue. Bao.* 45:382-386 (2005)). The recombinant strain required the overexpression of three heterologous genes, PHA synthase (*R. eutropha*), 4-hydroxybutyrate dehydrogenase (*R. eutropha*) and 4-hydroxybutyrate:CoA transferase (*C. kluyveri*), along with two native *E. coli* genes: glutamate:succinic semialdehyde transaminase and glutamate decarboxylase. Steps 4 and 5 in FIG. 2 can alternatively be carried out by an alpha-ketoglutarate decarboxylase such as the one identified in *Euglena gracilis* (Shigeoka et al., *Biochem. J.* 282(Pt2):319-323 (1992); Shigeoka and Nakano, *Arch. Biochem. Biophys.* 288:22-28 (1991); Shigeoka and Nakano, *Biochem J.* 292(Pt 2):463-467 (1993)). However, this enzyme has not previously been applied to impact the production of 4-HB or related polymers in any organism.

The reported directionality of succinic semialdehyde dehydrogenase led to the investigation of the thermodynamics of 4-HB metabolism. Specifically, this study investigated whether or not the reactions involved in the conversion of succinate or succinyl-CoA to 4-HB are thermodynamically favorable (i.e., $\Delta G_r < 0$) under the typical physiological conditions present in *E. coli* and *S. cerevisiae*. All oxidation/reduction reactions were assumed to utilize NADH, although the results for assuming NADPH utilization would be similar. Standard Gibbs free energies of formation ($\Delta G_f^o$) were calculated for each compound in the succinate and succinyl-CoA pathways shown in FIG. 2 based on the group contribution method (Mavrovouniotis, M. L., *J. Biol. Chem.* 266: 14440-14445 (1991)). Each standard Gibbs energy of formation was then transformed in order to obtain a criterion of spontaneous change at specified pressure, temperature, pH, and ionic strength (Alberty, R. A., *Biochem. Biophys. Acta* 1207:1-11 (1994)) (equation 1).

$$\Delta G'_f(I, \text{pH}) = \Delta G_f^o(I = 0) + N_H RT \ln(10^{pH}) - 2.915\sqrt{I}\,\frac{z^2 - N_H}{1 + B\sqrt{I}} \quad (1)$$

Where $\Delta G_f^o$ is the standard Gibbs energy of formation, $N_H$ is the number of hydrogen atoms in the compound, R is the universal gas constant, T is constant at 298K, z is the charge of the molecule at the pH of interest, I is the ionic strength in M, and B is a constant equal to $1.6\ L^{0.5}/\text{mol}^{0.5}$.

Equation 1 reveals that both intracellular pH and ionic strength play a role in determining thermodynamic feasibility. Normally, intracellular pH of cells is very well regulated, even when there are large variations in the culture pH. The intracellular pH of *E. coli* and *S. cerevisiae* have both been reported in the literature. *E. coli* maintains an intracellular pH of 7.4-7.7 during typical growth conditions in neutral buffers, but can drop to 7.2 in pH 6 medium, and even go as low as 6.9 for external pH of 5 (Riondet et al., *Biotechnology Tech.* 11:735-738 (1997)). However, growth of *E. coli* is severely inhibited at external pH below 6. Yeast pH exhibits more variation. During exponential growth phase, *S. cerevisiae* internal pH has been measured to be in the range of 6.7-7.0 with external pH controlled at 5.0 (Dombek and Ingram, *Appl. Environ. Microbiol.* 53:1286-1291 (1987)). On the other hand, in resting cells the internal pH drops to below 6 when the external pH is 6 or less (Imai and Ohno, *J. Biotechnol.* 38:165-172 (1995)). This analysis assumes an intracellular pH of 7.4 for *E. coli* and 6.8 for *S. cerevisiae*. An ionic strength of 0.15 also was assumed (Valenti et al., supra).

Transformed Gibbs energies of formation were calculated at the standard state (pH=7.0, I=0) and at physiological states of *E. coli* (pH=7.4, 10.15) and *S. cerevisiae* (pH=6.8, I=0.15). Transformed Gibbs energies of reaction ($\Delta G_r'$) were then calculated by taking the difference in $\Delta G_f'$ between the products and reactants. The transformed Gibbs energies of the reactions necessary to convert succinate or succinyl-CoA to 4-HB are provided in Table 2. Although some of the steps have calculated positive delta G values, the standard errors for these calculations and concentration gradients indicate that any of the steps are feasible. Note that the standard error, $U_{f,est}$, on $\Delta G_f$ calculated by the group contribution theory is 4 kcal/mol. The uncertainty in $\Delta G_r$, $U_{r,est}$, can be calculated as the Euclidean norm of the uncertainty for $\Delta G_f$ of each compound (Equation).

$$U_{r,est} = \sqrt{\sum_{i=1}^{m} n_i^2 * U_{f,est}^2} = \sqrt{\sum_{i=1}^{m} 16 n_i^2} \quad (2)$$

Where n is the stoichiometric coefficient and i is the compound. For the examined reactions, this uncertainty is on the order of 8 kcal/mol.

TABLE 2

Gibbs free energy of reaction (kcal/mole) at different pH and ionic strength values.

| Reaction | $\Delta G_r^{o'}$ pH = 7.0 IS = 0 | $\Delta G_r'$ pH = 7.4 IS = 0.15 M | $\Delta G_r'$ pH = 6.8 IS = 0.15 M |
|---|---|---|---|
| succ + NADH + 2 H+ → sucsa + NAD + h2o | 12.0 | 14.4 | 12.8 |
| succ + coa + ATP → succoa + ADP + Pi | 0.30 | −0.03 | −0.03 |
| succoa + NADH + H+ → sucsa + NAD + coa | 4.4 | 7.0 | 6.2 |
| sucsa + NADH + H+ → 4-HB + NAD | −5.0 | −3.8 | −4.6 |

The first column is under standard conditions, while the others are adjusted according to equation 1.
Temperature is constant at 298 K.
Error bars for these values are on the order of 8 kcal/mol, as calculated by equation 2.
Abbreviations:
suc, succinate;
sucsa, succinic semialdehyde;
succoa, succinyl-CoA;
Pi, inorganic phosphate.

Table 2 reveals that the reaction most likely to encounter a thermodynamic barrier after considering potential uncertainty in our calculations is succinic semialdehyde dehydrogenase (step 1 in FIG. 2). Whether this reaction can be driven closer to thermodynamic feasibility by varying the assumed concentrations of the participating metabolites also was studied. For example, the standard Gibbs energies assume concentrations of 1 M for all participating compounds (except water). In an anaerobic environment, NADH will be present at a several-fold higher concentration than NAD. Assuming [NADH]=5×[NAD], we calculated the effect on $\Delta G_r'$ using the equation $$\Delta G_f' = \Delta G_f^{o'} + RT \ln \frac{\prod [prod]}{\prod [react]} \quad (3)$$

This change results in a difference of about 1 kcal/mol in the delta G values for succinic semialdehyde dehydrogenase. Equation 3 was also used to calculate other effects on $\Delta G_r$, such as high succinate concentration to drive the reactions. A 1000-fold difference in the concentrations of succinate and succinic semialdehyde will contribute about 5 kcal/mol to delta G. Taken together with an assumed uncertainty of 8 kcal/mol, the possibility that succinic semialdehyde dehydrogenase will operate in the direction towards succinic semialdehyde under some set of physiological conditions cannot be eliminated. Thus, the direct route from succinate to 4-HB remains a consideration in subsequent analysis.

The microbial production capabilities of 4-hydroxybutyrate were explored in two microbes, *Escherichia coli* and *Saccharomyces cerevisiae*, using in silico metabolic models of each organism. Potential pathways to 4-HB proceed via a succinate, succinyl-CoA, or alpha-ketoglutarate intermediate as shown in FIG. 2.

A first step in the 4-HB production pathway from succinate involves the conversion of succinate to succinic semialdehyde via an NADH- or NADPH-dependant succinic semialdehyde dehydrogenase. In *E. coli*, gabD is an NADP-dependant succinic semialdehyde dehydrogenase and is part of a gene cluster involved in 4-aminobutyrate uptake and degradation (Niegemann et al., *Arch. Microbiol.* 160:454-460 (1993); Schneider et al., *J. Bacteriol.* 184:6976-6986 (2002)). sad is believed to encode the enzyme for NAD-dependant succinic semialdehyde dehydrogenase activity (Marek and Henson, supra). *S. cerevisiae* contains only the NADPH-dependant succinic semialdehyde dehydrogenase, putatively assigned to UGA2, which localizes to the cytosol (Huh et al., *Nature* 425:686-691 (2003)). The maximum yield calculations assuming the succinate pathway to 4-HB in both *E. coli* and *S. cerevisiae* require only the assumption that a non-native 4-HB dehydrogenase has been added to their metabolic networks.

The pathway from succinyl-CoA to 4-hydroxybutyrate was described in U.S. Pat. No. 6,117,658 as part of a process for making polyhydroxyalkanoates comprising 4-hydroxybutyrate monomer units. *Clostridium kluyveri* is one example organism known to possess CoA-dependant succinic semialdehyde dehydrogenase activity (Sohling and Gottschalk, supra; Sohling and Gottschalk, supra). In this study, it is assumed that this enzyme, from *C. kluyveri* or another organism, is expressed in *E. coli* or *S. cerevisiae* along with a non-native or heterologous 4-HB dehydrogenase to complete the pathway from succinyl-CoA to 4-HB. The pathway from alpha-ketoglutarate to 4-HB was demonstrated in *E. coli* resulting in the accumulation of poly(4-hydroxybutyric acid) to 30% of dry cell weight (Song et al., supra). As *E. coli* and *S. cerevisiae* natively or endogenously possess both glutamate:succinic semialdehyde transaminase and glutamate decarboxylase (Coleman et al., *J. Biol. Chem.* 276:244-250 (2001)), the pathway from AKG to 4-HB can be completed in both organisms by assuming only that a non-native 4-HB dehydrogenase is present.

EXAMPLE II

Production of 4-Hydroxybutanoic Acid in *E. coli*

This Example describes the biosynthetic yields for 4-hydroxybutanoic acid resulting from each biochemical pathway.

In this section, the maximum theoretical yields of 4-HB from glucose are calculated assuming that each of the three metabolic pathways depicted in FIG. 2 are functional in *E. coli*. A genome-scale metabolic model of *E. coli*, similar to the one described in Reed et al., *Genome Biol.* 4:R54 (2003), was used as the basis for the analysis. The energetic gain, in terms of ATP molecules produced, of each maximum yielding pathway is calculated assuming anaerobic conditions, unless otherwise stated. 4-Hydroxybutyrate is assumed to exit in *E. coli* via proton symport, as is the case with most organic acids. It is also possible that GBL is secreted by simple diffusion, and in this case the energetics would be more favorable than in the case considered here. The impact of cofactor specificity (i.e., NADH or NADPH-dependence) of the participating enzymes on the maximum yield and energetics of each pathway also was investigated.

The results from the analysis are shown in Tables 3 A-C. From an energetic and yield standpoint, the succinate to 4-HB pathway is the most promising. Specifically, the calculations reveal that the maximum theoretical yield of 4-HB from glucose is 1.33 mol/mol (0.77 g/g; 0.89 Cmol/Cmol) assuming the succinate to 4-HB pathway is functional. In addition, the anaerobic production of 4-HB via succinate would result in the net production of either 1.8, 1.5, or 1.1 mol of ATP per glucose depending upon the assumed cofactor specificity of the participating enzymes. These energetic yields are comparable to the 2.0 ATP per glucose that can be obtained via substrate level phosphorylation by the production of ethanol or lactate suggesting the potential for anaerobic homo-4-HB production in *E. coli*.

The succinyl-CoA route to 4-HB is another promising pathway when considering maximum yield and energetics. A 1.33 mol/mol yield of 4-HB is achievable in *E. coli* if at least one of the pathway steps is assumed NADH-dependant. However, because this pathway requires the formation of succinyl-CoA, its energetic yield is lower than that of the succinate pathway. An oxygen requirement is anticipated at high 4-HB yields if both the CoA-dependant succinic semialdehyde dehydrogenase and 4-HB dehydrogenase steps are assumed NADPH-dependant. In this case, the production of 4-HB at the maximum yield would result in no net ATP gain and possibly not support the energetic maintenance demands needed for *E. coli* survival. Thus, some energy would have to originate from oxidative phosphorylation to enable homo-fermentative 4-HB production. The alpha-ketoglutarate pathway utilizing glutamate:succinate semialdehyde transaminase and glutamate decarboxylase toward 4-HB is the least favorable of the three potential routes with a maximum achievable yield of 1.0 mol 4-HB per mol of glucose. In addition to the lower maximum yield, this pathway requires the utilization of 1.5 moles of oxygen per mol of glucose converted to 4-HB. The energetics of this pathway are unaffected by the assumed cofactor specificity of 4-HB dehydrogenase.

TABLE 3

The overall substrate conversion stoichiometry to 4-HB assuming the A) succinate, B) succinyl-CoA, or C) alpha-ketoglutarate production routes are functional in *E. coli*. Glucose and oxygen are taken up while all other molecules are produced.

A) Succinate Pathway

| Cofactor Specificity | 2 NADH steps | 1 NADH step 1 NADPH step | 2 NADPH steps |
|---|---|---|---|
| Glucose | −1.000 | −1.000 | −1.000 |
| Oxygen | 0.000 | 0.000 | 0.000 |
| Protons | 1.333 | 1.333 | 1.333 |

TABLE 3-continued

The overall substrate conversion stoichiometry to 4-HB assuming the A) succinate, B) succinyl-CoA, or C) alpha-ketoglutarate production routes are functional in *E. coli*. Glucose and oxygen are taken up while all other molecules are produced.

| | | | |
|---|---|---|---|
| 4HB | 1.333 | 1.333 | 1.333 |
| CO2 | 0.667 | 0.667 | 0.667 |
| H2O | 0.667 | 0.667 | 0.667 |
| ATP | 1.800 | 1.510 | 1.097 |

B) Succinyl-CoA Pathway

| Cofactor Specificity | 2 NADH steps | 1 NADH step 1 NADPH step | 2 NADPH steps | 2 NADPH steps |
|---|---|---|---|---|
| Glucose | −1.000 | −1.000 | −1.000 | −1.000 |
| Oxygen | 0.000 | 0.000 | −0.036 | 0.000 |
| Protons | 1.333 | 1.333 | 1.325 | 1.294 |
| 4HB | 1.333 | 1.333 | 1.325 | 1.294 |
| CO2 | 0.667 | 0.667 | 0.698 | 0.082 |
| H2O | 0.667 | 0.667 | 0.698 | 0.470 |
| ATP | 0.467 | 0.177 | 0.000 | 0.000 |

C) Alpha-ketoglutarate Pathway

| Cofactor Specificity | 1 NADH step | 1 NADPH step |
|---|---|---|
| Glucose | −1.000 | −1.000 |
| Oxygen | −1.500 | −1.500 |
| Protons | 1.000 | 1.000 |
| 4HB | 1.000 | 1.000 |
| CO2 | 2.000 | 2.000 |
| H2O | 2.000 | 2.000 |
| ATP | 5.500 | 5.500 |

In order to corroborate the computational predictions proposed in this report, the strains expressing a complete pathway to 4-HB can be constructed and tested. Corroboration is performed with both *E. coli* (Examples II and IV) and *S. cerevisiae* (Example III). In *E. coli*, the relevant genes are expressed in a synthetic operon behind an inducible promoter on a medium- or high-copy plasmid; for example the $P_{BAD}$ promoter which is induced by arabinose, on a plasmid of the pBAD series (Guzman et al., *J. Bacteriol.* 177:4121-4130 (1995)). In *S. cerevisiae*, genes are integrated into the chromosome behind the PDC1 promoter, replacing the native pyruvate carboxylase gene. It has been reported that this results in higher expression of foreign genes than from a plasmid (Ishida et al., *Appl. Environ. Microbiol.* 71:1964-1970 (2005)), and will also ensure expression during anaerobic conditions.

Cells containing the relevant constructs are grown in minimal media containing glucose, with addition of arabinose in the case of *E. coli* containing genes expressed under the $P_{BAD}$ promoter. Periodic samples are taken for both gene expression and enzyme activity analysis. Enzyme activity assays are performed on crude cell extracts using procedures well known in the art. Alternatively, assays based on the oxidation of NAD(P)H, which is produced in all dehydrogenase reaction steps and detectable by spectrophotometry can be utilized. In addition, antibodies can be used to detect the level of particular enzymes. In lieu of or in addition to enzyme activity measurements, RNA can be isolated from parallel samples and transcript of the gene of interest measured by reverse transcriptase PCR. Any constructs lacking detectable transcript expression are reanalyzed to ensure the encoding nucleic acids are harbored in an expressible form. Where transcripts are detected, this result indicates either a lack of translation or production of inactive enzyme. A variety of methods well known in the art can additionally be employed, such as codon optimization, engineering a strong ribosome binding site, use of a gene from a different species, and prevention of N-glycosylation (for expression of bacterial enzymes in yeast) by conversion of Asn residues to Asp. Once all required enzyme activities are detected, the next step is to measure the production of 4-HP in vivo. Triplicate shake flask cultures are grown either anaerobically or microaerobically, depending on the conditions required (see above), and periodic samples taken. Organic acids present in the culture supernatants are analyzed by HPLC using the Aminex AH-87× column. The elution time of 4-HB will be determined using a standard purchased from a chemical supplier.

The CoA-independent pathway can be implemented and tested for corroboration. In this case, the genes overexpressed are the native succinic semialdehyde dehydrogenase from each organism, and the 4-hydroxybutanoate dehydrogenase from *Ralstonia eutropha*. Once both enzyme activities are detected as discussed above, the strains are tested for 4-HB production. Corroboration also can be obtained from implementing the CoA-dependent pathway. The CoA-dependent succinic semialdehyde dehydrogenase and the 4-hydroxybutanoate dehydrogenase from *Clostridium kluyveri* are expressed as described above. In addition, overexpression of the native succinyl-CoA synthetase also can be performed, to funnel more succinate into the heterologous pathway. Finally, if 4-HB production is unfavorable, different culture conditions can be tested, such as a change in oxygenation status which can manipulate the NAD(P)H/NAD(P) ratio.

EXAMPLE III

Production of 4-Hydroxybutanoic Acid in Yeast

This Example describes the biosynthetic yields for 4-hydroxybutanoic acid resulting from each biochemical pathway in *S. cerevisiae*.

In this section, the maximum theoretical yields of 4-HB from glucose are calculated assuming that each of the three metabolic pathways depicted in FIG. 2 are functional in *S. cerevisiae*. A genome-scale metabolic model of *S. cerevisiae*, similar to the one described in Forster et al. *Genome Res.* 13:244-253 (2003) was used as the basis for the analysis. The energetic gain of each maximum yielding pathway is calculated assuming anaerobic conditions unless otherwise stated. 4-hydroxybutyrate is assumed to exit *S. cerevisiae* via proton symport, as is the case with most organic acids. The impact of cofactor specificity (i.e., NADH or NADPH-dependence) of the participating enzymes on the maximum yield and energetics of each pathway was also investigated.

The results from the analysis are shown in Tables 4 A-C. As with *E. coli*, the succinate to 4-HB pathway is the most promising provided that the thermodynamic concerns raised in Example I can be overcome. The calculations reveal that the maximum theoretical yield of 4-HB from glucose is 1.33 mol/mol (0.77 g/g; 0.89 Cmol/Cmol) in *S. cerevisiae*. In addition, the anaerobic production of 4-HB via succinate would result in the net production of either 1.4, 1.1, or 0.5 mol of ATP per glucose depending upon the assumed cofactor specificity of the participating enzymes.

The succinyl-CoA route to 4-HB is the second most favorable pathway. A maximum yield of 1.33 mol 4-HB/mol glucose is achievable in *S. cerevisiae* regardless of cofactor specificity. However, net energy generation at the maximum theoretical yield is possible only if both the CoA-dependant succinic semialdehyde dehydrogenase and 4-HB dehydrogenase steps are assumed to be NADH-dependant. If either step is NADPH-dependant, no net ATP will be gained from anaerobic 4-HB production and an alternate energy source (e.g., oxidative phosphorylation) would be required to support cell growth and maintenance. The alpha-ketoglutarate route toward 4-HB is the least favorable of the three potential pathways in *S. cerevisiae* although the maximum yield of 1.1-1.2 mol 4-HB per mol glucose is slightly higher than was found in *E. coli*. Nevertheless, this pathway requires an oxygen uptake of 0.8-0.9 mol oxygen per mol glucose to become energetically neutral.

TABLE 4

The overall substrate conversion stoichiometry to 4-HB in *S. cerevisiae*., assuming the A) succinate, B) succinyl-CoA, or C) alpha-ketoglutarate production routes are functional in *S. cerevisiae*. Glucose and oxygen are taken up while all other molecules are produced.

| Cofactor Specificity | 2 NADH steps | 1 NADH step 1 NADPH step | 2 NADPH steps |
|---|---|---|---|
| A) Succinate Pathway | | | |
| Glucose | −1.000 | −1.000 | −1.000 |
| Oxygen | 0.000 | 0.000 | 0.000 |
| Protons | 1.333 | 1.333 | 1.333 |
| 4HB | 1.333 | 1.333 | 1.333 |
| CO2 | 0.667 | 0.667 | 0.667 |
| H2O | 0.667 | 0.667 | 0.667 |
| ATP | 1.444 | 1.067 | 0.533 |
| B) Succinyl-CoA Pathway | | | |
| Glucose | −1.000 | −1.000 | −1.000 |
| Oxygen | 0.000 | 0.000 | 0.000 |
| Protons | 1.333 | 1.333 | 1.333 |
| 4HB | 1.333 | 1.333 | 1.333 |
| CO2 | 0.667 | 0.667 | 0.667 |
| H2O | 0.667 | 0.667 | 0.667 |
| ATP | 0.533 | 0.000 | 0.000 |

C) Alpha-ketoglutarate Pathway

| Cofactor Specificity | 1 NADH step | 1 NADPH step |
|---|---|---|
| Glucose | −1.000 | −1.000 |
| Oxygen | −0.785 | −0.879 |
| Protons | 1.159 | 1.138 |
| 4HB | 1.159 | 1.138 |
| CO2 | 1.364 | 1.448 |
| H2O | 1.364 | 1.448 |
| ATP | 0.000 | 0.000 |

EXAMPLE IV

Biosynthesis of 1,4-Butanediol from Succinate and α-Ketogluterate

This Example illustrates the construction and biosynthetic production of 4-HB and BDO from microbial organisms.

As described previously in Examples I-III, the thermodynamic characteristics of the biotransformation steps from 4-HB to BDO shown in FIG. 1 also were calculated based on standard Gibbs free energy of formation determined by group contribution. The results are provide in Table 5. Similarly, although some of the steps have calculated positive delta G values, the standard errors for these calculations and concentration gradients indicate that any of the steps are feasible.

TABLE 5

Gibbs free energy of reaction (kcal/mole) under standard conditions (pH and ionic strength values).

| Reaction | $\Delta G_r^{o'}$ pH = 7.0 IS = 0 |
|---|---|
| 4-HB + NADH + H+ → 4-HBald + NAD | 2.4 |
| 4-HB + acetyl-CoA → 4-HB-CoA + acetate | −5.0 |

TABLE 5-continued

Gibbs free energy of reaction (kcal/mole) under standard conditions (pH and ionic strength values).

| Reaction | $\Delta G_r^{o'}$ pH = 7.0 IS = 0 |
|---|---|
| 4-HB-CoA + NADH + H+ → 4-HBald + NAD + CoA | 9.5 |
| 4-HBald + NADH + H+ → bdo + NAD | −5.0 |

Temperature was constant at 298 K.
Error bars for these values are on the order of 8 kcal/mol, as calculated by equation 2.
Abbreviations:
4-HBald, 4-hydroxybutyraldehyde.

Theoretical yields were calculated assuming all the pathways in FIG. 2 are incorporated into *E. coli*. A genome-scale metabolic model of *E. coli*, similar to the one described in Reed et al., *Genome Biol* 4:R54 (2003), was used as the basis for the analysis. The maximum theoretical yield assuming energetic neutrality and no cell growth or maintenance was 1.09 mol BDO/mol glucose under microaerobic conditions. Simulations performed under anaerobic conditions, which can be utilized to drive the pathway toward BDO production, either acetate or ethanol is produced as a co-product. Under these conditions, the maximum yields were 1.04 and 1.00 mol/mol, respectively. One alternative is to add limiting amounts of nitrate as an electron acceptor, thus controlling the amount of respiration that can occur. Under this condition, the maximum yield returns to 1.09 mol/mol. Another alternative is to replace the native *E. coli* phosphoenolpyruvate (PEP) carboxylase with a heterologous or engineered phosphoenolpyruvate carboxykinase that is capable of functioning in the direction of PEP carboxylation. This enzyme produces ATP, whereas the PEP carboxylase does not. Under this assumption, the maximum yield returns to 1.09 mol/mol.

In addition, there are several alternative enzymes that can be utilized in the pathway described above. The native or endogenous enzyme for conversion of succinate to succinyl-CoA (Step 1 in FIG. 2) can be replaced by a CoA transferase such as that encoded by the cat1 gene *C. kluyveri* (Sohling, B. and G. Gottschalk, *Eur. J. Biochem.* 212:121-127 (1993)), which functions in a similar manner to Step 9. However, the production of acetate by this enzyme may not be optimal, as it might be secreted rather than being converted back to acetyl-CoA. In this respect, it also can be beneficial to eliminate acetate formation in Step 9. As one alternative to this CoA transferase, a mechanism can be employed in which the 4-HB is first phosphorylated by ATP and then converted to the CoA derivative, similar to the acetate kinase/phosphotransacetylase pathway in *E. coli* for the conversion of acetate to acetyl-CoA. The net cost of this route is one ATP, which is the same as is required to regenerate acetyl-CoA from acetate. The enzymes phosphotransbutyrylase (ptb) and butyrate kinase (bk) are known to carry out these steps on the non-hydroxylated molecules for butyrate production in *C. acetobutylicum* (Cary et al., *Appl Environ Microbiol* 56:1576-1583 (1990); Valentine, R. C. and R. S. Wolfe, *J Biol Chem.* 235: 1948-1952 (1960)). These enzymes are reversible, allowing synthesis to proceed in the direction of 4-HB.

BDO also can be produced via α-ketoglutarate in addition to or instead of through succinate. A described previously, and exemplified further below, one pathway to accomplish product biosynthesis is with the production of succinic semialdehyde via α-ketoglutarate using the endogenous enzymes (FIG. 2, Steps 4-5). An alternative is to use an α-ketoglutarate decarboxylase that can perform this conversion in one step (FIG. 2, Step 8; Tian et al., *Proc Natl Acad Sci USA* 102: 10670-10675 (2005)).

For the construction of different strains of BDO-producing microbial organisms, a list of applicable genes was assembled for corroboration. Briefly, one or more genes within the 4-HB and/or BDO biosynthetic pathways were identified for each step of the complete BDO-producing pathway shown in FIG. 2, using available literature resources, the NCBI genetic database, and homology searches. The genes cloned and assessed in this study are presented below in Table 6, along with the appropriate references and URL citations to the polypeptide sequence. As discussed further below, some genes were synthesized for codon optimization while others were cloned via PCR from the genomic DNA of the native or wild-type organism. For some genes both approaches were used, and in this case the native genes are indicated by an "n" suffix to the gene identification number when used in an experiment. Note that only the DNA sequences differ; the proteins are identical.

TABLE 6

Genes expressed in host BDO-producting microbial organisms.

| Gene ID number | Reaction number (FIG. 1) | Gene name | Source organism | Enzyme name | URL link to protein sequence | Reference |
|---|---|---|---|---|---|---|
| 0001 | 9 | Cat2 | *Clostridium kluyveri* DSM 555 | 4-hydroxybutyrate coenzyme A transferase | ncbi.nlm.nih.gov/entrez/ viewer.fcgi?db=nuccore&id=1228100 | (29)d} |
| 0002 | 12/13 | adhE | *Clostridium acetobutylicum* ATCC 824 | Aldehyde/alcohol dehydrogenase | ncbi.nlm.nih.gov/entrez/ viewer.fcgi?db=protein&val=15004739 | (22)d} |
| 0003 | 12/13 | adhE2 | *Clostridium acetobutylicum* ATCC 824 | Aldehyde/alcohol dehydrogenase | ncbi.nlm.nih.gov/entrez/ viewer.fcgi?val=NP_149325.1 | (12)d} |
| 0004 | 1 | Cat1 | *Clostridium kluyveri* DSM 555 | Succinate coenzyme A transferase | ncbi.nlm.nih.gov/entrez/ viewer.fcgi?db=nuccore&id=1228100 | (29)d} |
| 0008 | 6 | sucD | *Clostridium kluyveri* DSM 555 | Succinic semialdehyde dehydrogenase (CoA-dependent) | ncbi.nlm.nih.gov/entrez/ viewer.fcgi?db=nuccore&id=1228100 | (29)d} |
| 0009 | 7 | 4-HBd | *Ralstonia eutropha H16* | 4-hydroxybutyrate dehydrogenase (NAD-dependent) | ncbi.nlm.nih.gov/entrez/ viewer.fcgi?val=YP_726053.1 | (32)d} |

TABLE 6-continued

Genes expressed in host BDO-producting microbial organisms.

| Gene ID number | Reaction number (FIG. 1) | Gene name | Source organism | Enzyme name | URL link to protein sequence | Reference |
|---|---|---|---|---|---|---|
| 0010 | 7 | 4-HBd | *Clostridium kluyveri* DSM 555 | 4-hydroxybutyrate dehydrogenase (NAD-dependent) | ncbi.nlm.nih.gov/entrez/viewer.fcgi?db=nuccore&id=1228100 | (29)d} |
| 0011 | 12/13 | adhE | *E. coli* | Aldehyde/alcohol dehydrogenase | shigen.nig.ac.jp/ecoli/pec/genes.List.DetailAction.do?fromListFlag=true&featureType=1&orfId=1219 | |
| 0012 | 12/13 | yqhD | *E. coli* | Aldehyde/alcohol dehydrogenase | shigen.nig.ac.jp/ecoli/pec/genes.List.DetailAction.do | |
| 0013 | 13 | bdhB | *Clostridium acetobutylicum* ATCC 824 | Butanol dehydrogenase II | ncbi.nlm.nih.gov/entrez/viewer.fcgi?val=NP_349891.1 | (35)d} |
| 0020 | 11 | ptb | *Clostridium acetobutylicum* ATCC 824 | Phospho-transbutyrylase | ncbi.nlm.nih.gov/entrez/viewer.fcgi?db=protein&id=15896327 | (4)d} |
| 0021 | 10 | buk1 | *Clostridium acetobutylicum* ATCC 824 | Butyrate kinase I | ncbi.nlm.nih.gov/entrez/viewer.fcgi?db=protein&id=20137334 | (4)d} |
| 0022 | 10 | buk2 | *Clostridium acetobutylicum* ATCC 824 | Butyrate kinase II | ncbi.nlm.nih.gov/entrez/viewer.fcgi?db=protein&id=20137415 | (4)d} |
| 0023 | 13 | adhEm | isolated from metalibrary of anaerobic sewage digester microbial consortia | Alcohol dehydrogenase | | (37)d} |
| 0024 | 13 | adhE | *Clostridium thermocellum* | Alcohol dehydrogenase | genome.jp/dbget-bin/www_bget?cth:Cthe_0423 | |
| 0025 | 13 | ald | *Clostridium beijerinckii* | Coenzyme A-acylating aldehyde dehydrogenase | ncbi.nlm.nih.gov/entrez/viewer.fcgi?db=protein&id=49036681 | (31)d} |
| 0026 | 13 | bdhA | *Clostridium acetobutylicum* ATCC 824 | Butanol dehydrogenase | ncbi.nlm.nih.gov/entrez/viewer.fcgi?val=NP_349892.1 | (35)d} |
| 0027 | 12 | bld | *Clostridium saccharoperbutylacetonicum* | Butyraldehyde dehydrogenase | ncbi.nlm.nih.gov/entrez/viewer.fcgi?db=protein&id=31075383 | (18)d} |
| 0028 | 13 | bdh | *Clostridium saccharoperbutylacetonicum* | Butanol dehydrogenase | ncbi.nlm.nih.gov/entrez/viewer.fcgi?db=protein&id=124221917 | (18)d} |
| 0029 | 12/13 | adhE | *Clostridium tetani* | Aldehyde/alcohol dehydrogenase | genome.jp/dbget-bin/www_bget?ctc:CTC01366 | |
| 0030 | 12/13 | adhE | *Clostridium perfringens* | Aldehyde/alcohol dehydrogenase | genome.jp/dbget-bin/www_bget?cpe:CPE2531 | |
| 0031 | 12/13 | adhE | *Clostridium difficile* | Aldehyde/alcohol dehydrogenase | genome.jp/dbget-bin/www_bget?cdf:CD2966 | |
| 0032 | 8 | sucA | *Mycobacterium bovis* BCG, Pasteur | α-ketoglutarate decarboxylase | ncbi.nlm.nih.gov/entrez/viewer.fcgi?val=YP_977400.1 | (30)d} |
| 0033 | 9 | cat2 | *Clostridium aminobutyricum* | 4-hydroxybutyrate coenzyme A transferase | ncbi.nlm.nih.gov/entrez/viewer.fcgi?db=protein&val=6249316 | |
| 0034 | 9 | cat2 | *Porphyromonas gingivalis* W83 | 4-hydroxybutyrate coenzyme A transferase | ncbi.nlm.nih.gov/entrez/viewer.fcgi?db=protein&val=34541558 | |
| 0035 | 6 | sucD | *Porphyromonas gingivalis* W83 | Succinic semialdehyde dehydrogenase (CoA-dependent) | ncbi.nlm.nih.gov/entrez/viewer.fcgi?val=NP_904963.1 | |
| 0036 | 7 | 4-HBd | *Porphyromonas gingivalis* W83 | NAD-dependent 4-hydroxybutyrate dehydrogenase | ncbi.nlm.nih.gov/entrez/viewer.fcgi?val=NP_904964.1 | |
| 0037 | 7 | gbd | Uncultured bacterium | 4-hydroxybutyrate dehydrogenase | ncbi.nlm.nih.gov/entrez/viewer.fcgi?db=nuccore&id=5916168 | (16)d} |
| 0038 | 1 | sucCD | *E. coli* | Succinyl-CoA synthetase | shigen.nig.ac.jp/ecoli/pec/genes.List.DetailAction.do | |

Expression Vector Construction for BDO pathway. Vector backbones and some strains were obtained from Dr. Rolf Lutz of Expressys (www.expressys.de/). The vectors and strains are based on the pZ Expression System developed by Dr. Rolf Lutz and Prof. Hermann Bujard (Lutz, R. and H. Bujard, *Nucleic Acids Res* 25:1203-1210 (1997)). Vectors obtained were pZE13luc, pZA33luc, pZS*13luc and pZE22luc and contained the luciferase gene as a stuffer fragment. To replace the luciferase stuffer fragment with a lacZ-alpha fragment flanked by appropriate restriction enzyme sites, the luciferase stuffer fragment was first removed from each vector by digestion with EcoRI and XbaI. The lacZ-alpha fragment was PCR amplified from pUC19 with the following primers:

```
                                         (SEQ ID NO: 1)
lacZalpha-RI
5'GACGAATTCGCTAGCAAGAGGAGAAGTCGACATGTCCAATTCACTGGC
CGTCGTTTTAC3'

(SEQ ID NO: 2)
lacZalpha 3'BB
5'-GACCCTAGGAAGCTTTCTAGAGTCGACCTATGCGGCATCAGAGCAG
A-3'.
```

This generated a fragment with a 5' end of EcoRI site, NheI site, a Ribosomal Binding Site, a SalI site and the start codon. On the 3' end of the fragment contained the stop codon, XbaI, HindIII, and AvrII sites. The PCR product was digested with EcoRI and AvrII and ligated into the base vectors digested with EcoRI and XbaI (XbaI and AvrII have compatible ends and generate a non-site). Because NheI and XbaI restriction enzyme sites generate compatible ends that can be ligated together (but generate a NheI/XbaI non-site that is not digested by either enzyme), the genes cloned into the vectors could be "Biobricked" together (http://openwetware.org/wiki/Synthetic_Biology:BioBricks). Briefly, this method enables joining an unlimited number of genes into the vector using the same 2 restriction sites (as long as the sites do not appear internal to the genes), because the sites between the genes are destroyed after each addition.

All vectors have the pZ designation followed by letters and numbers indication the origin of replication, antibiotic resistance marker and promoter/regulatory unit. The origin of replication is the second letter and is denoted by E for ColE1, A for p15A and S for pSC101-based origins. The first number represents the antibiotic resistance marker (1 for Ampicillin, 2 for Kanamycin, 3 for Chloramphenicol, 4 for Spectinomycin and 5 for Tetracycline). The final number defines the promoter that regulated the gene of interest (1 for $P_{LtetO-1}$, 2 for $P_{LlacO-1}$, 3 for $P_{AllacO-1}$, and 4 for $P_{lac/ara-1}$). The MCS and the gene of interest follows immediately after. For the work discussed here we employed two base vectors, pZA33 and pZE13, modified for the biobricks insertions as discussed above. Once the gene(s) of interest have been cloned into them, resulting plasmids are indicated using the four digit gene codes given in Table 6; e.g., pZA33-XXXX-YYYY-....

Host Strain Construction. The parent strain in all studies described here is *E. coli* K-12 strain MG1655. Markerless deletion strains in adhE, gabD, and aldA were constructed under service contract by a third party using the redET method (Datsenko, K. A. and B. L. Wanner, *Proc Natl Acad Sci USA* 97:6640-6645 (2000)). Subsequent strains were constructed via bacteriophage P1 mediated transduction (Miller, J. 1973. Experiments in Molecular Genetics. Cold Spring Harbor Laboratories, New York). Strain C600Z1 (lacI$^q$, PN25-tetR, Sp$^R$, lacY1, leuB6,mcrB+, supE44, thi-1, thr-1, tonA21) was obtained from Expressys and was used as a source of a lacI$^q$ allele for P1 transduction. Bacteriophage P1vir was grown on the C600Z1 *E. coli* strain, which has the spectinomycin resistance gene linked to the lacI$^q$. The P1 lysate grown on C600Z1 was used to infect MG1655 with selection for spectinomycin resistance. The spectinomycin resistant colonies were then screened for the linked lacI$^q$ by determining the ability of the transductants to repress expression of a gene linked to a $P_{AllacO-1}$ promoter. The resulting strain was designated MG1655 lacI$^q$. A similar procedure was used to introduce lacI$^Q$ into the deletion strains.

Production of 4-HB From Succinate. For construction of a 4-HB producer from succinate, genes encoding steps from succinate to 4-HB and 4-HB-CoA (1, 6, 7, and 9 in FIG. 2) were assembled onto the pZA33 and pZE13 vectors as described below. Various combinations of genes were assessed, as well as constructs bearing incomplete pathways as controls (Tables 7 and 8). The plasmids were then transformed into host strains containing lacI$^Q$, which allow inducible expression by addition of isopropyl β-D-1-thiogalactopyranoside (IPTG). Both wild-type and hosts with deletions in genes encoding the native succinic semialdehyde dehydrogenase (step 2 in FIG. 1) were tested.

Activity of the heterologous enzymes were first tested in in vitro assays, using strain MG1655 lacI$^Q$ as the host for the plasmid constructs containing the pathway genes. Cells were grown aerobically in LB media (Difco) containing the appropriate antibiotics for each construct, and induced by addition of IPTG at 1 mM when the optical density (OD600) reached approximately 0.5. Cells were harvested after 6 hours, and enzyme assays conducted as discussed below.

In Vitro Enzyme Assays. To obtain crude extracts for activity assays, cells were harvested by centrifugation at 4,500 rpm (Beckman-Coulter, Allegera X-15R) for 10 min. The pellets were resuspended in 0.3 mL BugBuster (Novagen) reagent with benzonase and lysozyme, and lysis proceeded for 15 minutes at room temperature with gentle shaking. Cell-free lysate was obtained by centrifugation at 14,000 rpm (Eppendorf centrifuge 5402) for 30 min at 4° C. Cell protein in the sample was determined using the method of Bradford et al., *Anal. Biochem.* 72:248-254 (1976), and specific enzyme assays conducted as described below. Activities are reported in Units/mg protein, where a unit of activity is defined as the amount of enzyme required to convert 1 μmol of substrate in 1 min. at room temperature. In general, reported values are averages of at least 3 replicate assays.

Succinyl-CoA transferase (Cat1) activity was determined by monitoring the formation of acetyl-CoA from succinyl-CoA and acetate, following a previously described procedure Sohling and Gottschalk, *J. Bacteriol.* 178:871-880 (1996). Succinyl-CoA synthetase (SucCD) activity was determined by following the formation of succinyl-CoA from succinate and CoA in the presence of ATP. The experiment followed a procedure described by Cha and Parks, *J. Biol. Chem.* 239: 1961-1967 (1964). CoA-dependent succinate semialdehyde dehydrogenase (SucD) activity was determined by following the conversion of NAD to NADH at 340 nm in the presence of succinate semialdehyde and CoA (Sohling and Gottschalk, *Eur. J. Biochem.* 212:121-127 (1993)). 4-HB dehydrogenase (4-HBd) enzyme activity was determined by monitoring the oxidation of NADH to NAD at 340 nm in the presence of succinate semialdehyde. The experiment followed a published procedure Gerhardt et al. *Arch. Microbiol.* 174:189-199 (2000). 4-HB CoA transferase (Cat2) activity was determined using a modified procedure from Scherf and Buckel, *Appl. Environ. Microbiol.* 57:2699-2702 (1991). The formation of 4-HB-CoA or butyryl-CoA formation from acetyl-CoA and 4-HB or butyrate was determined using HPLC.

Alcohol (ADH) and aldehyde (ALD) dehydrogenase was assayed in the reductive direction using a procedure adapted from several literature sources (Durre et al., *FEMS Microbiol. Rev.* 17:251-262 (1995); Palosaari and Rogers, *J. Bacteriol.* 170:2971-2976 (1988) and Welch et al., *Arch. Biochem. Biophys.* 273:309-318 (1989). The oxidation of NADH is followed by reading absorbance at 340 nM every four seconds for a total of 240 seconds at room temperature. The reductive assays were performed in 100 mM MOPS (adjusted to pH 7.5 with KOH), 0.4 mM NADH, and from 1 to 50 µl of cell extract. The reaction is started by adding the following reagents: 100 µl of 100 mM acetaldehyde or butyraldehyde for ADH, or 100 µl of 1 mM acetyl-CoA or butyryl-CoA for ALD. The Spectrophotometer is quickly blanked and then the kinetic read is started. The resulting slope of the reduction in absorbance at 340 nM per minute, along with the molar extinction coefficient of NAD(P)H at 340 nM (6000) and the protein concentration of the extract, can be used to determine the specific activity.

The enzyme activity of PTB is measured in the direction of butyryl-CoA to butyryl-phosphate as described in Cary et al. *J. Bacteriol.* 170:4613-4618 (1988). It provides inorganic phosphate for the conversion, and follows the increase in free CoA with the reagent 5,5'-dithiobis-(2-nitrobenzoic acid), or DTNB. DTNB rapidly reacts with thiol groups such as free CoA to release the yellow-colored 2-nitro-5-mercaptobenzoic acid (TNB), which absorbs at 412 nm with a molar extinction coefficient of 14,140 M cm$^{-1}$. The assay buffer contained 150 mM potassium phosphate at pH 7.4, 0.1 mM DTNB, and 0.2 mM butyryl-CoA, and the reaction was started by addition of 2 to 50 µL cell extract. The enzyme activity of BK is measured in the direction of butyrate to butyryl-phosphate formation at the expense of ATP. The procedure is similar to the assay for acetate kinase previously described Rose et al., *J. Biol. Chem.* 211:737-756 (1954). However we have found another acetate kinase enzyme assay protocol provided by Sigma to be more useful and sensitive. This assay links conversion of ATP to ADP by acetate kinase to the linked conversion of ADP and phosphoenol pyruvate (PEP) to ATP and pyruvate by pyruvate kinase, followed by the conversion of pyruvate and NADH to lactate and NAD+ by lactate dehydrogenase. Substituting butyrate for acetate is the only major modification to enable the assay to follow BK enzyme activity. The assay mixture contained 80 mM triethanolamine buffer at pH 7.6, 200 mM sodium butyrate, 10 mM MgCl2, 0.1 mM NADH, 6.6 mM ATP, 1.8 mM phosphoenolpyruvate. Pyruvate kinase, lactate dehydrogenase, and myokinase were added according to the manufacturer's instructions. The reaction was started by adding 2 to 50 µL cell extract, and the reaction was monitored based on the decrease in absorbance at 340 nm indicating NADH oxidation.

Analysis of CoA Derivatives by HPLC. An HPLC based assay was developed to monitor enzymatic reactions involving coenzyme A (CoA) transfer. The developed method enabled enzyme activity characterization by quantitative determination of CoA, acetyl CoA (AcCoA), butyryl CoA (BuCoA) and 4-hydroxybutyrate CoA (4-HBCoA) present in in-vitro reaction mixtures. Sensitivity down to low µM was achieved, as well as excellent resolution of all the CoA derivatives of interest.

Chemical and sample preparation was performed as follows. Briefly, CoA, AcCoA, BuCoA and all other chemicals, were obtained from Sigma-Aldrich. The solvents, methanol and acetonitrile, were of HPLC grade. Standard calibration curves exhibited excellent linearity in the 0.01-1 mg/mL concentration range. Enzymatic reaction mixtures contained 100 mM Tris HCl buffer (pH 7), aliquots were taken at different time points, quenched with formic acid (0.04% final concentration) and directly analyzed by HPLC.

HPLC analysis was performed using an Agilent 1100 HPLC system equipped with a binary pump, degasser, thermostated autosampler and column compartment, and diode array detector (DAD), was used for the analysis. A reversed phase column, Kromasil 100 5 um C18, 4.6×150 mm (Peeke Scientific), was employed. 25 mM potassium phosphate (pH 7) and methanol or acetonitrile, were used as aqueous and organic solvents at 1 mL/min flow rate. Two methods were developed: a short one with a faster gradient for the analysis of well-resolved CoA, AcCoA and BuCoA, and a longer method for distinguishing between closely eluting AcCoA and 4-HBCoA. Short method employed acetonitrile gradient (0 min-5%, 6 min-30%, 6.5 min-5%, 10 min-5%) and resulted in the retention times 2.7, 4.1 and 5.5 min for CoA, AcCoA and BuCoA, respectively. In the long method methanol was used with the following linear gradient: 0 min-5%, 20 min-35%, 20.5 min-5%, 25 min-5%. The retention times for CoA, AcCoA, 4-HBCoA and BuCoA were 5.8, 8.4, 9.2 and 16.0 min, respectively. The injection volume was 5 µL, column temperature 30° C., and UV absorbance was monitored at 260 nm.

The results demonstrated activity of each of the four pathway steps (Table 6), though activity is clearly dependent on the gene source, position of the gene in the vector, and the context of other genes with which it is expressed. For example, gene 0035 encodes a succinic semialdehyde dehydrogenase that is more active than that encoded by 0008, and 0036 and 0010n are more active 4-HB dehydrogenase genes than 0009. There also seems to be better 4-HB dehydrogenase activity when there is another gene preceding it on the same operon.

TABLE 7

In vitro enzyme activities in cell extracts from MG1655 lacI$^Q$ containing the plasmids expressing genes in the 4-HB-CoA pathway. Activities are reported in Units/mg protein, where a unit of activity is defined as the amount of enzyme required to convert 1 µmol of substrate in 1 min. at room temperature.

| Sample # | pZE13 (a) | pZA33 (b) | OD600 | Cell Prot (c) | Cat1 | SucD | 4HBd | Cat2 |
|---|---|---|---|---|---|---|---|---|
| 1 | cat1 (0004) | | 2.71 | 6.43 | 1.232 | 0.00 | | |
| 2 | cat1 (0004)-sucD (0035) | | 2.03 | 5.00 | 0.761 | 2.57 | | |
| 3 | cat1 (0004)-sucD (0008) | | 1.04 | 3.01 | 0.783 | 0.01 | | |
| 4 | sucD (0035) | | 2.31 | 6.94 | | 2.32 | | |
| 5 | sucD (0008) | | 1.10 | 4.16 | | 0.05 | | |
| 6 | | 4hbd (0009) | 2.81 | 7.94 | 0.003 | | 0.25 | |
| 7 | | 4hbd (0036) | 2.63 | 7.84 | | | 3.31 | |
| 8 | | 4hbd (0010n) | 2.00 | 5.08 | | | 2.57 | |
| 9 | cat1 (0004)-sucD (0035) | 4hbd (0009) | 2.07 | 5.04 | 0.600 | 1.85 | 0.01 | |

TABLE 7-continued

In vitro enzyme activities in cell extracts from MG1655 lacI$^Q$ containing the
plasmids expressing genes in the 4-HB-CoA pathway. Activities are reported in Units/mg
protein, where a unit of activity is defined as the amount of enzyme required to convert 1 μmol
of substrate in 1 min. at room temperature.

| Sample # | pZE13 (a) | pZA33 (b) | OD600 | Cell Prot (c) | Cat1 | SucD | 4HBd | Cat2 |
|---|---|---|---|---|---|---|---|---|
| 10 | cat1 (0004)-sucD (0035) | 4hbd (0036) | 2.08 | 5.40 | 0.694 | 1.73 | 0.41 | |
| 11 | cat1 (0004)-sucD (0035) | 4hbd (0010n) | 2.44 | 4.73 | 0.679 | 2.28 | 0.37 | |
| 12 | cat1 (0004)-sucD (0008) | 4hbd (0009) | 1.08 | 3.99 | 0.572 | −0.01 | 0.02 | |
| 13 | cat1 (0004)-sucD (0008) | 4hbd (0036) | 0.77 | 2.60 | 0.898 | −0.01 | 0.04 | |
| 14 | cat1 (0004)-sucD (0008) | 4hbd (0010n) | 0.63 | 2.47 | 0.776 | 0.00 | 0.00 | |
| 15 | | cat2 (0034) | 2.56 | 7.86 | | | | 1.283 |
| 16 | | cat2 (0034)-4hbd (0036) | 3.13 | 8.04 | | | 24.86 | 0.993 |
| 17 | | cat2 (0034)-4hbd (0010n) | 2.38 | 7.03 | | | 7.45 | 0.675 |
| 18 | | 4hbd (0036)-cat2 (0034) | 2.69 | 8.26 | | | 2.15 | 7.490 |
| 19 | | 4hbd (0010n)-cat2 (0034) | 2.44 | 6.59 | | | 0.59 | 4.101 |

(a) Genes expressed from Plac on pZE13, a high-copy plasmid with colE1 origin and ampicillin resistance. Gene identification numbers are as given in Table 2
(b) Genes expressed from Plac on pZA33, a medium-copy plasmid with pACYC origin and chloramphenicol resistance.
(c) Cell protein given as mg protein per mL extract.

Recombinant strains containing genes in the 4-HB pathway were then evaluated for the ability to produce 4-HB in vivo from central metabolic intermediates. Cells were grown anaerobically in LB medium to OD600 of approximately 0.4, then induced with 1 mM IPTG. One hour later, sodium succinate was added to 10 mM, and samples taken for analysis following an additional 24 and 48 hours. 4-HB in the culture broth was analyzed by GC-MS as described below. The results indicate that the recombinant strain can produce over 2 mM 4-HB after 24 hours, compared to essentially zero in the control strain (Table 8).

cost carbohydrate feedstocks such as glucose or sucrose. Thus, the next set of experiments was aimed to determine whether endogenous succinate produced by the cells during growth on glucose could fuel the 4-HB pathway. Cells were grown anaerobically in M9 minimal medium (6.78 g/L Na$_2$HPO$_4$, 3.0 g/L KH$_2$PO$_4$, 0.5 g/L NaCl, 1.0 g/L NH$_4$Cl, 1 mM MgSO$_4$, 0.1 mM CaCl$_2$) supplemented with 20 g/L glucose, 100 mM 3-(N-morpholino)propanesulfonic acid (MOPS) to improve the buffering capacity, 10 μg/mL thiamine, and the appropriate antibiotics. 0.25 mM IPTG was added when OD600 reached approximately 0.2, and samples

TABLE 8

Production of 4-HB from succinate in E. coli strains harboring plasmids
expressing various combinations of 4-HB pathway genes.

| Sample # | Host Strain | pZE13 | pZA33 | 24 Hours | | | 48 Hours | | |
|---|---|---|---|---|---|---|---|---|---|
| | | | | OD600 | 4HB, μM | 4HB norm. (a) | OD600 | 4HB, μM | 4HB norm. (a) |
| 1 | MG1655 lacIq | cat1 (0004)-sucD (0035) | 4hbd (0009) | 0.47 | 487 | 1036 | 1.04 | 1780 | 1711 |
| 2 | MG1655 lacIq | cat1 (0004)-sucD (0035) | 4hbd (0027) | 0.41 | 111 | 270 | 0.99 | 214 | 217 |
| 3 | MG1655 lacIq | cat1 (0004)-sucD (0035) | 4hbd (0036) | 0.47 | 863 | 1835 | 0.48 | 2152 | 4484 |
| 4 | MG1655 lacIq | cat1 (0004)-sucD (0035) | 4hbd (0010n) | 0.46 | 956 | 2078 | 0.49 | 2221 | 4533 |
| 5 | MG1655 lacIq | cat1 (0004)-sucD (0008) | 4hbd (0009) | 0.38 | 493 | 1296 | 0.37 | 1338 | 3616 |
| 6 | MG1655 lacIq | cat1 (0004)-sucD (0008) | 4hbd (0027) | 0.32 | 26 | 81 | 0.27 | 87 | 323 |
| 7 | MG1655 lacIq | cat1 (0004)-sucD (0008) | 4hbd (0036) | 0.24 | 506 | 2108 | 0.31 | 1448 | 4672 |
| 8 | MG1655 lacIq | cat1 (0004)-sucD (0008) | 4hbd (0010n) | 0.24 | 78 | 324 | 0.56 | 233 | 416 |
| 9 | MG1655 lacIq gabD | cat1 (0004)-sucD (0035) | 4hbd (0009) | 0.53 | 656 | 1237 | 1.03 | 1643 | 1595 |
| 10 | MG1655 lacIq gabD | cat1 (0004)-sucD (0035) | 4hbd (0027) | 0.44 | 92 | 209 | 0.98 | 214 | 218 |
| 11 | MG1655 lacIq gabD | cat1 (0004)-sucD (0035) | 4hbd (0036) | 0.51 | 1072 | 2102 | 0.97 | 2358 | 2431 |
| 12 | MG1655 lacIq gabD | cat1 (0004)-sucD (0035) | 4hbd (0010n) | 0.51 | 981 | 1924 | 0.97 | 2121 | 2186 |
| 13 | MG1655 lacIq gabD | cat1 (0004)-sucD (0008) | 4hbd (0009) | 0.35 | 407 | 1162 | 0.77 | 1178 | 1530 |
| 14 | MG1655 lacIq gabD | cat1 (0004)-sucD (0008) | 4hbd (0027) | 0.51 | 19 | 36 | 1.07 | 50 | 47 |
| 15 | MG1655 lacIq gabD | cat1 (0004)-sucD (0008) | 4hbd (0036) | 0.35 | 584 | 1669 | 0.78 | 1350 | 1731 |
| 16 | MG1655 lacIq gabD | cat1 (0004)-sucD (0008) | 4hbd (0010n) | 0.32 | 74 | 232 | 0.82 | 232 | 283 |
| 17 | MG1655 lacIq | vector only | vector only | 0.8 | 1 | 2 | 1.44 | 3 | 2 |
| 18 | MG1655 lacIq gabD | vector only | vector only | 0.89 | 1 | 2 | 1.41 | 7 | 5 |

(a) Normalized 4-HB concentration, μM/OD600 units

An alternate to using a CoA transferase (cat1) to produce succinyl-CoA from succinate is to use the native E. coli sucCD genes, encoding succinyl-CoA synthetase. This gene cluster was cloned onto pZE13 along with candidate genes for the remaining steps to 4-HB to create pZE13-0038-0035-0036.

Figure 11A:
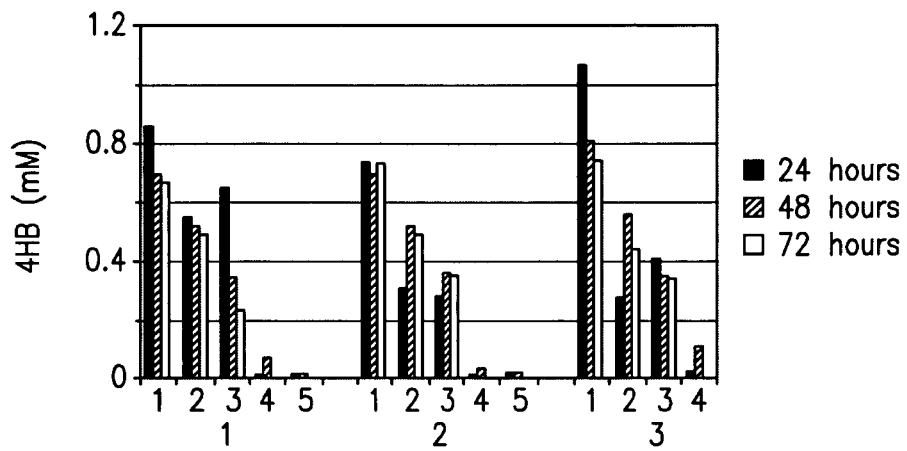
FIG. 11 shows the production of 4-HB in glucose minimal medium using *E. coli* strains harboring plasmids expressing various combinations of 4-HB pathway genes. (a) 4-HB concentration in culture broth; (b) succinate concentration in culture broth; (c) culture OD, measured at 600 nm. Clusters of bars represent the 24 hour, 48 hour, and 72 hour (if measured) timepoints. The codes along the x-axis indicate the strain/plasmid combination used. The first index refers to the host strain: 1, MG1655 lacI$^Q$; 2, MG1655 ΔgabD lacI$^Q$; 3, MG1655 ΔgabD ΔaldA lacI$^Q$. The second index refers to the plasmid combination used: 1, pZE13-0004-0035 and pZA33-0036; 2, pZE13-0004-0035 and pZA33-0010n; 3, pZE13-0004-0008 and pZA33-0036; 4, pZE13-0004-0008 and pZA33-0010n; 5, Control vectors pZE13 and pZA33.
Figure 11B:
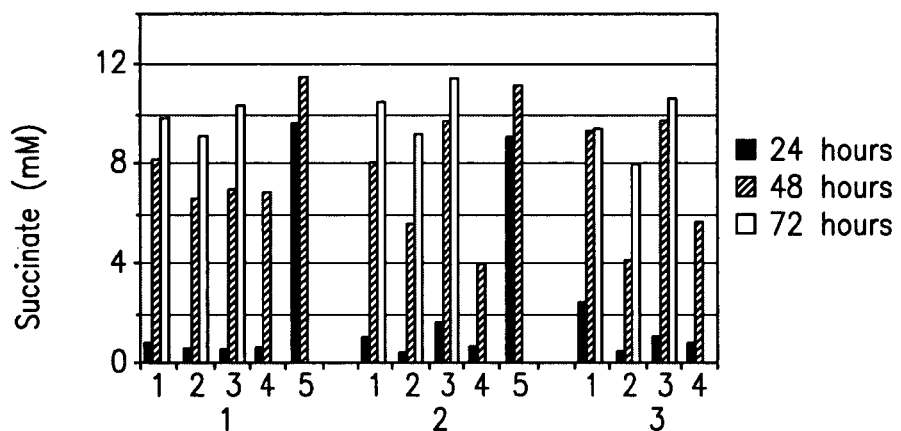
Figure 11C:
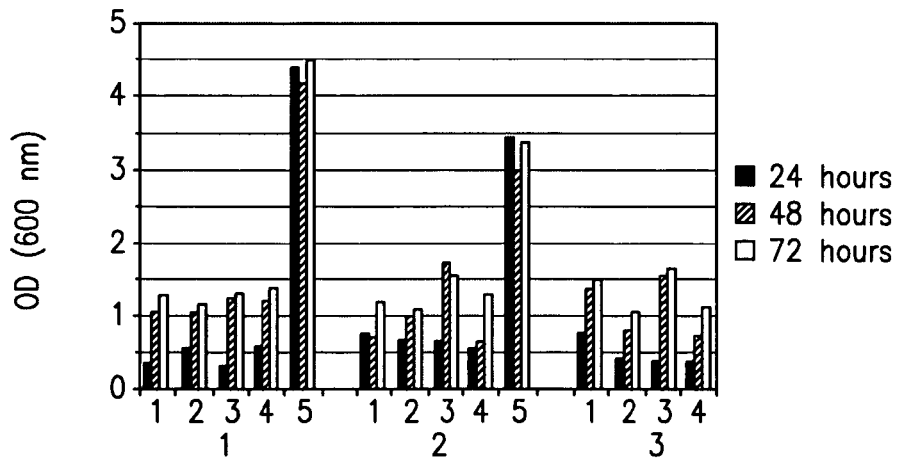

Production of 4-HB from Glucose. Although the above experiments demonstrate a functional pathway to 4-HB from a central metabolic intermediate (succinate), an industrial process would require the production of chemicals from low-cost taken for 4-HB analysis every 24 hours following induction. In all cases 4-HB plateaued after 24 hours, with a maximum of about 1 mM in the best strains (FIG. 11a), while the succinate concentration continued to rise (FIG. 11b). This indicates that the supply of succinate to the pathway is likely not limiting, and that the bottleneck may be in the activity of the enzymes themselves or in NADH availability. 0035 and 0036 are clearly the best gene candidates for CoA-dependent succinic semialdehyde dehydrogenase and 4-HB dehydrogenase, respectively. The elimination of one or both of the genes encoding known (gabD) or putative (aldA) native succinic semialdehyde dehydrogenases had little effect on performance. Finally, it should be noted that the cells grew to a much lower OD in the 4-HB-producing strains than in the controls (FIG. 11c).

Figure 12:
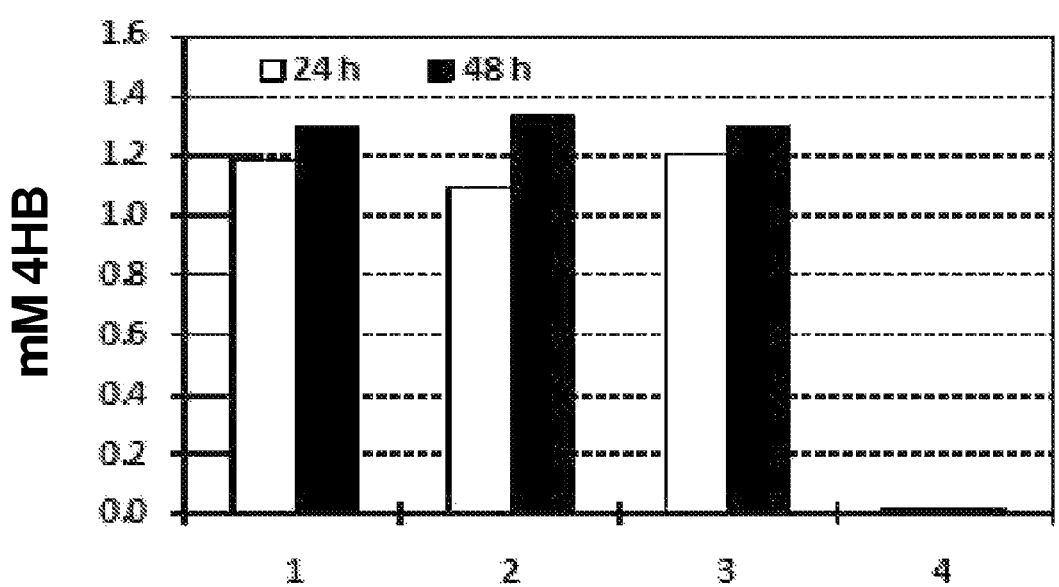
FIG. 12 shows the production of 4-HB from glucose in *E. coli* strains expressing α-ketoglutarate decarboxylase from *Mycobacterium tuberculosis*. Strains 1-3 contain pZE13-0032 and pZA33-0036. Strain 4 expresses only the empty vectors pZE13 and pZA33. Host strains are as follows: 1 and 4, MG1655 lacI$^Q$; 2, MG1655 ΔgabD lacI$^Q$; 3, MG1655 ΔgabD ΔaldA lacI$^Q$. The bars refer to concentration at 24 and 48 hours.

An alternate pathway for the production of 4-HB from glucose is via a-ketoglutarate. We explored the use of an α-ketoglutarate decarboxylase from *Mycobacterium tuberculosis* Tian et al., *Proc. Natl. Acad. Sci. USA* 102:10670-10675 (2005) to produce succinic semialdehyde directly from α-ketoglutarate (step 8 in FIG. 2). To demonstrate that this gene (0032) was functional in vivo, we expressed it on pZE13 in the same host as 4-HB dehydrogenase (gene 0036) on pZA33. This strain was capable of producing over 1.0 mM 4-HB within 24 hours following induction with 1 mM IPTG (FIG. 12). Since this strain does not express a CoA-dependent succinic semialdehyde dehydrogenase, the possibility of succinic semialdehyde production via succinyl-CoA is eliminated. It is also possible that the native genes responsible for producing succinic semialdehyde could function in this pathway (steps 4 and 5 in FIG. 2); however, the amount of 4-HB produced when the pZE13-0032 plasmid was left out of the host is the negligible.

Production of BDO from 4-HB. The production of BDO from 4-HB required two reduction steps, catalyzed by dehydrogenases. Alcohol and aldehyde dehydrogenases (ADH and ALD, respectively) are NAD+/H and/or NADP+/H-dependent enzymes that together can reduce a carboxylic acid group on a molecule to an alcohol group, or in reverse, can perform the oxidation of an alcohol to a carboxylic acid. This biotransformation has been demonstrated in wild-type *Clostridium acetobutylicum* (Jewell et al., *Current Microbiology*, 13:215-19 (1986)), but neither the enzymes responsible nor the genes responsible were identified. In addition, it is not known whether activation to 4-HB-CoA is first required (step 9 in FIG. 2), or if the aldehyde dehydrogenase (step 12) can act directly on 4-HB. We developed a list of candidate enzymes from *C. acetobutylicum* and related organisms based on known activity with the non-hydroxylated analogues to 4-HB and pathway intermediates, or by similarity to these characterized genes (Table 6). Since some of the candidates are multifunctional dehydrogenases, they could potentially catalyze both the NAD(P)H-dependent reduction of the acid (or CoA-derivative) to the aldehyde, and of the aldehyde to the alcohol. Before beginning work with these genes in *E. coli*, we first validated the result referenced above using *C. acetobutylicum* ATCC 824. Cells were grown in Schaedler broth (Accumedia, Lansing, Mich.) supplemented with 10 mM 4-HB, in an anaerobic atmosphere of 10% $CO_2$, 10% $H_2$, and 80% $N_2$ at 30° C. Periodic culture samples were taken, centrifuged, and the broth analyzed for BDO by GC-MS as described below. BDO concentrations of 0.1 mM, 0.9 mM, and 1.5 mM were detected after 1 day, 2 days, and 7 days incubation, respectively. No BDO was detected in culture grown without 4-HB addition. To demonstrate that the BDO produced was derived from glucose, we grew the best BDO producing strain MG1655 lacI$^Q$ pZE13-0004-0035-0002 pZA33-0034-0036 in M9 minimal medium supplemented with 4 g/L uniformly labeled $^{13}$C-glucose. Cells were induced at OD of 0.67 with 1 mM IPTG, and a sample taken after 24 hours. Analysis of the culture supernatant was performed by mass spectrometry.

Gene candidates for the 4-HB to BDO conversion pathway were next tested for activity when expressed in the *E. coli* host MG1655 lacI$^Q$. Recombinant strains containing each gene candidate expressed on pZA33 were grown in the presence of 0.25 mM IPTG for four hours at 37° C. to fully induce expression of the enzyme. Four hours after induction, cells were harvested and assayed for ADH and ALD activity as described above. Since 4-HB-CoA and 4-hydroxybutyraldehyde are not available commercially, assays were performed using the non-hydroxylated substrates (Table 9). The ratio in activity between 4-carbon and 2-carbon substrates for *C. acetobutylicum* adhE2 (0002) and *E. coli* adhE (0011) were similar to those previously reported in the literature a Atsumi et al., *Biochim. Biophys. Acta*. 1207:1-11 (1994).

TABLE 9

In vitro enzyme activities in cell extracts from MG1655 lacI$^Q$ containing pZA33 expressing gene candidates for aldehyde and alcohol dehydrogenases. Activities are expressed in $\mu$mol min$^{-1}$ mg cell protein$^{-1}$.

| | | Aldehyde dehydrogenase | | Alcohol dehydrogenase | |
|---|---|---|---|---|---|
| Gene | Substrate | Butyryl-CoA | Acetyl-CoA | Butyraldehyde | Acetaldehyde |
| 0002 | | 0.0076 | 0.0046 | 0.0264 | 0.0247 |
| 0003n | | 0.0060 | 0.0072 | 0.0080 | 0.0075 |
| 0011 | | 0.0069 | 0.0095 | 0.0265 | 0.0093 |
| 0013 | | N.D. | N.D. | 0.0130 | 0.0142 |
| 0023 | | 0.0089 | 0.0137 | 0.0178 | 0.0235 |
| 0025 | | 0 | 0.0001 | N.D. | N.D. |
| 0026 | | 0 | 0.0005 | 0.0024 | 0.0008 |

N.D., not determined.

Figure 13:
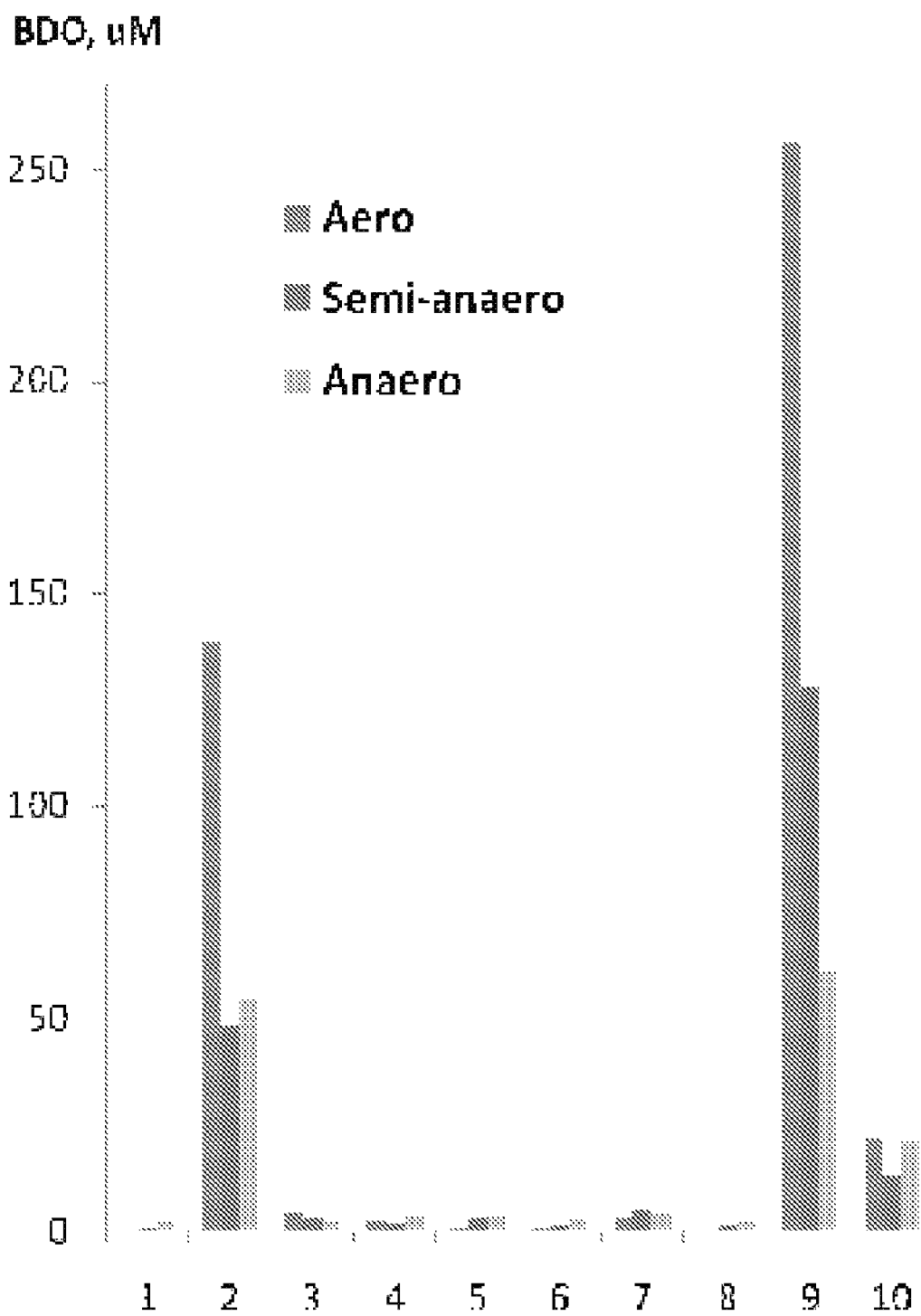
FIG. 13 shows the production of BDO from 10 mM 4-HB in recombinant *E. coli* strains. Numbered positions correspond to experiments with MG1655 lacI$^Q$ containing pZA33-0024, expressing cat2 from *P. gingivalis*, and the following genes expressed on pZE13: 1, none (control); 2, 0002; 3, 0003; 4, 0003n; 5, 0011; 6, 0013; 7, 0023; 8, 0025; 9, 0008n; 10, 0035. Gene numbers are defined in Table 6. For each position, the bars refer to aerobic, microaerobic, and anaerobic conditions, respectively. Microaerobic conditions were created by sealing the culture tubes but not evacuating them.
Figure 14A:
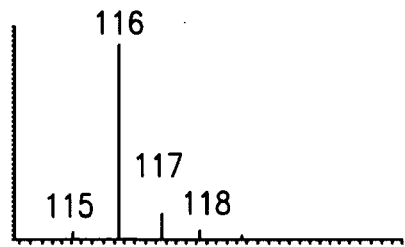
FIG. 14 shows the mass spectrum of 4-HB and BDO produced by MG1655 lacI$^Q$ pZE13-0004-0035-0002 pZA33-0034-0036 grown in M9 minimal medium supplemented with 4 g/L unlabeled glucose (a, c, e, and g) uniformly labeled $^{13}$C-glucose (b, d, f, and h). (a) and (b), mass 116 characteristic fragment of derivatized BDO, containing 2 carbon atoms; (c) and (d), mass 177 characteristic fragment of derivatized BDO, containing 1 carbon atom; (e) and (f), mass 117 characteristic fragment of derivatized 4-HB, containing 2 carbon atoms; (g) and (h), mass 233 characteristic fragment of derivatized 4-HB, containing 4 carbon atoms.
Figure 14B:
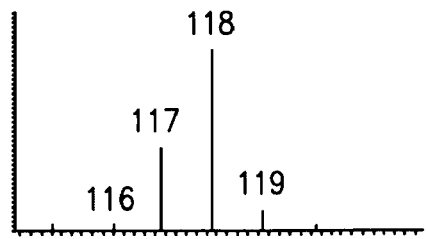
Figure 14C:
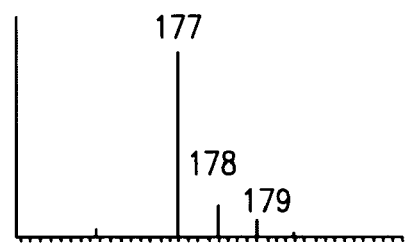
Figure 14D:
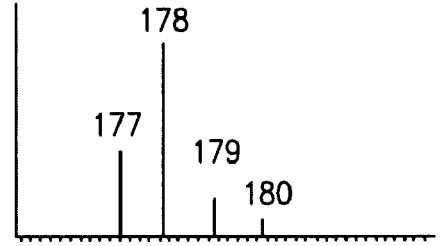
Figure 14E:
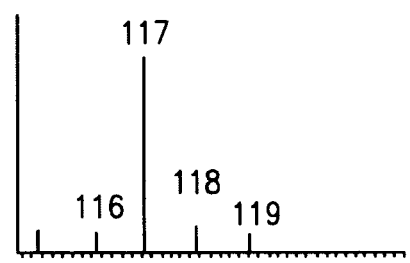
Figure 14F:
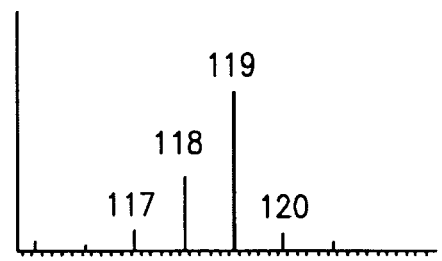
Figure 14G:
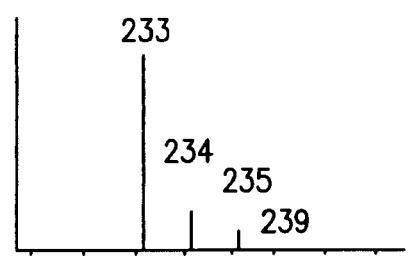
Figure 14H:
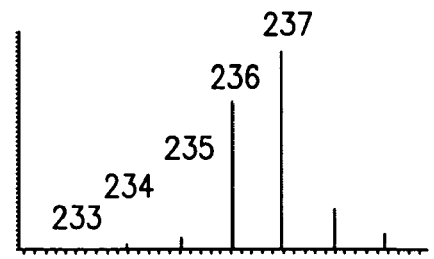

For the BDO production experiments, cat2 from *Porphyromonas gingivalis* W83 (gene 0034) was included on pZA33 for the conversion of 4-HB to 4-HB-CoA, while the candidate dehydrogenase genes were expressed on pZE13. The host strain was MG1655 lacI$^Q$. Along with the alcohol and aldehyde dehydrogenase candidates, we also tested the ability of CoA-dependent succinic semialdehyde dehydrogenases (sucD) to function in this step, due to the similarity of the substrates. Cells were grown to an OD of about 0.5 in LB medium supplemented with 10 mM 4-HB, induced with 1 mM IPTG, and culture broth samples taken after 24 hours and analyzed for BDO as described below. The best BDO production occurred using adhE2 from *C. acetobutylicum*, sucD from *C. kluyveri*, or sucD from *P. gingivalis* (FIG. 13). Interestingly, the absolute amount of BDO produced was higher under aerobic conditions; however, this is primarily due to the lower cell density achieved in anaerobic cultures. When normalized to cell OD, the BDO production per unit biomass is higher in anaerobic conditions (Table 10).

TABLE 10

Absolute and normalized BDO concentrations from cultures of cells expressing adhE2 from *C. acetobutylicum*, sucD from *C. kluyveri*, or sucD from *P. gingivalis* (data from experiments 2, 9, and 10 in FIG. 11), as well as the negative control (experiment 1).

| Gene expressed | Conditions | BDO (µM) | OD (600 nm) | BDO/OD |
|---|---|---|---|---|
| none | Aerobic | 0 | 13.4 | 0 |
| none | Microaerobic | 0.5 | 6.7 | 0.09 |
| none | Anaerobic | 2.2 | 1.26 | 1.75 |
| 0002 | Aerobic | 138.3 | 9.12 | 15.2 |
| 0002 | Microaerobic | 48.2 | 5.52 | 8.73 |
| 0002 | Anaerobic | 54.7 | 1.35 | 40.5 |
| 0008n | Aerobic | 255.8 | 5.37 | 47.6 |
| 0008n | Microaerobic | 127.9 | 3.05 | 41.9 |
| 0008n | Anaerobic | 60.8 | 0.62 | 98.1 |
| 0035 | Aerobic | 21.3 | 14.0 | 1.52 |
| 0035 | Microaerobic | 13.1 | 4.14 | 3.16 |
| 0035 | Anaerobic | 21.3 | 1.06 | 20.1 |

As discussed in Section 2, it may be advantageous to use a route for converting 4-HB to 4-HB-CoA that does not generate acetate as a byproduct. To this aim, we tested the use of phosphotransbutyrylase (ptb) and butyrate kinase (bk) from *C. acetobutylicum* to carry out this conversion via steps 10 and 11 in FIG. 2. The native ptb/bk operon from *C. acetobutylicum* (genes 0020 and 0021) was cloned and expressed in pZA33. Extracts from cells containing the resulting construct were taken and assayed for the two enzyme activities as described herein. The specific activity of BK was approximately 65 U/mg, while the specific activity of PTB was approximately 5 U/mg. One unit (U) of activity is defined as conversion of 1 µM substrate in 1 minute at room temperature. Finally, the construct was tested for participation in the conversion of 4-HB to BDO. Host strains were transformed with the pZA33-0020-0021 construct described and pZE13-0002, and compared to use of cat2 in BDO production using the aerobic procedure used above in FIG. 13. The BK/PTB strain produced 1 mM BDO, compared to 2 mM when using cat2 (Table 11). Interestingly, the results were dependent on whether the host strain contained a deletion in the native adhE gene.

TABLE 11

Absolute and normalized BDO concentrations from cultures of cells expressing adhE2 from *C. acetobutylicum* in pZE13 along with either cat2 from *P. gingivalis* (0034) or the PTB/BK genes from *C. acetobutylicum* on pZA33. Host strains were either MG1655 lacI$^Q$ or MG1655 ΔadhE lacI$^Q$.

| Genes | Host Strain | BDO (µM) | OD (600 nm) | BDO/OD |
|---|---|---|---|---|
| 0034 | MG1655 lacI$^Q$ | 0.827 | 19.9 | 0.042 |
| 0020 + 0021 | MG1655 lacI$^Q$ | 0.007 | 9.8 | 0.0007 |
| 0034 | MG1655 ΔadhE lacI$^Q$ | 2.084 | 12.5 | 0.166 |
| 0020 + 0021 | MG1655 ΔadhE lacI$^Q$ | 0.975 | 18.8 | 0.052 |

Production of BDO from Glucose. The final step of pathway corroboration is to express both the 4-HB and BDO segments of the pathway in *E. coli* and demonstrate production of BDO in glucose minimal medium. New plasmids were constructed so that all the required genes fit on two plasmids. In general, cat1, adhE, and sucD genes were expressed from pZE13, and cat2 and 4-HBd were expressed from pZA33. Various combinations of gene source and gene order were tested in the MG1655 lacI$^Q$ background. Cells were grown anaerobically in M9 minimal medium (6.78 g/L Na$_2$HPO$_4$, 3.0 g/L KH$_2$PO$_4$, 0.5 g/L NaCl, 1.0 g/L NH$_4$Cl, 1 mM MgSO$_4$, 0.1 mM CaCl$_2$) supplemented with 20 g/L glucose, 100 mM 3-(N-morpholino)propanesulfonic acid (MOPS) to improve the buffering capacity, 10 µg/mL thiamine, and the appropriate antibiotics. 0.25 mM IPTG was added approximately 15 hours following inoculation, and culture supernatant samples taken for BDO, 4-HB, and succinate analysis 24 and 48 hours following induction. The production of BDO appeared to show a dependency on gene order (Table 12). The highest BDO production, over 0.5 mM, was obtained with cat2 expressed first, followed by 4-HBd on pZA33, and cat1 followed by *P. gingivalis* sucD on pZE13. The addition of *C. acetobutylicum* adhE2 in the last position on pZE13 resulted in slight improvement. 4-HB and succinate were also produced at higher concentrations.

TABLE 12

Production of BDO, 4-HB, and succinate in recombinant *E. coli* strains expressing combinations of BDO pathway genes, grown in minimal medium supplemented with 20 g/L glucose. Concentrations are given in mM.

| Sample | pZE13 | pZA33 | Induction OD | 24 Hours OD600 nm | Su | 4HB | BDO | 48 Hours OD600 nm | Su | 4HB | BDO |
|---|---|---|---|---|---|---|---|---|---|---|---|
| 1 | cat1 (0004)-sucD (0035) | 4hbd (0036)-cat2 (0034) | 0.92 | 1.29 | 5.44 | 1.37 | 0.240 | 1.24 | 6.42 | 1.49 | 0.280 |
| 2 | cat1 (0004)-sucD (0008N) | 4hbd (0036)-cat2 (0034) | 0.36 | 1.11 | 6.90 | 1.24 | 0.011 | 1.06 | 7.63 | 1.33 | 0.011 |
| 3 | adhE (0002)-cat1 (0004)-sucD (0035) | 4hbd (0036)-cat2 (0034) | 0.20 | 0.44 | 0.34 | 1.84 | 0.050 | 0.60 | 1.93 | 2.67 | 0.119 |
| 4 | cat1 (0004)-sucD (0035)-adhE (0002) | 4hbd (0036)-cat2 (0034) | 1.31 | 1.90 | 9.02 | 0.73 | 0.073 | 1.95 | 9.73 | 0.82 | 0.077 |
| 5 | adhE (0002)-cat1 (0004)-sucD (0008N) | 4hbd (0036)-cat2 (0034) | 0.17 | 0.45 | 1.04 | 1.04 | 0.008 | 0.94 | 7.13 | 1.02 | 0.017 |
| 6 | cat1 (0004)-sucD (0008N)-adhE (0002) | 4hbd (0036)-cat2 (0034) | 1.30 | 1.77 | 10.47 | 0.25 | 0.004 | 1.80 | 11.49 | 0.28 | 0.003 |
| 7 | cat1 (0004)-sucD (0035) | cat2 (0034)-4hbd (0036) | 1.09 | 1.29 | 5.63 | 2.15 | 0.461 | 1.38 | 6.66 | 2.30 | 0.520 |
| 8 | cat1 (0004)-sucD (0008N) | cat2 (0034)-4hbd (0036) | 1.81 | 2.01 | 11.28 | 0.02 | 0.000 | 2.24 | 11.13 | 0.02 | 0.000 |
| 9 | adhE (0002)-cat1 (0004)-sucD (0035) | cat2 (0034)-4hbd (0036) | 0.24 | 1.99 | 2.02 | 2.32 | 0.106 | 0.89 | 4.85 | 2.41 | 0.186 |
| 10 | cat1 (0004)-sucD (0035)-adhE (0002) | cat2 (0034)-4hbd (0036) | 0.98 | 1.17 | 5.30 | 2.08 | 0.569 | 1.33 | 6.15 | 2.14 | 0.640 |
| 11 | adhE (0002)-cat1 (0004)-sucD (0008N) | cat2 (0034)-4hbd (0036) | 0.20 | 0.53 | 1.38 | 2.30 | 0.019 | 0.91 | 8.10 | 1.49 | 0.034 |
| 12 | cat1 (0004)-sucD (0008N)-adhE (0002) | cat2 (0034)-4hbd (0036) | 2.14 | 2.73 | 12.07 | 0.16 | 0.000 | 3.10 | 11.79 | 0.17 | 0.002 |
| 13 | vector only | vector only | 2.11 | 2.62 | 9.03 | 0.01 | 0.000 | 3.00 | 12.05 | 0.01 | 0.000 |

Analysis of BDO, 4-HB and succinate by GCMS. BDO, 4-HB and succinate in fermentation and cell culture samples were derivatized by silylation and quantitatively analyzed by GCMS using methods adapted from literature reports ((Simonov et al., *J. Anal Chem.* 59:965-971 (2004)). The developed method demonstrated good sensitivity down to 1 μM, linearity up to at least 25 mM, as well as excellent selectivity and reproducibility.

Sample preparation was performed as follows: 100 μL filtered (0.2 μm or 0.45 μm syringe filters) samples, e.g. fermentation broth, cell culture or standard solutions, were dried down in a Speed Vac Concentrator (Savant SVC-100H) for approximately 1 hour at ambient temperature, followed by the addition of 20 μL 10 mM cyclohexanol solution, as an internal standard, in dimethylformamide. The mixtures were vortexed and sonicated in a water bath (Branson 3510) for 15 min to ensure homogeneity. 100 μL silylation derivatization reagent, N,O-bis(trimethylsilyl)trifluoro-acetimide (BSTFA) with 1% trimethylchlorosilane, was added, and the mixture was incubated at 70° C. for 30 min. The derivatized samples were centrifuged for 5 min, and the clear solutions were directly injected into GCMS. All the chemicals and reagents were from Sigma-Aldrich, with the exception of BDO which was purchased from J. T. Baker.

GCMS was performed on an Agilent gas chromatograph 6890N, interfaced to a mass-selective detector (MSD) 5973N operated in electron impact ionization (EI) mode has been used for the analysis. A DB-5MS capillary column (J&W Scientific, Agilent Technologies), 30 m×0.25 mm i.d.×0.25 μm film thickness, was used. The GC was operated in a split injection mode introducing 1 μL of sample at 20:1 split ratio. The injection port temperature was 250° C. Helium was used as a carrier gas, and the flow rate was maintained at 1.0 mL/min. A temperature gradient program was optimized to ensure good resolution of the analytes of interest and minimum matrix interference. The oven was initially held at 80° C. for 1 min, then ramped to 120° C. at 2° C./min, followed by fast ramping to 320° C. at 100° C./min and final hold for 6 min at 320° C. The MS interface transfer line was maintained at 280° C. The data were acquired using 'lowmass' MS tune settings and 30-400 m/z mass-range scan. The total analysis time was 29 min including 3 min solvent delay. The retention times corresponded to 5.2, 10.5, 14.0 and 18.2 min for BSTFA-derivatized cyclohexanol, BDO, 4-HB and succinate, respectively. For quantitative analysis, the following specific mass fragments were selected (extracted ion chromatograms): m/z 157 for internal standard cyclohexanol, 116 for BDO, and 147 for both 4-HB and succinate. Standard calibration curves were constructed using analyte solutions in the corresponding cell culture or fermentation medium to match sample matrix as close as possible. GCMS data were processed using Environmental Data Analysis ChemStation software (Agilent Technologies).

The results indicated that most of the 4-HB and BDO produced were labeled with $^{13}C$ (FIG. 14, right-hand sides). Mass spectra from a parallel culture grown in unlabeled glucose are shown for comparison (FIG. 14, left-hand sides). Note that the peaks seen are for fragments of the derivatized molecule containing different numbers of carbon atoms from the metabolite. The derivatization reagent also contributes some carbon and silicon atoms that naturally-occurring label distribution, so the results are not strictly quantitative.

Production of BDO from 4-HB using alternate pathways. The various alternate pathways were also tested for BDO production. This includes use of the native *E. coli* SucCD enzyme to convert succinate to succinyl-CoA (Table 13, rows 2-3), use of α-ketoglutarate decarboxylase in the α-ketoglutarate pathway (Table 13, row 4), and use of PTB/BK as an alternate means to generate the CoA-derivative of 4HB (Table 13, row 1). Strains were constructed containing plasmids expressing the genes indicated in Table 13, which encompass these variants. The results show that in all cases, production of 4-HB and BDO occurred (Table 13).

TABLE 13

Production of BDO, 4-HB, and succinate in recombinant *E. coli* strains genes for different BDO pathway variants, grown anaerobically in minimal medium supplemented with 20 g/L glucose, and harvested 24 hours after induction with 0.1 mM IPTG.
Concentrations are given in mM.

| Genes on pZE13 | Genes on pZA33 | Succinate | 4-HB | BDO |
| --- | --- | --- | --- | --- |
| 0002 + 0004 + 0035 | 0020n – 0021n – 0036 | 0.336 | 2.91 | 0.230 |
| 0038 + 0035 | 0034 – 0036 | 0.814 | 2.81 | 0.126 |
| 0038 + 0035 | 0036 – 0034 | 0.741 | 2.57 | 0.114 |
| 0035 + 0032 | 0034 – 0036 | 5.01 | 0.538 | 0.154 |

EXAMPLE V

Biosynthesis of 4-Hydroxybutanoic Acid, γ-Butyrolactone and 1,4-Butanediol

This Example describes the biosynthetic production of 4-hydroxybutanoic acid, γ-butyrolactone and 1,4-butanediol using fermentation and other bioprocesses.

Figure 15:
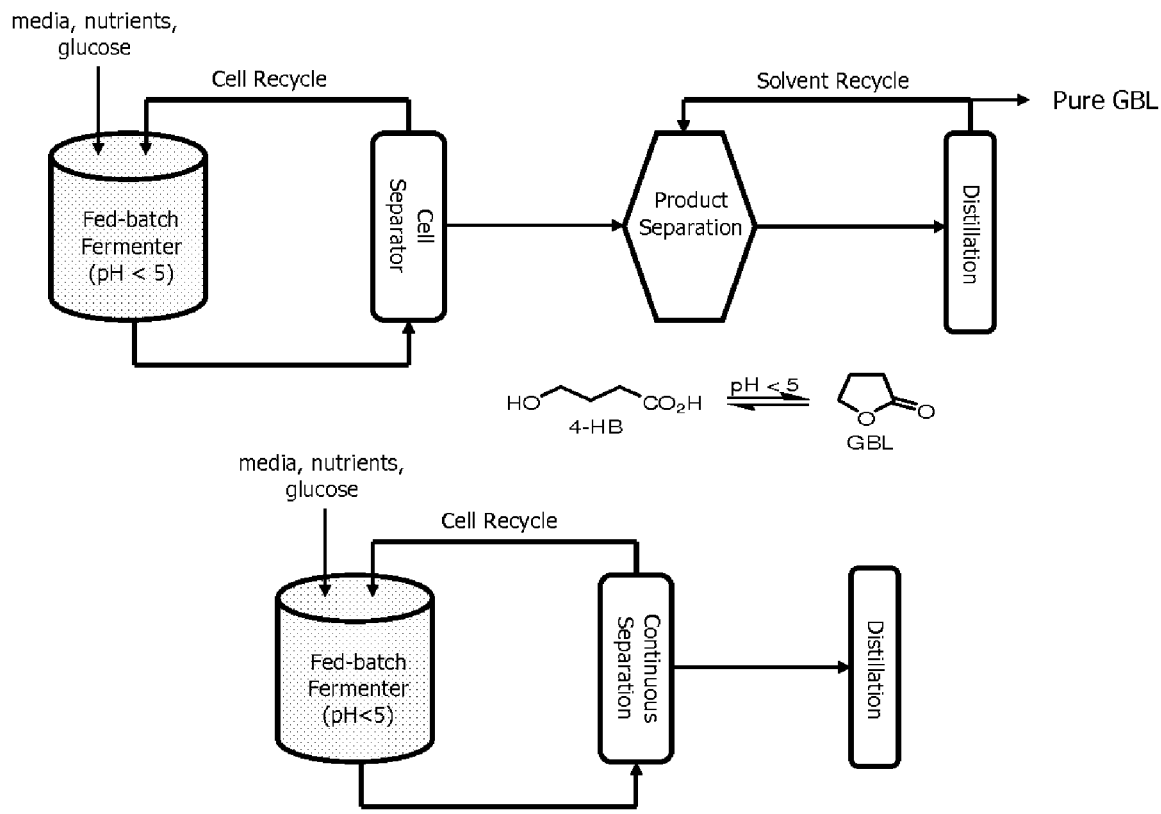
FIG. 15 is a schematic process flow diagram of bioprocesses for the production of γ-butyrolactone. Panel (a) illustrates fed-batch fermentation with batch separation and panel (b) illustrates fed-batch fermentation with continuous separation.

Methods for the integration of the 4-HB fermentation step into a complete process for the production of purified GBL, 1,4-butanediol (BDO) and tetrahydrofuran (THF) are described below. Since 4-HB and GBL are in equilibrium, the fermentation broth will contain both compounds. At low pH this equilibrium is shifted to favor GBL. Therefore, the fermentation can operate at pH 7.5 or less, generally pH 5.5 or less. After removal of biomass, the product stream enters into a separation step in which GBL is removed and the remaining stream enriched in 4-HB is recycled. Finally, GBL is distilled to remove any impurities. The process operates in one of three ways: 1) fed-batch fermentation and batch separation; 2) fed-batch fermentation and continuous separation; 3) continuous fermentation and continuous separation. The first two of these modes are shown schematically in FIG. 15. The integrated fermentation procedures described below also are used for the BDO producing cells of the invention for biosynthesis of BDO and subsequent BDO family products.

Fermentation protocol to produce 4-HB/GBL (batch): The production organism is grown in a 10 L bioreactor sparged with an $N_2/CO_2$ mixture, using 5 L broth containing 5 g/L potassium phosphate, 2.5 g/L ammonium chloride, 0.5 g/L magnesium sulfate, and 30 g/L corn steep liquor, and an initial glucose concentration of 20 g/L. As the cells grow and utilize the glucose, additional 70% glucose is fed into the bioreactor at a rate approximately balancing glucose consumption. The temperature of the bioreactor is maintained at 30 degrees C. Growth continues for approximately 24 hours, until 4-HB reaches a concentration of between 20-200 g/L, with the cell density being between 5 and 10 g/L. The pH is not controlled, and will typically decrease to pH 3-6 by the end of the run. Upon completion of the cultivation period, the fermenter contents are passed through a cell separation unit (e.g., centrifuge) to remove cells and cell debris, and the fermentation broth is transferred to a product separations unit. Isolation of 4-HB and/or GBL would take place by standard separations procedures employed in the art to separate organic products from dilute aqueous solutions, such as liquid-liquid extraction using a water immiscible organic solvent (e.g., toluene) to provide an organic solution of 4-HB/GBL. The resulting solution is then subjected to standard distillation methods to remove and recycle the organic solvent and to provide GBL (boiling point 204-205° C.) which is isolated as a purified liquid.

Fermentation protocol to produce 4-HB/GBL (fully continuous): The production organism is first grown up in batch mode using the apparatus and medium composition described above, except that the initial glucose concentration is 30-50 g/L. When glucose is exhausted, feed medium of the same composition is supplied continuously at a rate between 0.5 L/hr and 1 L/hr, and liquid is withdrawn at the same rate. The 4-HB concentration in the bioreactor remains constant at 30-40 g/L, and the cell density remains constant between 3-5 g/L. Temperature is maintained at 30 degrees C, and the pH is maintained at 4.5 using concentrated NaOH and HCl, as required. The bioreactor is operated continuously for one month, with samples taken every day to assure consistency of 4-HB concentration. In continuous mode, fermenter contents are constantly removed as new feed medium is supplied. The exit stream, containing cells, medium, and products 4-HB and/or GBL, is then subjected to a continuous product separations procedure, with or without removing cells and cell debris, and would take place by standard continuous separations methods employed in the art to separate organic products from dilute aqueous solutions, such as continuous liquid-liquid extraction using a water immiscible organic solvent (e.g., toluene) to provide an organic solution of 4-HB/GBL. The resulting solution is subsequently subjected to standard continuous distillation methods to remove and recycle the organic solvent and to provide GBL (boiling point 204-205° C.) which is isolated as a purified liquid.

GBL Reduction Protocol: Once GBL is isolated and purified as described above, it will then be subjected to reduction protocols such as those well known in the art (references cited) to produce 1,4-butanediol or tetrahydrofuran (THF) or a mixture thereof. Heterogeneous or homogeneous hydrogenation catalysts combined with GBL under hydrogen pressure are well known to provide the products 1,4-butanediol or tetrahydrofuran (THF) or a mixture thereof. It is important to note that the 4-HB/GBL product mixture that is separated from the fermentation broth, as described above, may be subjected directly, prior to GBL isolation and purification, to these same reduction protocols to provide the products 1,4-butanediol or tetrahydrofuran or a mixture thereof. The resulting products, 1,4-butanediol and THF are then isolated and purified by procedures well known in the art.

Fermentation and hydrogenation protocol to produce BDO or THF directly (batch): Cells are grown in a 10 L bioreactor sparged with an $N_2/CO_2$ mixture, using 5 L broth containing 5 g/L potassium phosphate, 2.5 g/L ammonium chloride, 0.5 g/L magnesium sulfate, and 30 g/L corn steep liquor, and an initial glucose concentration of 20 g/L. As the cells grow and utilize the glucose, additional 70% glucose is fed into the bioreactor at a rate approximately balancing glucose consumption. The temperature of the bioreactor is maintained at 30 degrees C. Growth continues for approximately 24 hours, until 4-HB reaches a concentration of between 20-200 g/L, with the cell density being between 5 and 10 g/L. The pH is not controlled, and will typically decrease to pH 3-6 by the end of the run. Upon completion of the cultivation period, the fermenter contents are passed through a cell separation unit (e.g., centrifuge) to remove cells and cell debris, and the fermentation broth is transferred to a reduction unit (e.g., hydrogenation vessel), where the mixture 4-HB/GBL is directly reduced to either 1,4-butanediol or THF or a mixture thereof. Following completion of the reduction procedure, the reactor contents are transferred to a product separations unit. Isolation of 1,4-butanediol and/or THF would take place by standard separations procedures employed in the art to separate organic products from dilute aqueous solutions, such as liquid-liquid extraction using a water immiscible organic solvent (e.g., toluene) to provide an organic solution of 1,4-butanediol and/or THF. The resulting solution is then subjected to standard distillation methods to remove and recycle the organic solvent and to provide 1,4-butanediol and/or THF which are isolated as a purified liquids.

Fermentation and hydrogenation protocol to produce BDO or THF directly (fully continuous): The cells are first grown up in batch mode using the apparatus and medium composition described above, except that the initial glucose concentration is 30-50 g/L. When glucose is exhausted, feed medium of the same composition is supplied continuously at a rate between 0.5 L/hr and 1 L/hr, and liquid is withdrawn at the same rate. The 4-HB concentration in the bioreactor remains constant at 30-40 g/L, and the cell density remains constant between 3-5 g/L. Temperature is maintained at 30 degrees C., and the pH is maintained at 4.5 using concentrated NaOH and HCl, as required. The bioreactor is operated continuously for one month, with samples taken every day to assure consistency of 4-HB concentration. In continuous mode, fermenter contents are constantly removed as new feed medium is supplied. The exit stream, containing cells, medium, and products 4-HB and/or GBL, is then passed through a cell separation unit (e.g., centrifuge) to remove cells and cell debris, and the fermentation broth is transferred to a continuous reduction unit (e.g., hydrogenation vessel), where the mixture 4-HB/GBL is directly reduced to either 1,4-butanediol or THF or a mixture thereof. Following completion of the reduction procedure, the reactor contents are transferred to a continuous product separations unit. Isolation of 1,4-butanediol and/or THF would take place by standard continuous separations procedures employed in the art to separate organic products from dilute aqueous solutions, such as liquid-liquid extraction using a water immiscible organic solvent (e.g., toluene) to provide an organic solution of 1,4-butanediol and/or THF. The resulting solution is then subjected to standard continuous distillation methods to remove and recycle the organic solvent and to provide 1,4-butanediol and/or THF which are isolated as a purified liquids.

Fermentation protocol to produce BDO directly (batch): The production organism is grown in a 10 L bioreactor sparged with an $N_2/CO_2$ mixture, using 5 L broth containing 5 g/L potassium phosphate, 2.5 g/L ammonium chloride, 0.5 g/L magnesium sulfate, and 30 g/L corn steep liquor, and an initial glucose concentration of 20 g/L. As the cells grow and utilize the glucose, additional 70% glucose is fed into the bioreactor at a rate approximately balancing glucose consumption. The temperature of the bioreactor is maintained at 30 degrees C. Growth continues for approximately 24 hours, until BDO reaches a concentration of between 20-200 g/L, with the cell density generally being between 5 and 10 g/L. Upon completion of the cultivation period, the fermenter contents are passed through a cell separation unit (e.g., centrifuge) to remove cells and cell debris, and the fermentation broth is transferred to a product separations unit. Isolation of BDO would take place by standard separations procedures employed in the art to separate organic products from dilute aqueous solutions, such as liquid-liquid extraction using a water immiscible organic solvent (e.g., toluene) to provide an organic solution of BDO. The resulting solution is then subjected to standard distillation methods to remove and recycle the organic solvent and to provide BDO (boiling point 228-229° C.) which is isolated as a purified liquid.

Fermentation protocol to produce BDO directly (fully continuous): The production organism is first grown up in batch mode using the apparatus and medium composition described above, except that the initial glucose concentration is 30-50 g/L. When glucose is exhausted, feed medium of the same composition is supplied continuously at a rate between 0.5 L/hr and 1 L/hr, and liquid is withdrawn at the same rate. The BDO concentration in the bioreactor remains constant at 30-40 g/L, and the cell density remains constant between 3-5 g/L. Temperature is maintained at 30 degrees C., and the pH is maintained at 4.5 using concentrated NaOH and HCl, as required. The bioreactor is operated continuously for one month, with samples taken every day to assure consistency of BDO concentration. In continuous mode, fermenter contents are constantly removed as new feed medium is supplied. The exit stream, containing cells, medium, and the product BDO, is then subjected to a continuous product separations procedure, with or without removing cells and cell debris, and would take place by standard continuous separations methods employed in the art to separate organic products from dilute aqueous solutions, such as continuous liquid-liquid extraction using a water immiscible organic solvent (e.g., toluene) to provide an organic solution of BDO. The resulting solution is subsequently subjected to standard continuous distillation methods to remove and recycle the organic solvent and to provide BDO (boiling point 228-229° C.) which is isolated as a purified liquid (mpt 20° C.).

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

decarboxylase, said enzyme converting α-ketoglutarate to succinic semialdehyde, or an α-ketoglutarate dehydrogenase, said enzyme converting α-ketoglutarate to succinyl-CoA, and a CoA-dependent succinic semialdehyde dehydrogenase, said enzyme converting succinyl-CoA to succinic semialdehyde, or a glutamate:succinate semialdehyde transaminase, said enzyme converting α-ketoglutarate to succinic semialdehyde, and a glutamate decarboxylase, said enzyme converting glutamate to 4-aminobutyrate; b) a 4-hydroxybutanoate dehydrogenase, said enzyme converting succinic semialdehyde to 4-hydroxybutanoic acid; c) a 4-hydroxybutyryl-CoA: acetyl-CoA transferase, said enzyme converting 4-hydroxybutanoic acid to 4-hydroxybutyryl-CoA, or a butyrate kinase and a phosphotransbutyrylase, said enzymes converting 4-hydroxybutanoic acid to 4-hydroxybutyrylphosphate and 4-hydroxybutyrylphosphate to 4-hydroxybutyryl-CoA, respectively; d) an aldehyde dehydrogenase, said enzyme converting 4-hydroxybutyryl-CoA to 4-hydroxybutyraldehyde, and e) an alcohol dehydrogenase, said enzyme converting 4-hydroxybutyraldehyde to 1,4-butanediol, wherein said exogenous nucleic acids are expressed in sufficient amounts to produce 1,4-butanediol (1,4-BDO).

2. The non-naturally occurring bacterial organism of claim 1, further comprising a CoA-dependent succinic semialdehyde dehydrogenase, said enzyme converting succinyl-CoA to succinic semialdehyde.

3. The non-naturally occurring bacterial organism of claim 1, wherein said exogenous nucleic acids comprise at least one heterologous nucleic acid.

4. The non-naturally occurring bacterial organism of claim 1 in a substantially anaerobic culture medium.

5. The non-naturally occurring bacterial organism of claim 1, comprising an α-ketoglutarate decarboxylase, said enzyme converting α-ketoglutarate to succinic semialdehyde.

---

---

What is claimed is:

1. A non-naturally occurring bacterial organism having 4-hydroxybutanoic acid (4-HB) and 1,4-butanediol (1,4-BDO) biosynthetic pathways, said pathways comprising exogenous nucleic acids encoding a) an α-ketoglutarate 6. The non-naturally occurring bacterial organism of claim 1, comprising an α-ketoglutarate dehydrogenase, said enzyme converting α-ketoglutarate to succinyl-CoA, and a CoA-dependent succinic semialdehyde dehydrogenase, said enzyme converting succinyl-CoA to succinic semialdehyde.

7. The non-naturally occurring bacterial organism of claim 1, comprising a glutamate:succinate semialdehyde transaminase, said enzyme converting α-ketoglutarate to succinic semialdehyde, and a glutamate decarboxylase, said enzyme converting glutamate to 4-aminobutyrate.

8. The non-naturally occurring bacterial organism of claim 1, comprising a 4-hydroxybutyryl-CoA:acetyl-CoA transferase, said enzyme converting 4-hydroxybutanoic acid to 4-hydroxybutyryl-CoA.

9. The non-naturally occurring bacterial organism of claim 1, comprising a butyrate kinase and a phosphotransbutyrylase, said enzymes converting 4-hydroxybutanoic acid to 4-hydroxybutyrylphosphate and 4-hydroxybutyrylphosphate to 4-hydroxybutyryl-CoA, respectively.

10. A method for the production of 1,4-BDO comprising, culturing the non-naturally occurring bacterial organism of claim 1 for a sufficient period of time to produce 1,4-BDO.

11. The method of claim 10, wherein at least one exogenous nucleic acid comprises a heterologous nucleic acid.

12. The method of claim 10, wherein said bacterial organism is cultured under substantially anaerobic conditions.

* * * * *

SEQUENCE LISTING

```
<160> NUMBER OF SEQ ID NOS: 2

<210> SEQ ID NO 1
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gacgaattcg ctagcaagag gagaagtcga catgtccaat tcactggccg tcgttttac        59

<210> SEQ ID NO 2
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gaccctagga agctttctag agtcgaccta tgcggcatca gagcaga                     47
```